United States Patent [19]
Igarashi

[11] Patent Number: 5,902,232
[45] Date of Patent: May 11, 1999

[54] NON-FLEXIBLE ENDOSCOPE HAVING A SLENDER INSERT SECTION

[75] Inventor: Tsutomu Igarashi, Hachioji, Japan

[73] Assignee: Olympus Optical Co., Ltd., Tokyo, Japan

[21] Appl. No.: 08/824,754

[22] Filed: Mar. 26, 1997

Related U.S. Application Data

[62] Division of application No. 08/396,428, Feb. 28, 1995, Pat. No. 5,632,718.

[30]  Foreign Application Priority Data

| Mar. 11, 1994 | [JP] | Japan | 6-066493 |
| Apr. 8, 1994 | [JP] | Japan | 6-093920 |
| Sep. 2, 1994 | [JP] | Japan | 6-232433 |
| Feb. 13, 1995 | [JP] | Japan | 7-046630 |

[51] Int. Cl.$^6$ .................................................. A61B 1/055
[52] U.S. Cl. ........................... 600/176; 600/167; 600/160; 359/434
[58] Field of Search ........................... 600/130, 160, 600/167, 176, 101; 385/902; 359/434, 435, 362, 661, 663, 795, 798

[56] References Cited

U.S. PATENT DOCUMENTS

| 723,790 | 3/1903 | Wappler | 600/167 |
| 1,509,041 | 9/1924 | Hyams | 600/167 |
| 1,764,870 | 6/1930 | Hartinger | 600/160 |
| 1,848,788 | 3/1932 | Loeck | 359/434 |
| 2,102,274 | 12/1937 | Larimore | 600/176 |
| 3,675,984 | 7/1972 | Vulmiere et al. | 600/160 |
| 3,900,021 | 8/1975 | Makepeace et al. | 600/112 |
| 4,708,444 | 11/1987 | Tsuji . | |
| 4,784,118 | 11/1988 | Fantone et al. . | |
| 4,964,686 | 10/1990 | Kato . | |
| 4,964,710 | 10/1990 | Leiner . | |
| 5,142,410 | 8/1992 | Ono et al. . | |
| 5,263,110 | 11/1993 | Anderson | 359/435 |

FOREIGN PATENT DOCUMENTS 93-15647  8/1993  WIPO .

*Primary Examiner*—John P. Leubecker
*Attorney, Agent, or Firm*—Pillsbury Madison & Sutro LLP

[57]  ABSTRACT

A non-flexible endoscope comprising a slender insert section which is to be inserted from a leading end thereof into cavities of living bodies and the like for observing interiors thereof, and comprises an observation optical system consisting only of an objective lens system for forming a primary image in the vicinity of an end opposite to the leading end. The non-flexible endoscope comprises an optical system which is composed of a small number of lens elements and is bright, and can be manufactured at a low cost.

7 Claims, 45 Drawing Sheets

FIG. 20
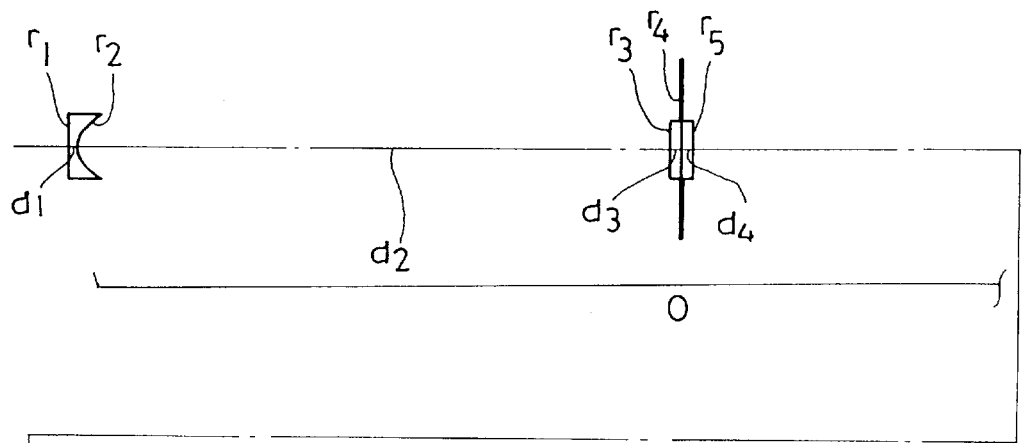
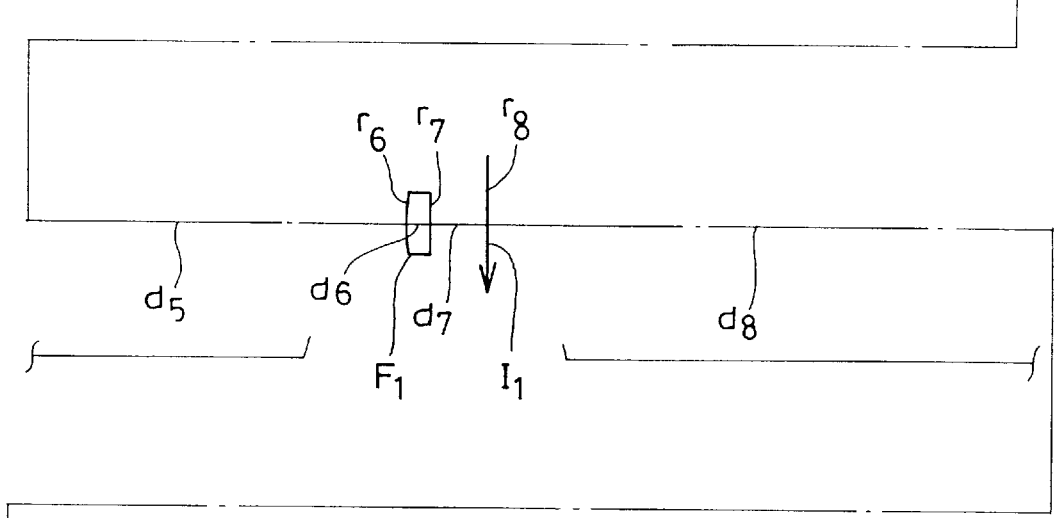
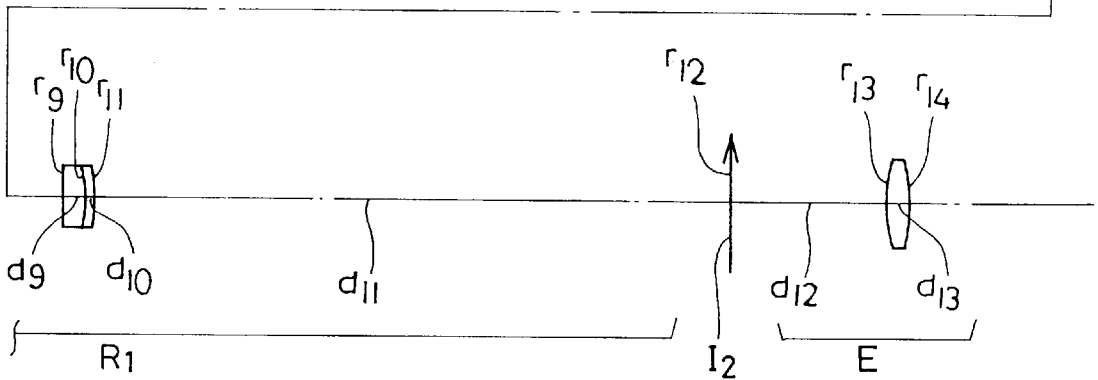

FIG. 42
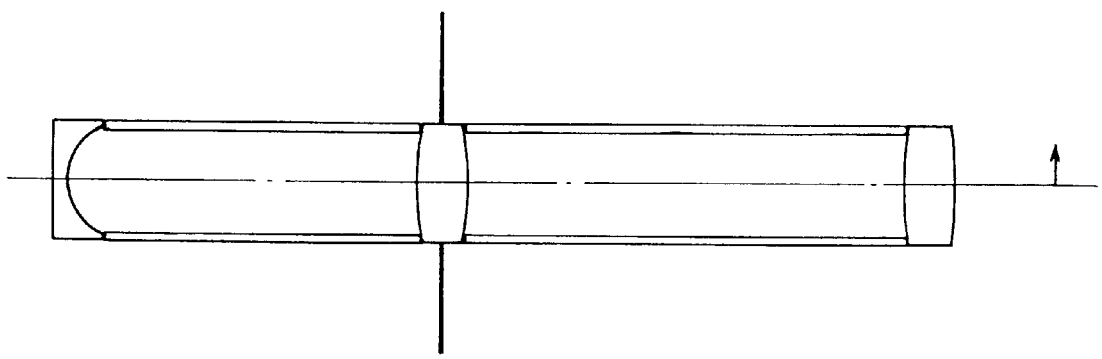
FIG. 43A   FIG. 43B
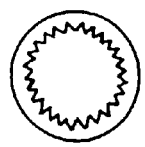 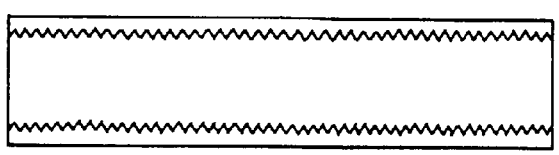

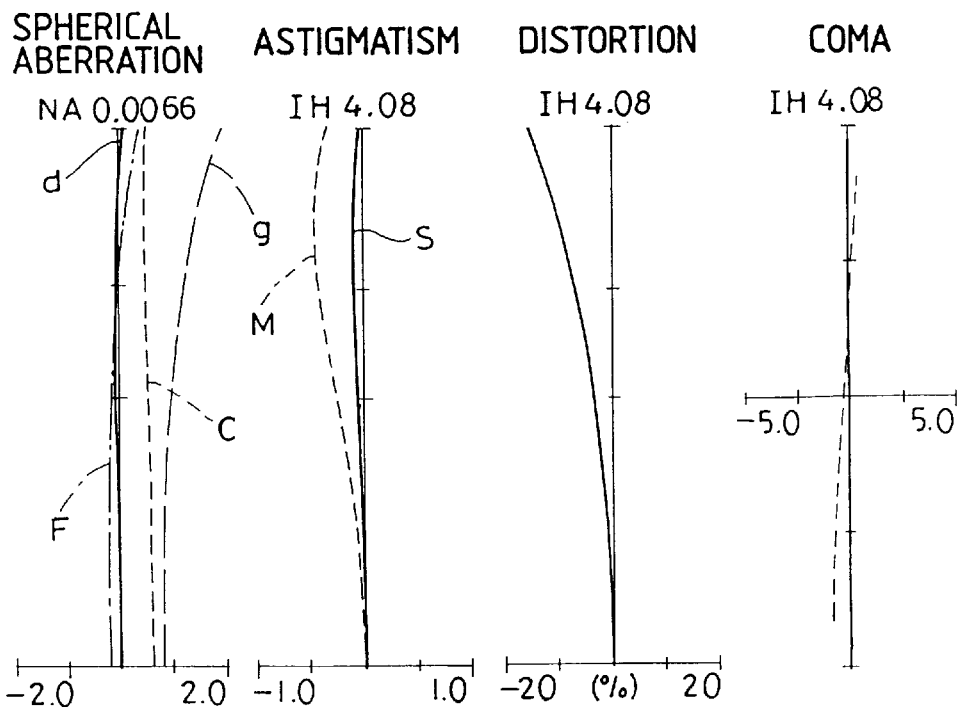
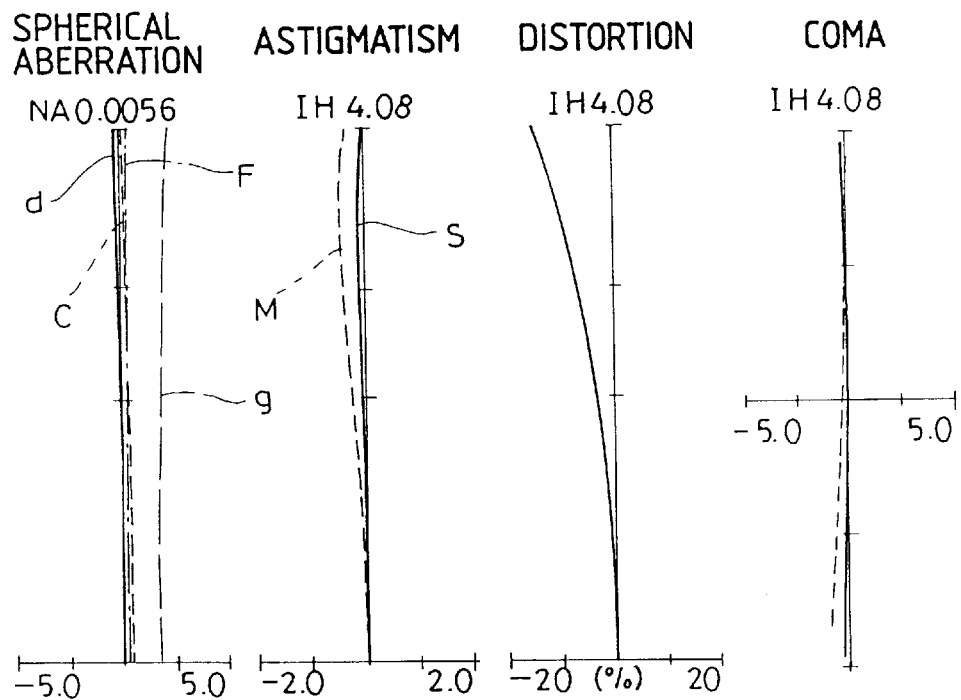

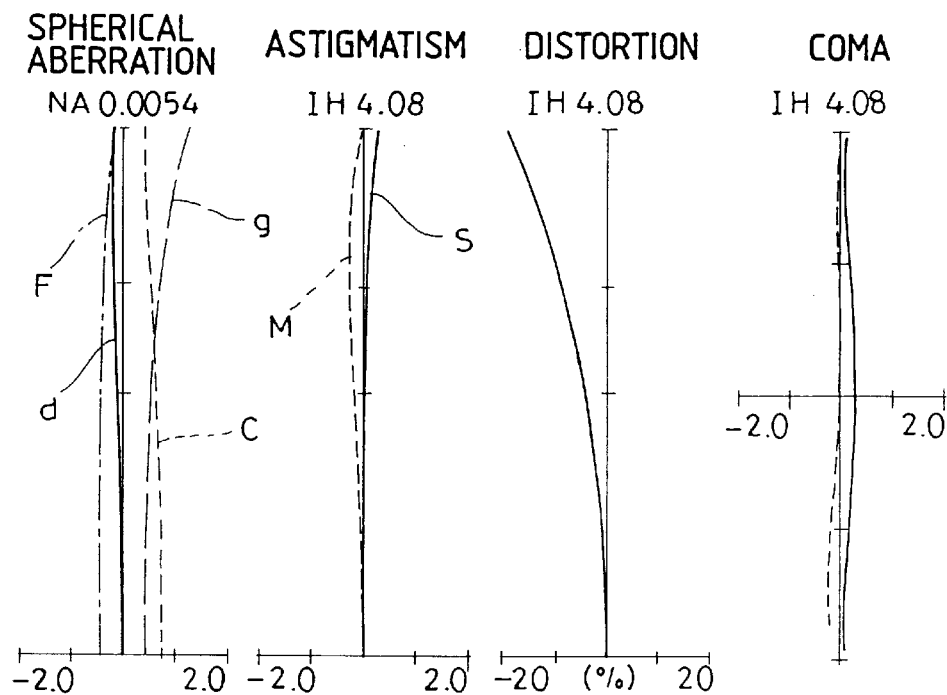
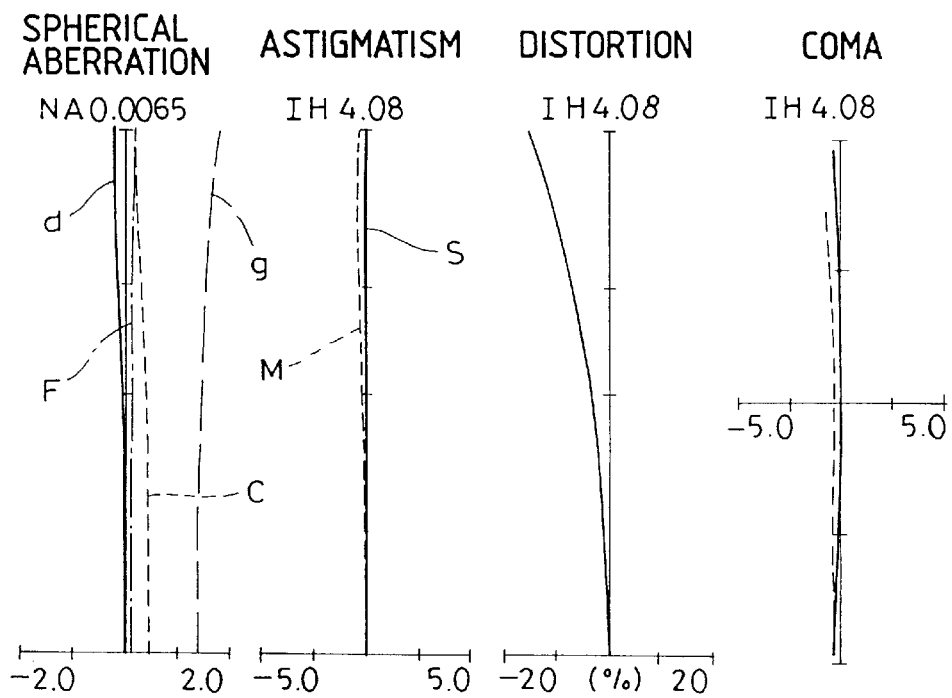

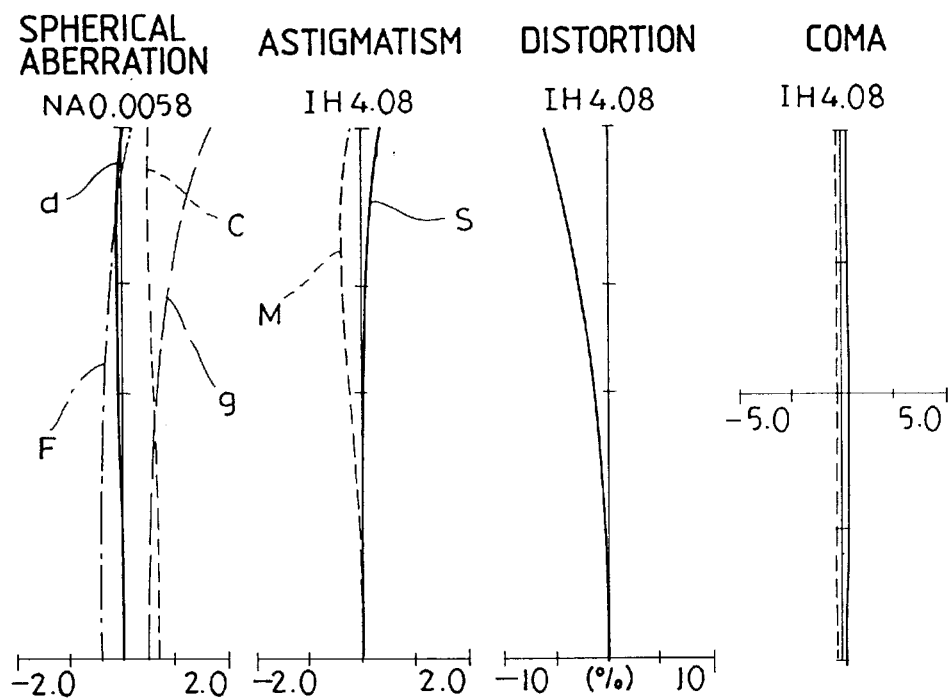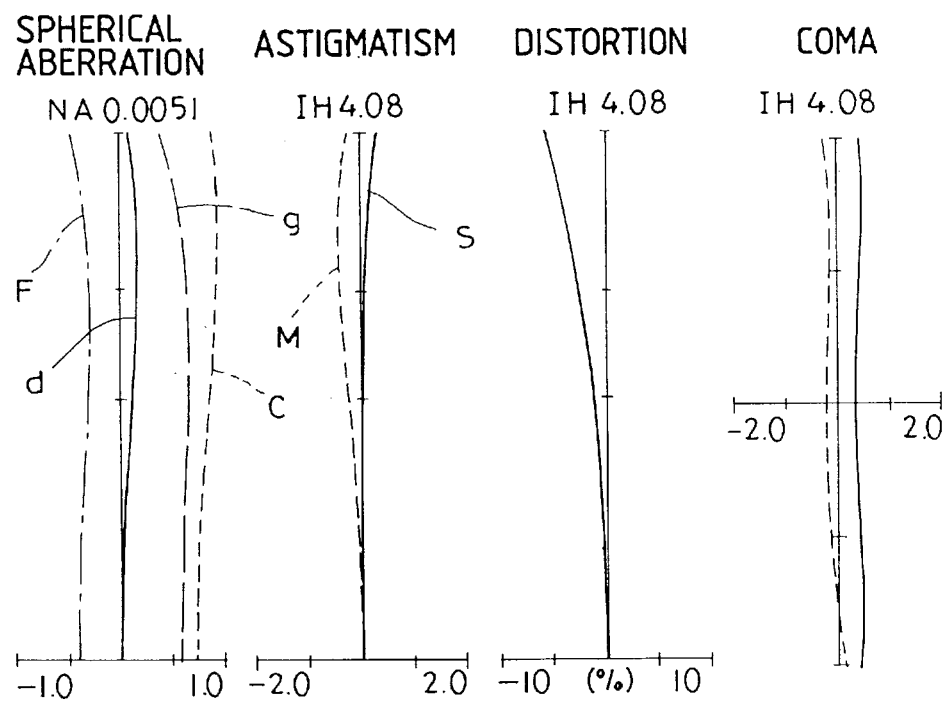

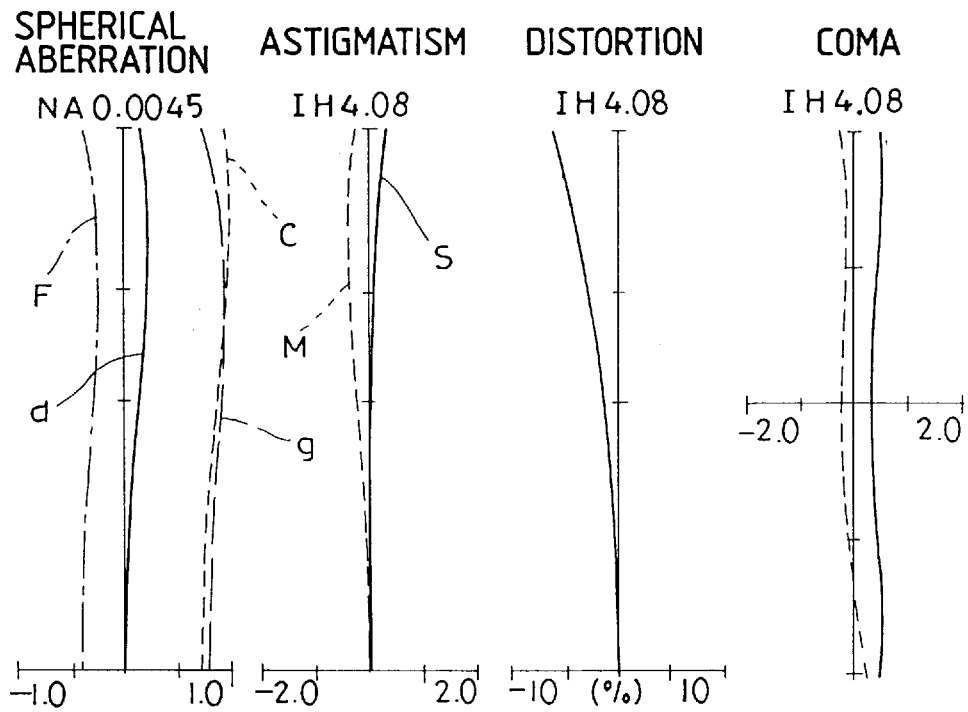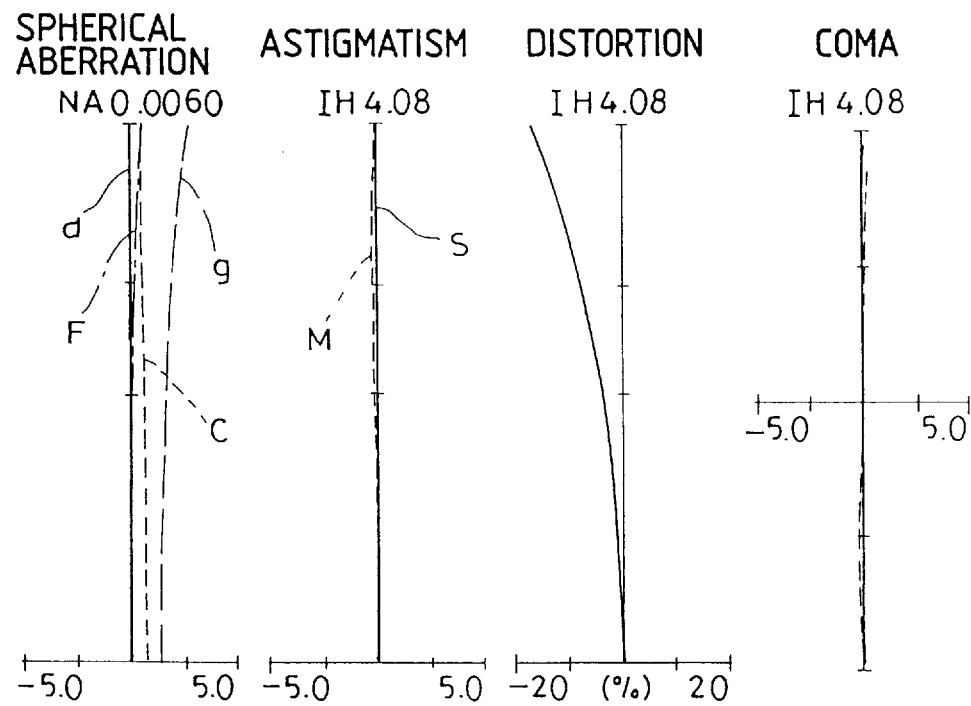

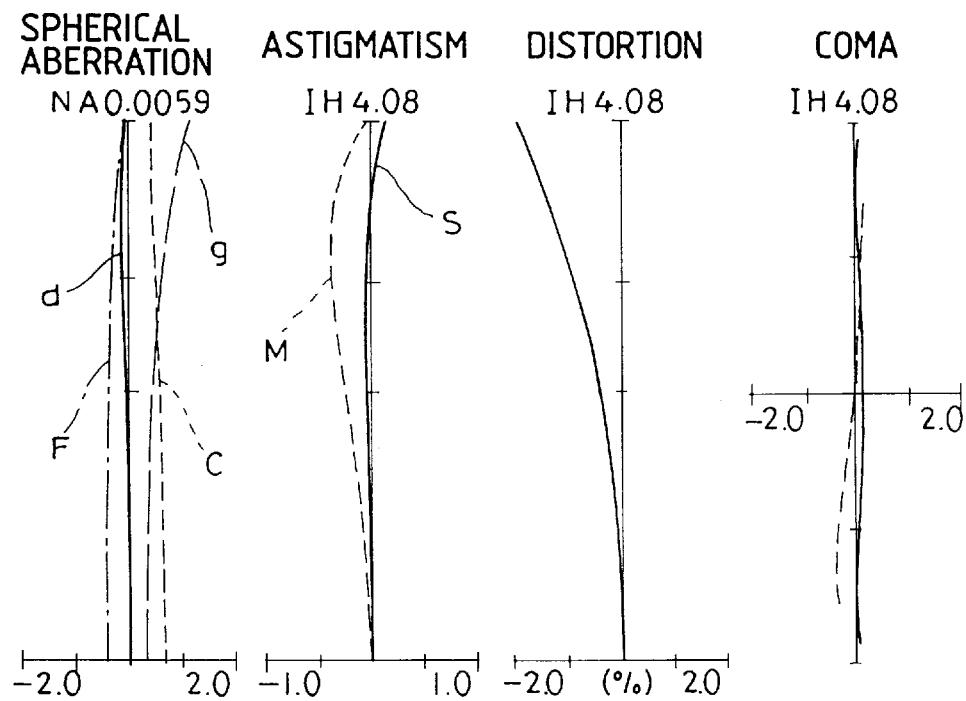
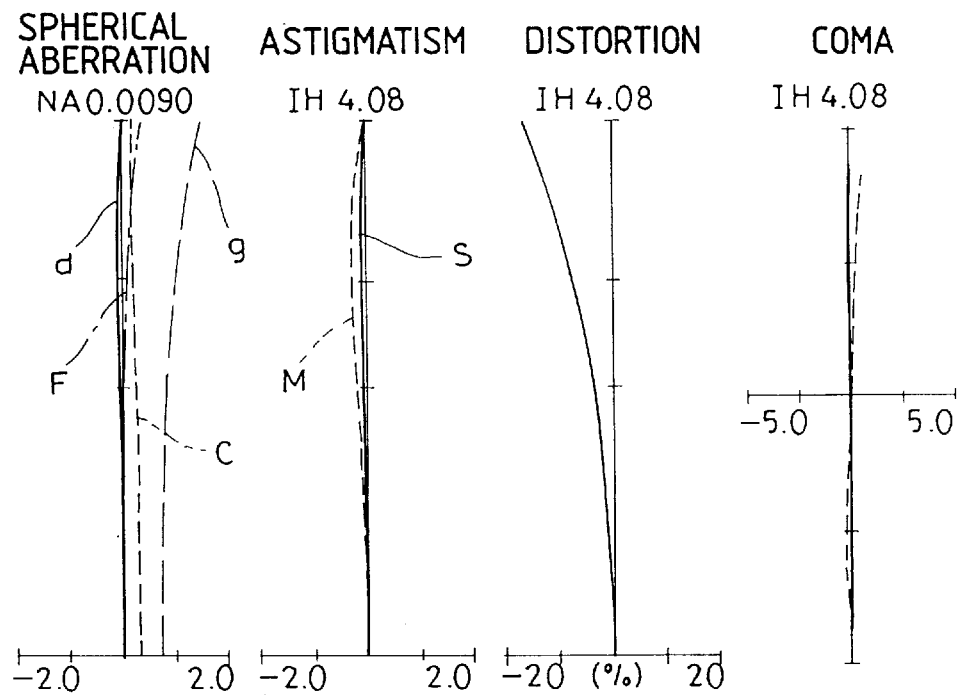

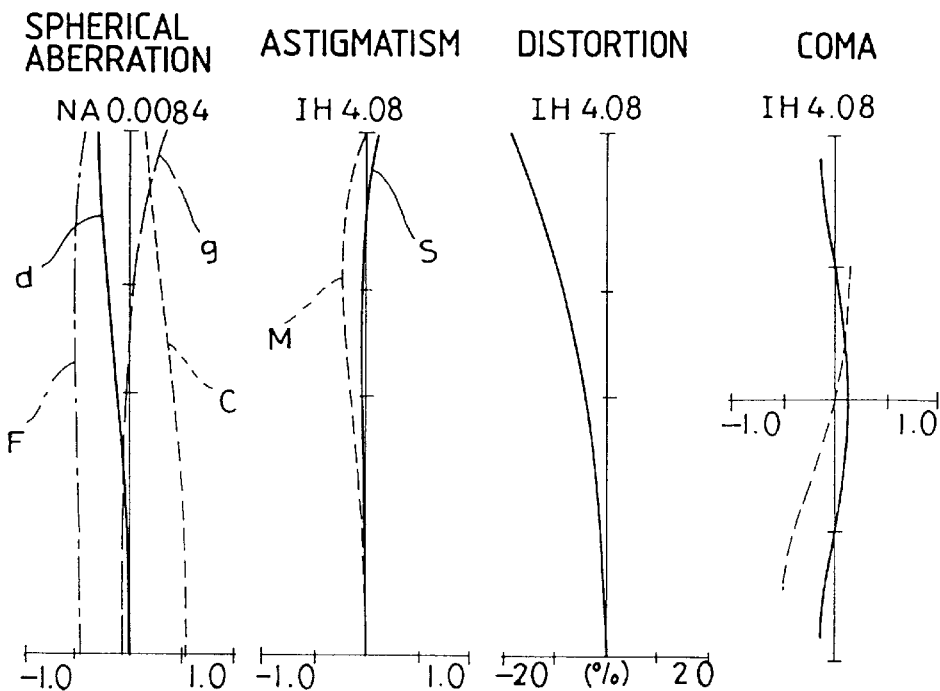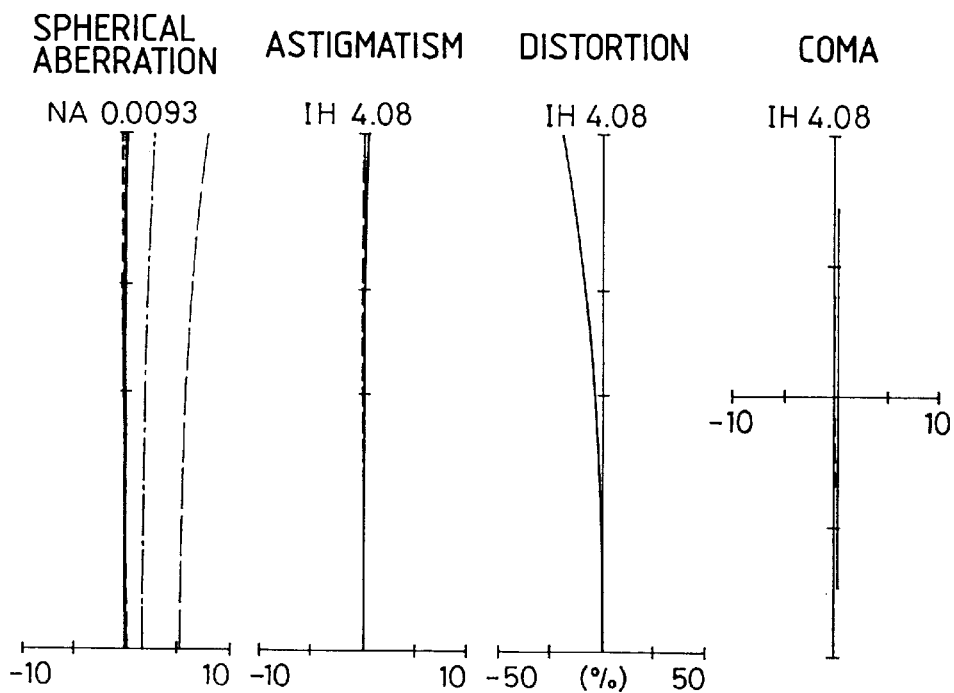

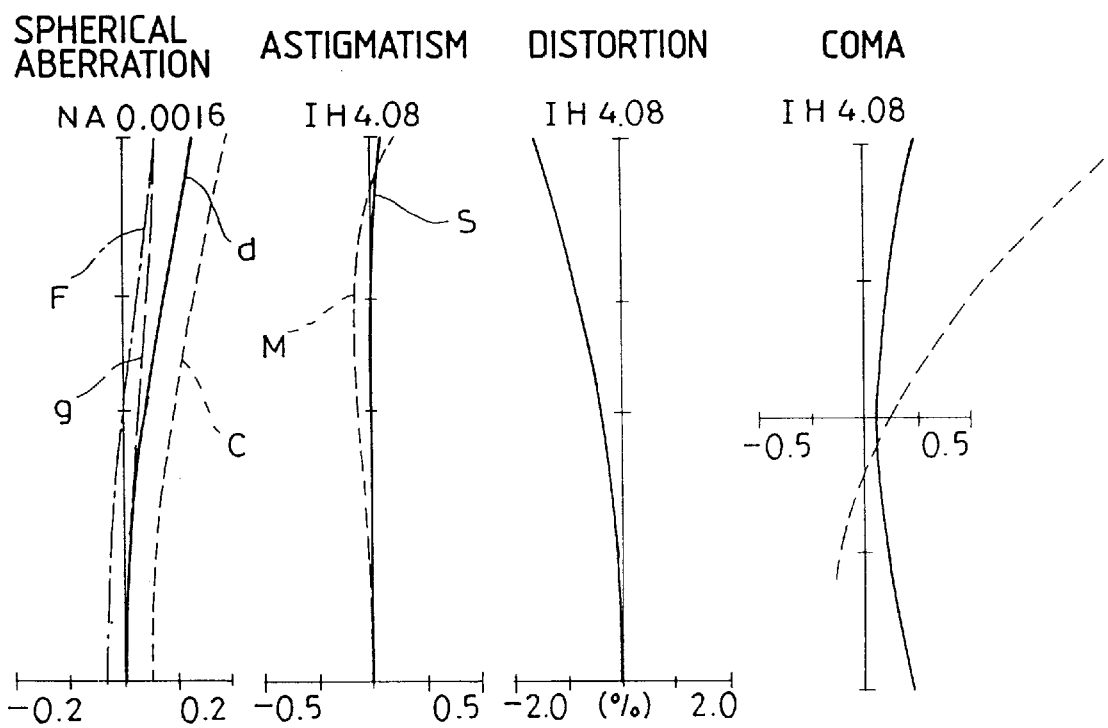

NON-FLEXIBLE ENDOSCOPE HAVING A SLENDER INSERT SECTION

This is a division of application Ser. No. 08/396,428, filed Feb. 28, 1995, and now U.S. Pat. No. 5,632,718.

BACKGROUND OF THE INVENTION a) Field of the Invention

The present invention relates to a non-flexible endoscope to be used widely in the medical field, and mainly a non-flexible endoscope which can be manufactured at a cost low enough to be disposable.

b) Description of the Prior Art

In the recent trend of surgical operations in the medical field, medical techniques are exercised increasingly in conditions of minimum contacts with higher parasites by using endoscopes and treating tools developed exclusively for operations in such conditions. Since affected parts which conventionally required laparotomy for medical treatments can now be treated in the conditions of minimum contacts with the higher parasites under observation through endoscopes for lessening burdens of patients by reducing days of hospitalization, etc., further development is expected for the surgical operations under observation through endoscopes.

Dependently on structures of insert sections of endoscopes which are to be inserted into body cavities, the endoscopes are classified into two types: flexible endoscopes and non-flexible endoscopes. Out of these two types, the non-flexible endoscopes which provide images of higher qualities are used for surgical operations under observation. The non-flexible endoscopes has another merit that they are bearable of autoclaving.

In the recent days where a serious problem is posed by hospital infections, it is remarkably important to sterilize medical tools and instruments, and autoclaving apparatuses are more widespread than the other types of sterilizers. It is therefore necessary to configure the endoscopes so as to have structures bearable of autoclaving.

For the non-flexible endoscopes which have no flexible section, it is rather easy to select materials and structures which are bearable of autoclaving. It is therefore general in practice to repeatedly use non-flexible endoscopes bearable of autoclaving while sterilizing these instruments after individual uses.

On the other hand, attempts are made to configure the non-flexible endoscopes themselves so as to be disposable for preventing hospital infections from being caused through repeated use of the non-flexible endoscopes. In order to configure the non-flexible endoscopes so as to be disposable, it is necessary to configure them so that they can be manufactured as low costs while maintaining practical utilities thereof.

FIG. 1 shows a conventional non-flexible endoscope and an observation optical system used therein. The conventional optical system of this conventional non-flexible endoscope consists of a short objective lens system O disposed in a leading end of an insert section 1 to be inserted into body cavities and a relay lens system R disposed in the insert section 1 almost over the entire length thereof, and an eyepiece lens system E disposed in a grip section 2: these lens systems being integrated with one another in a main body of the non-flexible endoscope.

This conventional non-flexible endoscope is configured so as to permit observing, through the eyepiece lens system E, an image which is formed by the objective lens system O and relayed ordinarily in three cycles by the relay lens system R. This relay lens system consists of fundamental lens units each being symmetrical with regard to a vertical axis perpendicular to the right-to-left direction and is configured so as to relay an image in a plurality of cycles.

It is for the purpose of obtaining required brightness in an optical system that an image is relayed in a plurality of cycles in the optical system for the non-flexible endoscopes such as the conventional example described above.

Since insert sections of non-flexible endoscopes have small outside diameters and large effective lengths, it is necessary for maintaining brightness of images transmitted through the insert sections to enlarge numerical apertures of relay lens systems by increasing numbers of relay cycles. In case of an optical system which uses an insert section having a given effective length in combination with a relay lens system having a given fundamental composition and a given outside diameter, a numerical aperture of the relay lens system is determined dependently on a length required for a single relay cycle and therefore proportional to a number of relay cycles to be performed by the relay lens systems.

The conventional non-flexible endoscope shown in FIG. 1 hardly allows the main body thereof to be disposable due to a fact that the relay lens system R used for composing the optical system thereof comprises a large number of lens elements and the optical system requires too high a manufacturing cost. When the manufacturing cost of the optical system is reduced simply by reducing the number of relay cycles or the number of the lens elements disposed in the relay lens system as a whole, the length required for a single relay cycle is shortened, thereby reducing the numerical aperture of the relay lens system.

For the reason described above, the optical system for the conventional non-flexible endoscope does not allow to lower the manufacturing cost thereof while reserving the brightness required therein.

SUMMARY OF THE INVENTION

A primary object of the present invention is to provide a non-flexible endoscope using an optical system which comprises an extremely small number of lens elements to be discarded, or is configured so as to prevent an operating cost thereof from being enhanced by discarding the lens elements.

Another object of the present invention is to provide a non-flexible endoscope using an optical system which comprises a small number of lens elements, can be manufactured at a low cost and is bright enough for practical use.

A still another object of the present invention is to provide a non-flexible endoscope using an optical system which has a numerical aperture of brightness enlarged or enhanced by prolonging an objective lens system so as to shorten a distance for transmission of an image through a relay lens system.

The non-flexible endoscope according to the present invention has a far end (an end farthest from an observer) and a near end (an end nearest the observer), and comprises an insert section which is used for inserting the far end of the non-flexible endoscope into body cavities to be observed and an eyepiece section which is to be connected to a near end of the insert section. The insert section accommodates an objective lens system, whereas the eyepiece section accommodates an eyepiece lens system which directly receives rays from a primary image formed by the objective lens system and allows these rays to emerge therefrom as rays nearly in parallel with one another. The insert section and the eyepiece section are attachable and detachable to and from each other.

In an optical system which is to be used in the non-flexible endoscope according to the present invention, the objective lens system consists of a first negative lens component and a second positive lens component which has a magnification satisfying the following condition (1):

$$0.7<|\beta_2|<1.5 \tag{1}$$

wherein the reference symbol $\beta_2$ represents the magnification of the second lens component.

Further, it is desirable that the objective lens system forms a primary image at a position located in the vicinity of the near end of the insertion section, or satisfies the following condition (2):

$$0.7<D_1/D_e<1.5 \tag{2}$$

wherein the reference symbol $D_1$ represents a distance as measured from a first surface of the objective lens system to the primary image and the reference symbol $D_e$ designates an effective length of the insert section. Meant by "an effective length of the insert section" is a length of a section which has a small outside diameter and is to be inserted into a truncal or a sheath.

Further, it is desirable for correction of chromatic aberration to configure the objective lens system so as to satisfy the following condition (3):

$$n_1>n_2, \nu_1<\nu_2 \tag{3}$$

wherein the reference symbols $n_1$ and $n_2$ represent refractive indices of the first lens component and the second lens component respectively, and the reference symbols $\nu_1$ and $\nu_2$ designate Abbe's numbers of the first lens component and the second lens component respectively.

Furthermore, it is desirable to compose the first lens component of the objective lens system of a single plano-convex lens element, and configure the second lens component as a cemented lens component which consists of a positive lens element and a negative lens element, and satisfies the following condition (4):

$$n_p<n_N, \nu_p>\nu_N \tag{4}$$

wherein the reference symbols $n_p$ and $n_N$ represent refractive indices of the positive lens element and the negative lens element respectively of the second lens component, and the reference symbol $\nu_p$ and $\nu_N$ designate Abbe's numbers of the positive lens element and the negative lens element respectively of the second lens component.

Moreover, the non-flexible endoscope according to the present invention consists of a slender insertion section which is to be inserted into cavities of living bodies for observing these cavities and a grip section which is to be kept outside the cavities: and comprises an optical system which consists of an objective lens system disposed on the side of the leading end in the insert section for forming primary image in the insert section, a relay lens system disposed in the insert section for relaying the primary image for forming a secondary image at a near end (an end located on the side opposite to the leading end) of the insert section or in the grip section and an eyepiece lens system disposed in the grip section for deflecting rays coming from the secondary image so as to be parallel with one another or in an observable condition; and is configured so as to satisfy the following condition (5):

$$0.3<D_1/D_2<0.7 \tag{5}$$

wherein the reference symbol $D_2$ represents a distance as measured from a first surface to the secondary image.

Moreover, it is desirable that an optical system which is to be used in the non-flexible endoscope according to the present invention (an optical system of a type comprising a relay lens system) adopts an objective lens system composed of a first lens component consisting only of a single negative lens element and a second lens component consisting only of a positive lens element which satisfies the following condition (6):

$$0.5<|\beta_2|<2.0 \tag{6}$$

wherein the reference symbol $\beta_2$ represents a magnification of the second lens component.

For the optical system of the non-flexible endoscope according to the present invention of the type which comprises the relay lens system as described above, it is desirable to dispose a primary field lens component in the vicinity of the primary image at a location satisfying the following condition (7):

$$|D_3/D_2|\leq 0.1 \tag{7}$$

wherein the reference symbol $D_3$ represents a spacing to be reserved between the primary image and the field lens component.

Moreover, it is desirable to control the relay lens system so as to have a magnification $\beta_R$ satisfying the following condition (8):

$$-2<\beta_R<-0.5 \tag{8}$$

In addition, when the optical system of the non-flexible endoscope according to the present invention is of a type which uses a relay lens system configured so as to perform a single cycle of image relaying or a plurality of cycles of image relaying, it is desirable for shortening the relay lens system to satisfy the following condition (9):

$$0.3<D_1/D_R<2.0 \tag{9}$$

wherein the reference symbol $D_R$ represents a distance required for a single cycle of image relaying.

BRIEF DESCRIPTION OF THE DRAWINGS

FIG. 20 shows a sectional view illustrating a composition of an eleventh embodiment of the non-flexible endoscope according to the present invention;

FIG. 42 shows a sectional view illustrating a composition of an objective lens system which is to be used in combination with a relay lens system performing five cycles of image relaying;

FIG. 43A and FIG. 43B show sectional views illustrating a spacing tube to be used in the non-flexible endoscope according to the present invention;

FIG. 48A, FIG. 48B, FIG. 48C and FIG. 48D show curves visualizing aberration characteristics of an optical system used in the fifth embodiment of the non-flexible endoscope according to the present invention;

FIG. 49A, FIG. 49B, FIG. 49C and FIG. 49D show curves visualizing aberration characteristics of an optical system used in the sixth embodiment of the non-flexible endoscope according to the present invention;

FIG. 50A, FIG. 50B, FIG. 50C and FIG. 50D show curves visualizing aberration characteristics of an optical system used in the seventh embodiment of the non-flexible endoscope according to the present invention;

FIG. 51A, FIG. 51B, FIG. 51C and FIG. 51D show graphs illustrating aberration characteristics of an optical system used in the eighth embodiment of the non-flexible endoscope according to the present invention;

FIG. 54A, FIG. 54B, FIG. 54C and FIG. 54D show curves illustrating aberration characteristics of an optical system used in the eleventh embodiment of the non-flexible endoscope according to the present invention;

FIG. 55A, FIG. 55B, FIG. 55C and FIG. 55D show curves illustrating aberration characteristics of an optical system used in the twelfth embodiment of the non-flexible endoscope according to the present invention;

FIG. 56A, FIG. 56B, FIG. 56C and FIG. 56D show graphs visualizing aberration characteristics of an optical system employed in the thirteenth embodiment of the non-flexible endoscope according to the present invention;

FIG. 57A, FIG. 57B, FIG. 57C and FIG. 57D show graphs visualizing aberration characteristics of an optical system employed in the fourteenth embodiment of the non-flexible endoscope according to the present invention;

FIG. 58A, FIG. 58B, FIG. 58C and FIG. 58D show graphs visualizing aberration characteristics of an optical system employed in the fifteenth embodiment of the non-flexible endoscope according to the present invention;

FIG. 59A, FIG. 59B, FIG. 59C and FIG. 59D show graphs visualizing aberration characteristics of an optical system employed in the sixteenth embodiment of the non-flexible endoscope according to the present invention;

FIG. 60A, FIG. 60B, FIG. 60C and FIG. 60D show graphs visualizing aberration characteristics of an optical system employed in the seventeenth embodiment of the non-flexible endoscope according to the present invention;

FIG. 61A, FIG. 61B, FIG. 61C and FIG. 61D show curves illustrating aberration characteristics of an optical system used in the eighteenth embodiment of the non-flexible endoscope according to the present invention; and FIG. 62A, FIG. 62B, FIG. 62C and FIG. 62D show graphs illustrating aberration characteristics of an imaging lens system to be used in the optical systems of the non-flexible endoscope according to the present invention.

DETAILED DESCRIPTION OF THE PREFERRED EMBODIMENTS

Now, the non-flexible endoscope according to the present invention will be described more detailedly below with reference to the preferred embodiments illustrated in the accompanying drawings.

Figure 2:
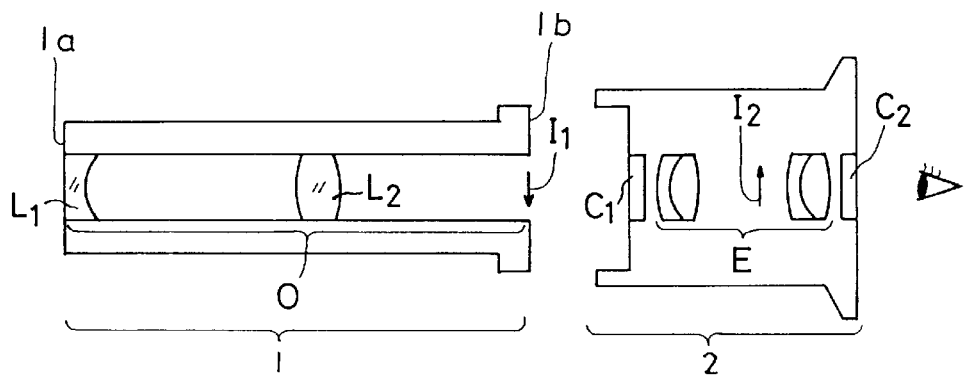
FIG. 2 shows a sectional view illustrating a configuration of the non-flexible endoscope according to the present invention.

FIG. 2 shows an embodiment of the non-flexible endoscope according to the present invention. In this drawing, the reference numeral 1 represents a cylindrical insert section which has a far end 1a and a near end 1b, and accommodates an objective lens system O. Further, the reference numeral 2 designates an eyepiece section which is attachable and detachable to and from the near end 1b of the insert section 1, and accommodates an eyepiece lens system E. The reference symbols $C_1$ and $C_2$ denote cover glass plates which are disposed before and after the eyepiece lens system E. This non-flexible endoscope is to be inserted, from the side of the far end 1a of the insert section, into a location such as a body cavity or the similar part to be observed so that the objective lens system O forms an image of an object to be observed (image $I_1$) in the vicinity of the near end 1b of the insert section. Rays coming from this image are incident directly, or without passing through a relay lens system, onto the objective lens system disposed in the vicinity of the near end of the insert section and reimaged in the eyepiece lens system E by a front lens component of the eyepiece lens system E (image $I_2$). Rays coming from the image $I_2$ emerge from the eyepiece lens system E as rays nearly in parallel with one another so that an observer can receive these rays or observe an image of the object.

Figure 3:
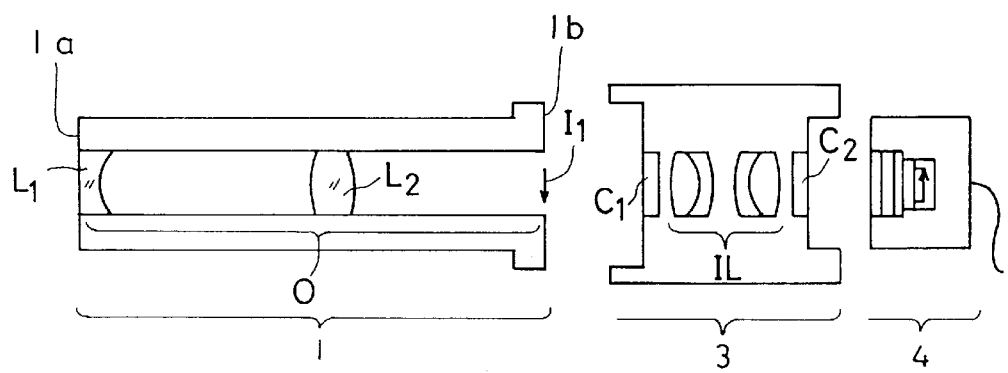
FIG. 3 shows a sectional view illustrating another example of the non-flexible endoscope according to the present invention.

FIG. 3 shows a non-flexible endoscope which is used for TV monitoring and uses an insert section 1 having the same composition as that of the insert section 1 shown in FIG. 2, but can be equipped with an adaptor 3 for use in an imaging device, such as a TV camera adaptor, and an imaging device 4, such as a TV camera and a photographing camera, in place of the eyepiece section 2 shown in FIG. 2. The TV camera adaptor 3 comprises an imaging lens system IL, whereas the TV camera 4 comprises an image pickup means such as a solid-state image pickup device. An objective lens system O forms an image of an object in the vicinity of a near end 1b of the insert section (image $I_1$). Rays coming from this image are incident directly, or without passing through a relay lens system, on the imaging lens system IL disposed in the TV camera adaptor 3, which reimages an image of an object on a solid-state image pickup device disposed in the TV camera 4. This image is presented on a display means such as a TV monitor for observation. In addition, the TV camera adaptor 3 and the TV camera 4 are attachable and detachable to and from each other.

Since the insert section 1 of the non-flexible endoscope shown in FIG. 2 or FIG. 3 can be detached from the eyepiece section 2 or the TV camera adaptor 3, the insert section 1 can be discarded after it is practically used and contaminated. Further, the eyepiece section 2 or the TV camera adaptor 3 and the TV camera 4 can be reused in combination with a new insert section.

Figure 4:
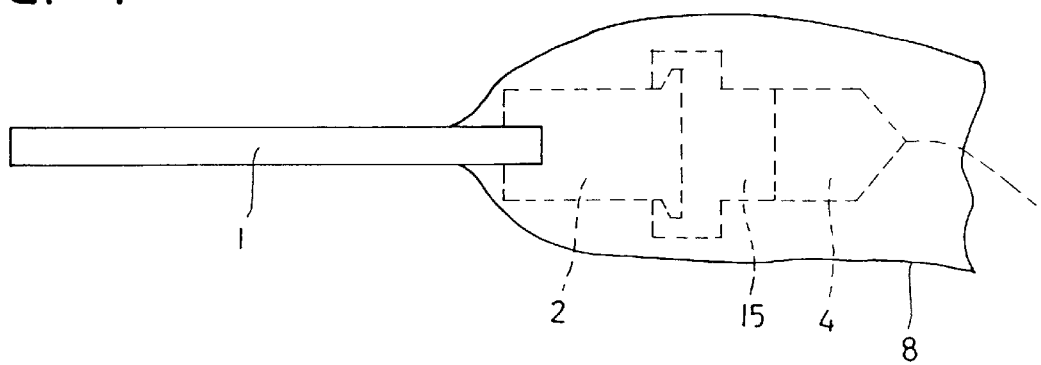
FIG. 4 shows a sectional view illustrating a configuration of the non-flexible endoscope shown in FIG. 3 when it is protected with a sterilizing cover.

The non-flexible endoscope shown in FIG. 2 or FIG. 3 allows the eyepiece section or the TV camera adaptor and the TV camera other than the insert section to be covered with a strilizing cover 8 as shown in FIG. 4. The sterilizing cover 8 is integrated at one end thereof with the insert section 1 in FIG. 4. Alternately, the sterilizing cover 8 may be elastically fitted over the insert sectional or fixed to the insert section 1 by an adequate fixing means. The sterilizing cover has a large opening at the other end.

When the sterilizing cover 8 is integrated with the insert section 1, the eyepiece section or the TV camera adaptor, etc. can be protected with the sterilizing cover 8 by inserting the eyepiece section or the TV camera adaptor, etc. through the opening located at the other end and connecting the TV camera adaptor or the TV camera adaptor, etc. to the insert section 1. When the sterilizing cover 8 is separate from the insertion section 1, it is connected to the eyepiece section or the TV camera adaptor, etc., and then the sterilizing cover 8 is placed on the near end of the insert section 1 so as to cover the eyepiece section or the TV camera adaptor, etc. for maintenance in cleaner conditions. In FIG. 4, the reference numeral 2 represents the eyepiece section shown in FIG. 2, and the reference numeral designates an adaptor for TV photographing which is detachable from the eyepiece section 2 and accommodates an imaging lens system for imaging nearly parallel rays emerging from an eyepiece lens system. A TV camera 4 shown in FIG. 4 is quite the same as that illustrated in FIG. 3.

Now, an optical system to be used in the non-flexible endoscope according to teh present invention will be described detailedly below:

First, description will be made of an objective lens system to be disposed in the optical system. The objective lens system to be used in the non-flexible endoscope according to the present invention is long enough to extend almost over the entire length of the insertion section 1 and therefore has a composition which is largely different from that of an ordinary objective lens system for non-flexible endoscopes (an objective lens system for non-flexible endoscopes which uses a relay lens system for transmitting an image).

The objective lens system to be used in the non-flexible endoscope according to the present invention consists of a first lens component $L_1$ which is disposed in the vicinity of a far end 1a of an insert section 1 and has a negative refractive power, and a second lens component $L_2$ which is disposed at a middle location in the insert section 1 and has a positive refractive power.

Figure 5A:
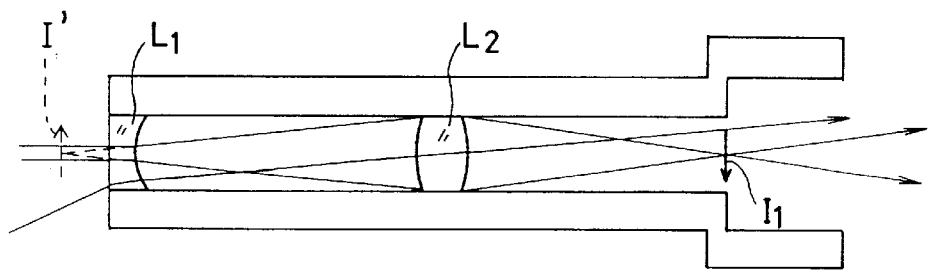
FIG. 5A, FIG. 5B and FIG. 5C show diagrams illustrating relationship between locations of lens components in an objective lens system to be used in the non-flexible endoscope according to the present invention and those of primary images to be formed by the objective lens systems.
Figure 5B:
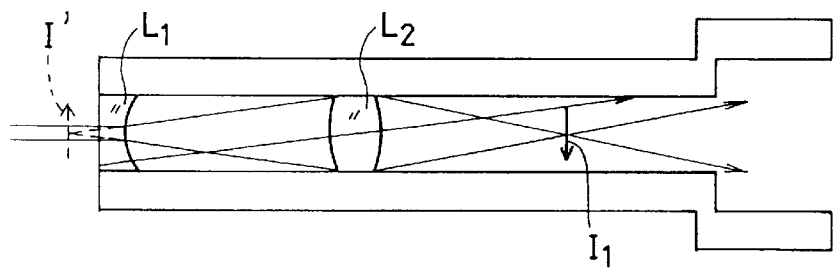
Figure 5C:
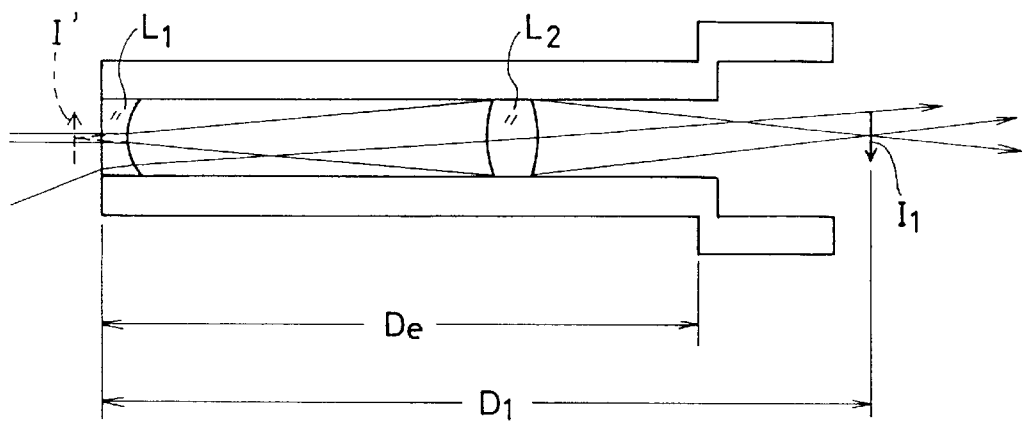

In the objective lens system having the composition described above, the first lens component $L_1$ forms, in the vicinity of the far end 1a of the insert section 1, a virtual image I' which is contracted on the order of an outside diameter of this lens component or smaller and the second lens component $L_2$ reimages the virtual image I' so as to form a primary image $I_1$ in the vicinity of the near end 1b of the insert section 1. When the objective lens system comprises no aperture stop, a margin (a side surface) of the second lens component $L_2$ or a portion of a lens barrel functions as an aperture stop. When the first lens component $L_1$ is not disposed in the vicinity of the far end 1a and does not have a negative refractive power as shown in FIG. 5A, it will undesirably hinder offaxial rays from passing through a pipe of the insert section. When the second lens component $L_2$ does not have a positive refractive power, it can hardly reimage the virtual image I' or when the second lens component $L_2$ is not disposed in the middle section of the insertion section 1, brightness will be undesirably lowered due to eclipse of the offaxial rays or reduction of a numerical aperture.

Further, it is desirable that the second lens component $L_2$ satisfies the above-mentioned condition (1).

If $|\beta_2|$ exceeds the lower limit of 0.7 of the condition (1), a light bundle obtained on the object side will undesirably be thin, thereby lowering brightness in the optical system. If $|\beta_2|$ exceeds the upper limit of 1.5 of the condition (1), in contrast, the offaxial rays will be undesirably eclipsed, thereby producing eclipse of an image.

Further, it is desirable that the objective lens system forms the primary image in the vicinity of the near end 1b of the insert section 1. For this reason, it is desirable to configure the objective lens system so as to satisfy the above-mentioned condition (2).

If $D_1/D_e$ has a value smaller than the lower limit of 0.7 of the condition (2), the primary image $I_1$ will be formed in the pipe of the insert section 1, whereby the offaxial rays will be eclipsed. If $D_1/D_e$ has a value exceeding the upper limit of 1.5 of the condition (2), in contrast, the light bundle obtained on the object side will be thin and the objective lens system will have a small numerical aperture, thereby lowering brightness in the optical system.

For the objective lens system to be used in the non-flexible endoscope according to the present invention, it is desirable to compose the first lens component $L_1$ and the second lens component $L_2$ of small numbers of lens elements or select simple compositions for these lens components so that the insert section can be manufactured at a low cost. For this reason and for suppression of offaxial aberrations, it is desirable to compose the first lens component $L_1$ of a single negative lens element having a concave surface on the image side. Further, it is more desirable to configure this negative lens element so as to have a planar surface on the object side. Furthermore, it is desirable to configure the second lens component $L_2$ as a positive lens component consisting of a single positive lens element or a positive cemented lens component. The lens elements may be made of a glass material or a plastic material.

Figure 6A:
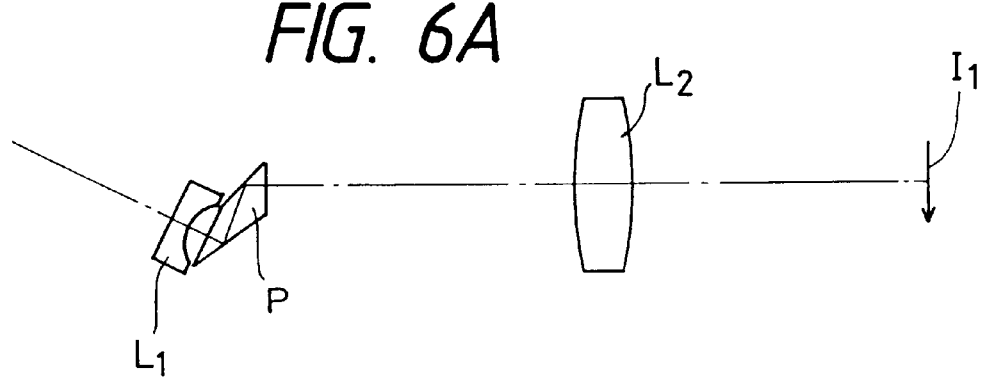
FIG. 6A and FIG. 6B show sectional views exemplifying prisms for oblique viewing which are to be used in an objective lens system of the optical system of the non-flexible endoscope according to the present invention.
Figure 6B:
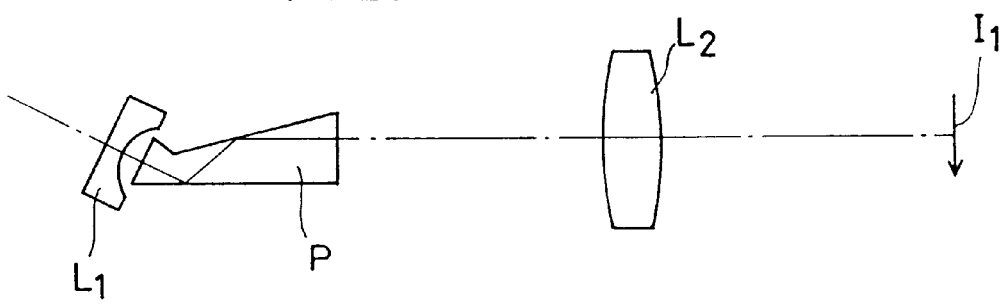

FIG. 6A and FIG. 6B show examples of objective lens systems to be used in the non-flexible endoscope according to the present invention in each of which a visual field changing prism for oblique viewing is disposed in a tip of the objective lens system and composed of a single prism as shown in the drawing. An ordinary visual field changing prism is composed of two or more prisms and requires a high manufacturing cost. For reducing a manufacturing cost of the objective lens system and configuring the insert section which comprises the prism in addition to the objective lens system so as to be disposable, it is desirable to compose the prism P of a single prism and dispose it after the first lens component $L_1$ as shown in FIG. 6A or FIG. 6B.

A first embodiment of the optical system which has the configuration described above for use in the non-flexible endoscope according to the present invention has a composition illustrated in FIG. 8 and numerical data listed below:

Embodiment 1 object distance = −30 (viewing diopter = 1 m$^{-1}$),
NA for incidence = 0.0032,
field angle = 60.2°   image height = 125

$r_1 = \infty$
  $d_1 = 0.8000$    $n_1 = 1.80610$    $\nu_1 = 40.95$
$r_2 = 5.1410$
  $d_2 = 167.5000$
$r_3 = 87.8610$ -continued object distance = −30 (viewing diopter = 1 m$^{-1}$),
NA for incidence = 0.0032,
field angle = 60.2°  image height = 125

|   |   |   |   |
|---|---|---|---|
| | $d_3$ = 2.000 | $n_2$ = 1.51633 | $v_2$ = 64.15 |
| $r_4$ = ∞ (stop) | | | |
| | $d_4$ = 2.0000 | $n_3$ = 1.51633 | $v_3$ = 64.15 |
| $r_5$ = −87.8610 | | | |
| | $d_5$ = 167.6300 | | |
| $r_6$ = ∞ | | | |
| | $d_6$ = 30.0000 | | |
| $r_7$ = 24.6552 | | | |
| | $d_7$ = 3.0000 | $n_4$ = 1.69680 | $v_4$ = 55.52 |
| $r_8$ = −17.2217 | | | |
| | $d_8$ = 1.0000 | $n_5$ = 1.69895 | $v_5$ = 30.12 |
| $r_9$ = −560.9511 | | | |
| | $d_9$ = 40.4125 | | |
| $r_{10}$ = 8.8507 | | | |
| | $d_{10}$ = 3.0000 | $n_6$ = 1.51633 | $v_6$ = 64.15 |
| $r_{11}$ = −5.2344 | | | |
| | $d_{11}$ = 1.0000 | $n_7$ = 1.71736 | $v_7$ = 29.51 |
| $r_{12}$ = 59.7461 | | | |
| | $d_{12}$ = 1.0000 | | |
| $r_{13}$ = 8.8507 | | | |
| | $d_{13}$ = 3.0000 | $n_8$ = 1.51633 | $v_8$ = 64.15 |
| $r_{14}$ = −5.2344 | | | |
| | $d_{14}$ = 1.0000 | $n_9$ = 1.71736 | $v_9$ = 29.51 |
| $r_{15}$ = 59.7461 | | | |
| | $d_{15}$ = 15.5875 | | |
| $r_{16}$ = 23.5293 | | | |
| | $d_{16}$ = 3.0000 | $n_{10}$ = 1.51633 | $v_{10}$ = 64.15 |
| $r_{17}$ = −24.0097 | | | |
| | $d_{17}$ = 8.0000 | | |
| $r_{18}$ = ∞ | | | |
| | $d_{18}$ = 16.2546 | | |
| $r_{19}$ = 21.2180 | | | |
| | $d_{19}$ = 0.9000 | $n_{11}$ = 1.78472 | $v_{11}$ = 25.71 |
| $r_{20}$ = 8.1750 | | | |
| | $d_{20}$ = 2.6000 | $n_{12}$ = 1.66672 | $v_{12}$ = 48.32 |
| $r_{21}$ = −18.7960 | | | |

$D_1$ = 339.6 mm, $D_e$ = 300 mm, $D_1/D_e$ = 1.132, $\beta_2$ = −0.958 wherein the reference symbols $r_1$, $r_2$, . . . represent radii of curvature on surfaces of respective lens elements, the reference symbols $d_1$, $d_2$, . . . designate thicknesses of the respective lens elements and air-spaces reserved therebetween, the reference symbols $n_1$, $n_2$, . . . denote refractive indices of the respective lens elements, and the reference symbols $v_1$, $v_2$, . . . represent Abbe's numbers of the respective lens elements.

In the numerical data listed above, $r_1$ through $r_5$ correspond to the objective lens system, $r_7$ through $r_{21}$ correspond to the eyepiece lens system, $r_4$=∞ represents an imaginary stop, $r_6$=∞ designates the primary image and $r_{18}$=∞ denotes the secondary image.

In the first embodiment of the optical system of the non-flexible endoscope according to the present invention, the objective lens system and the eyepiece lens system are disposed in the insert section and the eyepiece section respectively which are located on both sides of the primary image ($r_6$). Since the first embodiment uses no relay lens system, it comprises lens elements in a remarkably reduced number and the insert section accommodates only the objective lens system which is composed of an extremely small number of lens elements. Further, the optical system composed of the objective lens system and the eyepiece lens system adopted for the first embodiment has aberrations favorably corrected as illustrated in FIG. 46A, FIG. 46B, FIG. 46C and FIG. 46D. In these drawings, diopter is taken as the abscissa for visualizing each of spherical aberration, astigmatism and coma.

Figure 9:
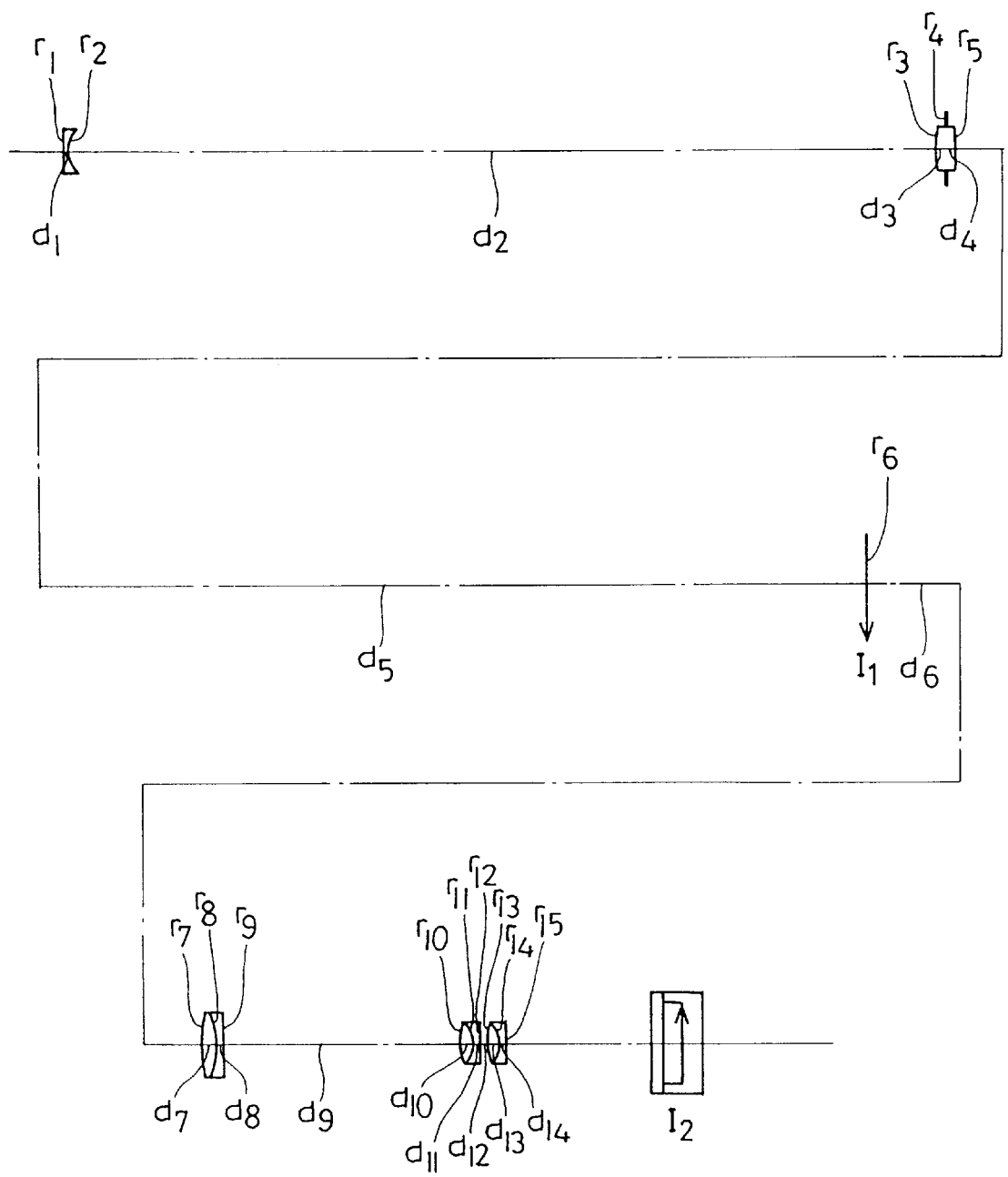
FIG. 9 shows a sectional view illustrating a composition of a second embodiment of the non-flexible endoscope according to the present invention.

FIG. 9 shows a second embodiment of the optical system to be used in the non-flexible endoscope according to the present invention. The second embodiment is configured for use in the non-flexible endoscope according to the present invention which is of the type shown in FIG. 3. The non-flexible endoscope shown in FIG. 3 has the insert section 1 which is to be connected to the TV camera adaptor 3 and further to the TV camera 4 as described above, and permits detaching the insert section 1 for discarding it after use. The TV camera adaptor and the TV camera may be integrated with each other so as to compose a TV camera comprising an imaging lens system so that the insert section 1 can be detachably connected to the TV camera and detached from the TV camera for discarding after use.

Each of the first embodiment and the second embodiment described above is configured on an assumption that the objective lens system is composed of the first lens component and the second lens component which consist of a single plano-concave lens element and a single biconvex lens element respectively made of multi-component type glass materials. The second biconvex lens element adopted as the second lens component is a symmetrical lens element which has the same radius of curvature on both surfaces thereof and requires no discrimination between a front surface and a rear surface thereof at an assembly stage thereof. Even when an asymmetrical lens element such as a plano-convex lens element is used as the second lens component and disposed mistaking its front surface for its rear surface, however, no serious problem is posed by variations of aberrations since the second lens component has a magnification nearly equal to 1x and functions also as an aperture stop. Accordingly, the second lens component requires nearly no consideration for its direction even when it has an asymmetrical shape.

In each of the first embodiment and the second embodiment, the plano-concave lens element used as the first lens component is made of a glass material which has a high refractive index and a medium dispersing power, whereas the biconvex lens element adopted as the second lens component is made of a glass material which has a low refractive index and a low dispersing power. In other words, the objective lens system is configured so as to satisfy the following condition (3):

$$n_1 > n_2, v_1 < v_2 \tag{3}$$

wherein the reference symbols $n_1$ and $n_2$ represent refractive indices of the first lens component and the second lens component respectively, and the reference symbols $v_1$ and $v_2$ designate Abbe's number of the first lens component and the second lens component respectively.

For the first lens component, it is suitable to select a glass material having a high refractive index for obtaining a low curvature on the concave surface thereof and a dispersing power which is not too strong to suppress lateral chromatic aberration. Further, for the second lens component which is composed of a single lens element, it is unnecessary to select a glass material which has an exceptionally low refractive index, but a glass material having a low dispersing power should desirably be selected for suppressing production of longitudinal chromatic aberration.

The second embodiment of the optical system for non-flexible endoscope which consists of the objective lens system and the imaging lens system has the numerical data which are listed below:

Embodiment 2

| object distance = −30, NA for incidence = 0.0033 (F number = 28.574) field angle = 61.3° image height = 3.27 | | | |
|---|---|---|---|
| $r_1 = \infty$ | | | |
| | $d_1 = 0.8000$ | $n_1 = 1.80610$ | $v_1 = 40.95$ |
| $r_2 = 5.1410$ | | | |
| | $d_2 = 167.5000$ | | |
| $r_3 = 87.8610$ | | | |
| | $d_3 = 2.0000$ | $n_2 = 1.51633$ | $v_2 = 64.15$ |
| $r_4 = \infty$ (stop) | | | |
| | $d_4 = 2.0000$ | $n_3 = 1.51633$ | $v_3 = 64.15$ |
| $r_5 = -87.8610$ | | | |
| | $d_5 = 167.6300$ | | |
| $r_6 = \infty$ | | | |
| | $d_6 = 30.0000$ | | |
| $r_7 = 25.3040$ | | | |
| | $d_7 = 3.0000$ | $n_4 = 1.69680$ | $v_4 = 55.52$ |
| $r_8 = -15.5040$ | | | |
| | $d_8 = 1.0000$ | $n_5 = 1.69895$ | $v_5 = 30.12$ |
| $r_9 = \infty$ | | | |
| | $d_9 = 45.2800$ | | |
| $r_{10} = 9.0340$ | | | |
| | $d_{10} = 3.0000$ | $n_6 = 1.51633$ | $v_6 = 64.15$ |
| $r_{11} = -5.9710$ | | | |
| | $d_{11} = 1.0000$ | $n_7 = 1.71736$ | $v_7 = 29.51$ |
| $r_{12} = 49.0230$ | | | |
| | $d_{12} = 1.0000$ | | |
| $r_{13} = 9.0340$ | | | |
| | $d_{13} = 3.0000$ | $n_8 = 1.51633$ | $v_8 = 64.15$ |
| $r_{14} = -5.9710$ | | | |
| | $d_{14} = 1.0000$ | $n_9 = 1.71736$ | $v_9 = 29.51$ |
| $r_{15} = 49.0230$ | | | |
| $D_1 = 339.6$ mm, $D_e = 300$ mm, $D_1/D_e = 1.132$, $\beta_2 = -0.958$ | | | |

In the numerical data of the second embodiment described above, $r_1$ through $r_5$ correspond to the objective lens system and $r_7$ through $r_{15}$ correspond to the imaging lens system for the TV camera. Further, $r_4$ represents an imaginary stop and $r_6$ designates a primary image.

The optical system preferred as the second embodiment of the present invention uses the objective lens system which is quite the same as that adopted for the first embodiment. Accordingly, the second embodiment uses no relay lens system and comprises an extremely small number of lens elements in the insert section thereof. The second embodiment has aberrations which are corrected favorably as illustrated in FIG. 47A, FIG. 47B, FIG. 47C and FIG. 47D.

Figure 10:
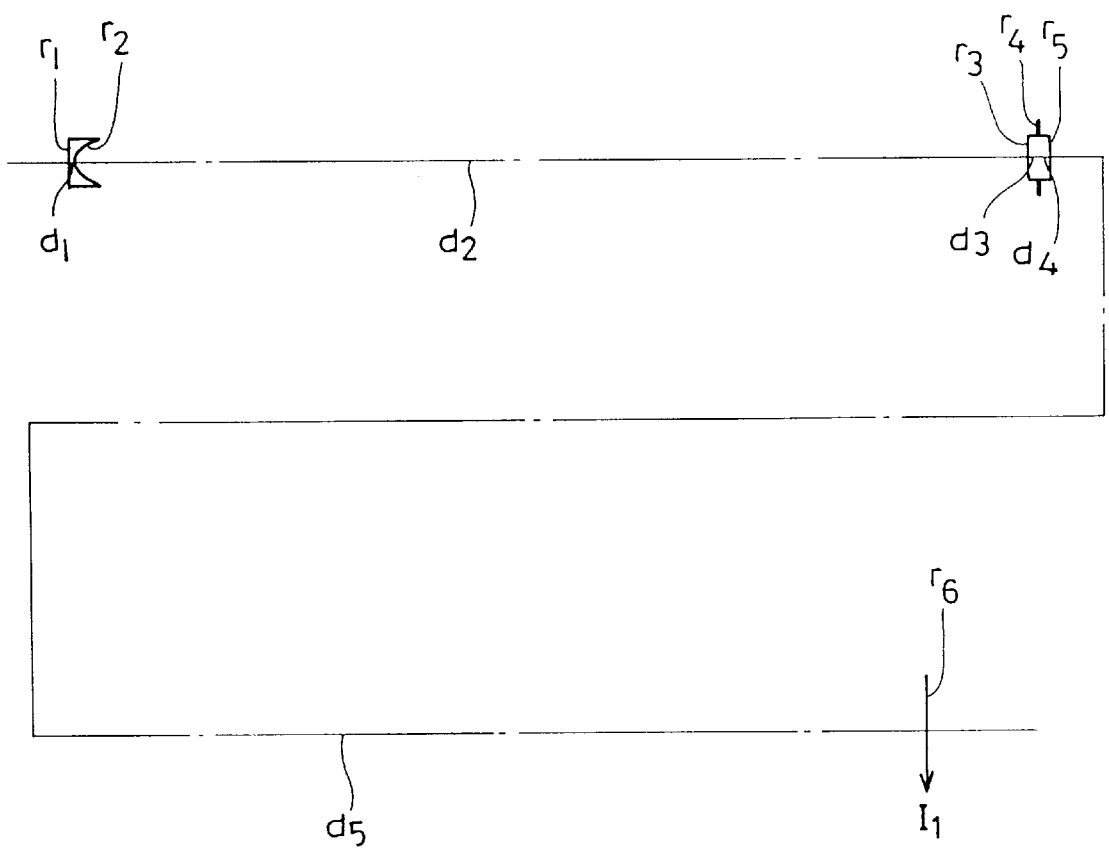
FIG. 10 shows a sectional view illustrating a composition of a third embodiment of the non-flexible endoscope according to the present invention.
Figure 11:
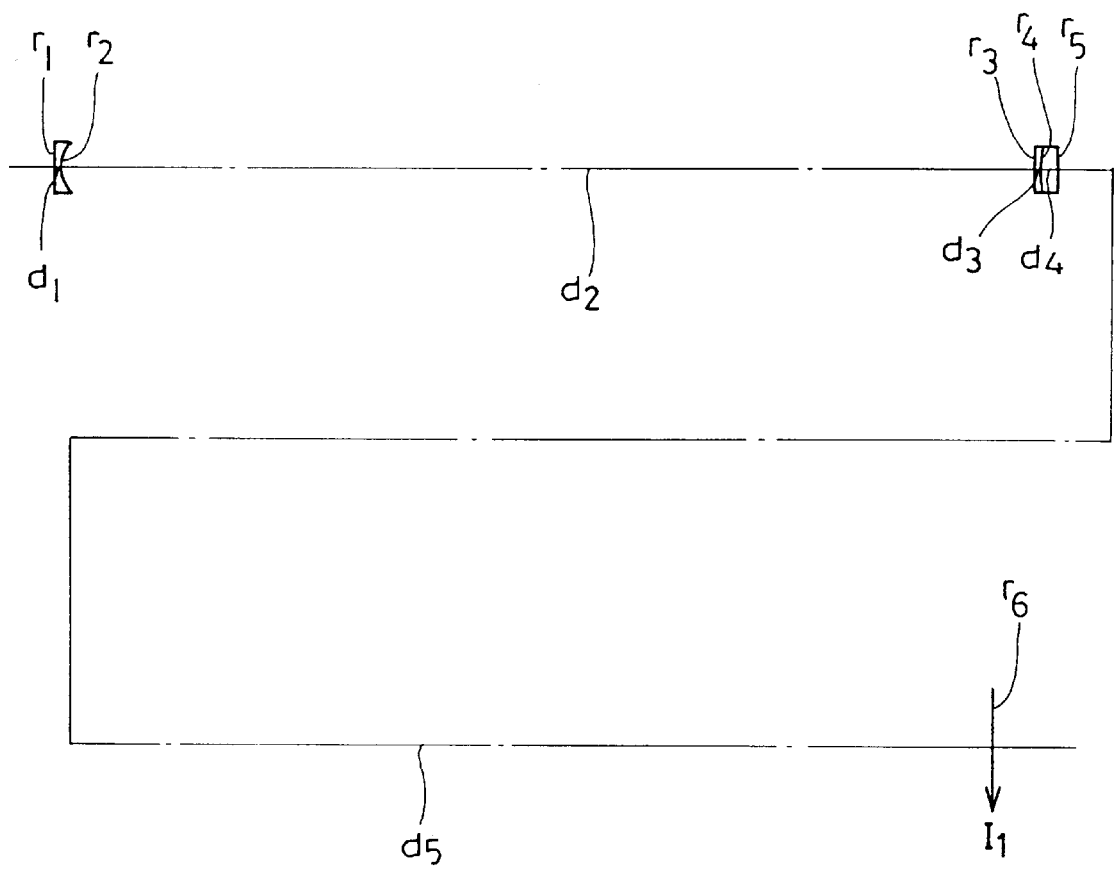
FIG. 11 shows a sectional view illustrating a composition of a fourth embodiment of the non-flexible endoscope according to the present invention.

FIG. 10 and FIG. 11 show a third embodiment and a fourth embodiment respectively of the optical system to be used in the non-flexible endoscope according to the present invention. Numerical data of these embodiments are listed below:

Embodiment 3

| object distance = −30, NA for incidence = 0.002, field angle = 70° | | | |
|---|---|---|---|
| $r_1 = \infty$ | | | |
| | $d_1 = 0.8000$ | $n_1 = 1.49216$ | $v_1 = 57.50$ |
| $r_2 = 1.6894$ (aspherical surface) | | | |
| | $d_2 = 167.5000$ | | |
| $r_3 = 83.1893$ | | | |
| | $d_3 = 2.0000$ | $n_2 = 1.49216$ | $v_2 = 57.50$ |
| $r_4 = \infty$ (stop) | | | |
| | $d_4 = 2.0000$ | $n_3 = 1.49216$ | $v_3 = 57.50$ |
| $r_5 = -83.1893$ | | | |
| | $d_5 = 167.5000$ | | |

-continued

| object distance = −30, NA for incidence = 0.002, field angle = 70° | | | |
|---|---|---|---|
| $r_6 = \infty$ | | | |
| $D_1 = 339.8$ mm, $D_e = 300$ mm, $D_1/D_e = 1.133$, $\beta_2 = -0.978$ aspherical surface coefficient $P = 0.0500$ | | | |

Embodiment 4

| object distance = −30, NA for incidence = 0.0033, field angle = 60° | | | |
|---|---|---|---|
| $r_1 = \infty$ | | | |
| | $d_1 = 0.8000$ | $n_1 = 1.80610$ | $v_1 = 40.95$ |
| $r_2 = 5.1692$ | | | |
| | $d_2 = 167.5000$ | | |
| $r_3 = 71.8444$ | | | |
| | $d_3 = 1.0000$ | $n_2 = 1.64769$ | $v_2 = 33.80$ |
| $r_4 = 29.4929$ (stop) | | | |
| | $d_4 = 3.0000$ | $n_3 = 1.51633$ | $v_3 = 64.15$ |
| $r_5 = -71.8444$ | | | |
| | $d_5 = 167.5000$ | | |
| $r_6 = \infty$ | | | |
| $D_1 = 339.8$ mm, $D_e = 300$ mm, $D_1/D_e = 1.133$, $\beta_2 = -0.957$ | | | |

Only objective lens systems used in the third embodiment and the fourth embodiment are represented by FIG. 10, FIG. 11 and the numerical data listed above. In the numerical data of the third embodiment, $r_4$ represents an imaginary stop and $r_6$ designates a primary image. In the numerical data of the fourth embodiment, $r_4$ represents an imaginary stop and $r_6$ designates a primary image.

The objective lens system used in the third embodiment is composed of lens elements made of plastic materials which may be acrylic resin materials or other plastic materials so far as they are optical materials having low dispersing powers. Further, the first lens component is a single plano-concave lens element having an image side concave surface which has such an aspherical surface as to lower curvature from an optical axis toward a margin thereof. The aspherical surface which has such a shape as to lower curvature from the optical axis toward the margin thereof is selected for correcting astigmatism and distortion by this aspherical surface itself. When the optical system is composed of lens elements which have only spherical surfaces, astigmatism will be remarkably overcorrected and barrel distortion will be produced. In the third embodiment, distortion is corrected to −1% at a maximum image height of the primary image. Furthermore, the second lens component is configured as a single biconvex lens element $r_3$, $r_5$ having the same radius of curvature on both surfaces thereof.

The aspherical surface used in the third embodiment has a shape expressed by the following formula (a):

$$z = \frac{y^2/r}{1 + \sqrt{1 - Py^2/r^2}} \tag{a}$$

wherein the reference symbol z represents a distance as measured, in a direction along the optical axis of the aspherical surface, from an intersection between the aspherical surface and the optical axis, the reference symbol y designates a distance as measured from the optical axis, the reference symbol r denotes a radius of curvature on the reference sphere of the aspherical surface, and the reference symbol p represents a parameter expressing a shape of a guadratic surface.

This aspherical surface has no term of high order and is selectable for manufacturing aspherical lens elements at low costs.

The objective lens system adopted for the fourth embodiment of the optical system for non-flexible endoscope according to the present invention is composed of a first lens component consisting of a single plano-concave lens element and a second lens component consisting of a biconvex cemented lens component. Though the objective lens system adopted for the fourth embodiment which uses the second cemented lens component requires an additional lens element, it has a merit to favorably correct longitudinal chromatic aberration and spherical aberration. The cemented lens component is composed of a positive lens element which has a relatively low refractive index and a weak dispersing power, and a negative lens element which has a high refractive index and a strong dispersing power.

In other words, this cemented lens component is configured so as to satisfy the following condition (4):

$$n_p < n_N, \quad v_p > v_N \quad (4)$$

wherein the reference symbols $n_p$ and $n_N$ represent refractive indices of the positive lens element and the negative lens element respectively disposed in the cemented lens component, and the reference symbols $v_p$ and $v_N$ designate Abbe's numbers of the positive lens element and the negative lens element respectively disposed in the cemented lens component.

In the cemented lens component, the negative lens element may be disposed on the object side as shown in FIG. 11 or on the image side. Further, the cemented lens component may have a plano-convex or meniscus shape instead of the biconvex shape selected for the fourth embodiment.

Figure 7:
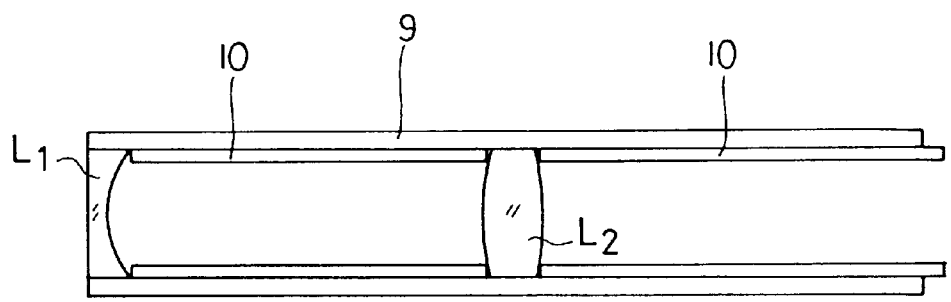
FIG. 7 shows a sectional view exemplifying a frame structure for an insert section of the non-flexible endoscope according to the present convention.

FIG. 7 exemplifies a frame structure for the objective lens system. A tube 9 of an observation system shown in this drawing consists of a pipe which has an inside diameter just fitting over an outside diameters of the lens components and accommodates the objective lens system fixed with spacers 10. The spacers 10 are made of a metal or a synthetic resin material and have inside surfaces which should desirably be treated into rougthened surfaces, preferably in black. If the spacers have inside surfaces which are specular surfaces having high reflectance, rays reflected by the inside surfaces of the spacers will reach an image surface, thereby undesirably producing flare.

Then, description will be made of an eyepiece lens system and an imaging lens system which are to be used in the optical system of the non-flexible endoscope according to the present invention.

Figure 8:
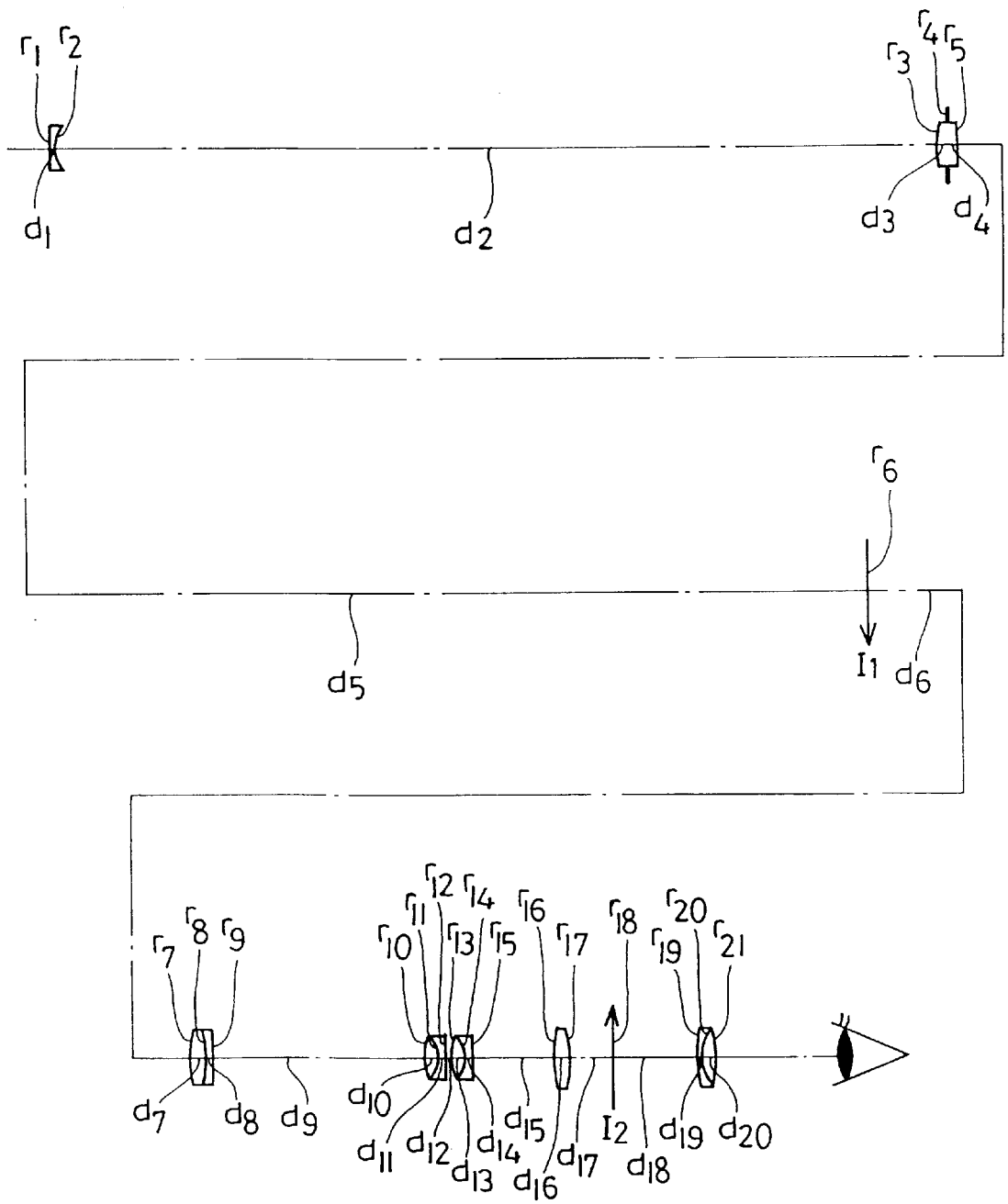
FIG. 8 shows a sectional view illustrating a composition of a first embodiment of the non-flexible endoscope according to the present invention.

The eyepiece lens system to be used in the optical system of the non-flexible endoscope according to the present invention has a composition illustrated in FIG. 8 ($r_7$ through $r_{21}$), for example, and has a role of a magnifying lens for observing a primary image $I_1$ ($r_6$) which is formed by the objective lens system. However, the objective lens system forms an inverted image and it is necessary to obtain an erect image with the optical system as a whole including the objective lens system. For this reason, the eyepiece lens system to be used in the optical system of the non-flexible endoscope according to the present invention is configured so as to perform a single cycle of image relaying within the eyepiece lens system itself and then form a secondary mage $I_2$ ($r_{18}$) which is to be observed. In other words, an image to be observed will undesirably be inverted when the secondary image $I_2$ is not formed in the eyepiece lens system itself.

Further, the objective lens system has the simple composition and can hardly correct aberrations sufficiently by itself. Accordingly, the optical system of the non-flexible endoscope according to the present invention is configured so as to correct aberrations in the optical system as a whole including the objective lens system and the eyepiece lens system. That is to say, the eyepiece lens system is configured so as to correct mainly aberrations which cannot be corrected by the objective lens system.

In the first embodiment of the optical system of the non-flexible endoscope according to the present invention, for example, the objective lens system is composed only of a single lens component and undercorrects longitudinal chromatic aberration. For correcting this undercorrected longitudinal chromatic aberration, at least two cemented lens components are used in the eyepiece lens system so as to overcorrect longitudinal chromatic aberration in the eyepiece lens system, whereby the optical system as a whole favorably corrects longitudinal chromatic aberration by cancelling the longitudinal chromatic aberration undercorrected by the objective lens system with the longitudinal chromatic aberration overcorrected by the eyepiece lens system.

Further, when manufacturing precisions of parts are lowered for reducing a manufacturing cost of the objective lens system, positional variations of the primary image will be large in a direction along the optical axis, thereby degrading focusing accuracy. For correcting such degradation of focusing accuracy, it is desirable to equip the eyepiece lens system with a focusing mechanism. As the focusing mechanism for the eyepiece lens system, it can be considered to adopt a mechanism for moving the eyepiece lens system as a whole along the optical axis or an inner-focus type mechanism for moving some of lens components disposed in the eyepiece lens system along the optical axis.

Furthermore, it is desirable to dispose a field stop at a location of the secondary image $I_2$ or the primary image $I_1$ since a field stop disposed at such a location is capable of preventing a border of visual field being dim and hindering flare from being produced due to rays coming from outside the visual field.

Now, description will be made of the imaging lens system to be used in the non-flexible endoscope according to the present invention which is configured for observation on a TV monitor. This imaging lens system has a composition illustrated as $r_7$ through $r_{15}$ in FIG. 9, for example, and a role to relay the primary image $I_1$ formed by the objective lens system onto an image pickup surface of a solid-state image pickup device. Like the eyepiece lens system described above, the imaging lens system is configured so as to correct aberrations in the optical system as a whole including the objective lens system. Therefore, the imaging lens system is configured so as to correct aberrations which cannot be corrected by the objective lens system. Longitudinal chromatic aberration, in particular, is overcorrected by using at least two cemented lens components in the imaging lens system so that longitudinal chromatic aberration undercorrected by the objective lens system is corrected favorably in the optical system as a whole.

Also in case of the non-flexible endoscope configured for observation on a TV monitor, it is desirable to equip the TV camera adaptor with a focusing mechanism. It is possible to select, as the focusing mechanism, a mechanism for moving the imaging lens system as a whole or an inner-focus type mechanism for moving some of lens components disposed in the imaging lens system. Further, it is possible to prevent a border of a visual field from being dim and hinder flare from being produced due to rays coming from outside the visual field by disposing a stop at a location of the primary image.

Though the non-flexible endoscope according to the present invention is configured mainly for making certain parts thereof (the insert section) disposable, the configuration of the non-flexible endoscope according to the present invention is applicable also to non-flexible endoscopes which are configured to use parts thereof repeatedly without discarding them for lowering cost prices thereof. It is sufficient for such application to integrate the insert section 1 and the eyepiece section 2 so as to be inseparable from each other in the configuration illustrated in FIG. 2. In case of the configuration illustrated in FIG. 3, it is sufficient to integrate the insert section 1 and the TV camera adaptor 3 so as to be inseparable from each other. Further, it is possible to integrate all of the insert section 1, the TV camera adaptor 3 and the TV camera 4 so as to be inseparable from one another.

That is to say, it is possible to integrate the insert section with a photographing section accommodating the imaging lens system and a solid-state image pickup device so that they have an inseparable unit structure.

Even for the non-flexible endoscopes which are configured to use parts thereof repeatedly, the reduction in numbers of optical elements realized by the omission of relay lens systems provides merits from viewpoints of cost prices and assembling convenience thereof.

The non-flexible endoscope according to the present invention has the fundamental configuration which is characterized in that only the objective lens system is disposed in the insert section to be inserted into a location to be observed and that the objective lens system forms the primary image in the vicinity of the near end (an end surface located on the side opposite to the leading end) of the insert section. That is to say, the non-flexible endoscope according to the present invention is configured so as to permit composing an observation optical sysem by attaching the insert section comprising the objective lens system to the eyepiece section comprising the eyepiece lens system for observation of the object side or attaching a TV camera to the eyepiece section for picking up an image or observation on a TV monitor. However, the non-flexible endoscopes according to the present invention is essentially characterized in that the objective lens system is disposed in the insert section or the like described above so as to form a primary image at the near end (the end surface located on the side opposite to the leading end) of the insert section, thereby accomplishing the objects of the present invention.

Now, description will be made of a configuration of the non-flexible endoscope according to the present invention of a type which comprises a relay lens system disposed in an optical system thereof.

An optical system of the non-flexible endoscope according to the present invention which is of the type comprising a relay lens system consists of a slender insert section which is to be inserted into body cavities for observing interiors thereof and a grip section which is to be kept outside the cavities even during observation. Accommodated in the insert section are an objective lens system which is disposed on the side of a leading end of the insert section for forming a primary image and a relay lens system which serves for relaying the primary image so as to form a secondary image in the vicinity of a near end of the insert section or in the grip section, whereas the grip section accommodates an eyepiece lens system which receives rays coming from the secondary image and allows rays to emerge therefrom in a condition where they are made parallel with one another so as to be observable by human eyes. This optical system is characterized in that it satisfies the following condition (5):

$$0.3 < D_1/D_2 < 0.7 \tag{5}$$

wherein the reference symbol $D_1$ represents a distance as measured from a leading end surface of the objective lens system to the primary image and the reference symbol $D_2$ designates a distance as measured from the leading end surface to the secondary image.

Speaking more concretely, the non-flexible endoscope according to the present invention described above has a configuration illustrated in FIG. 12, for example, or consists of a slender insert section 1 which is to be inserted into cavities of living bodies and the like, and a grip section which is to be kept outside the cavities even during use of the non-flexible endoscope and comprises an eyepiece section 2 disposed in a near end thereof. Further, accommodated in the insert section 1 are an objective lens system O which is disposed in the leading end thereof, a primary field lens $F_1$ which is disposed in the vicinity of a primary image $I_1$ formed by the objective lens system O, and a relay lens unit $R_1$ which serves for relaying the primary image $I_1$ so as to form a secondary image $I_2$. Further, disposed in the grip section 5 is an eyepiece lens system E which converts rays coming from the secondary image $I_2$ into rays which are nearly parallel with one another so as to be observable by naked eyes. Furthermore, it is possible to attach the eyepiece section 2 to a TV camera system 6 for endoscopes which is configured as a separate unit comprising a solid-state image pickup device 11 and an imaging lens system IL.

Figure 12:
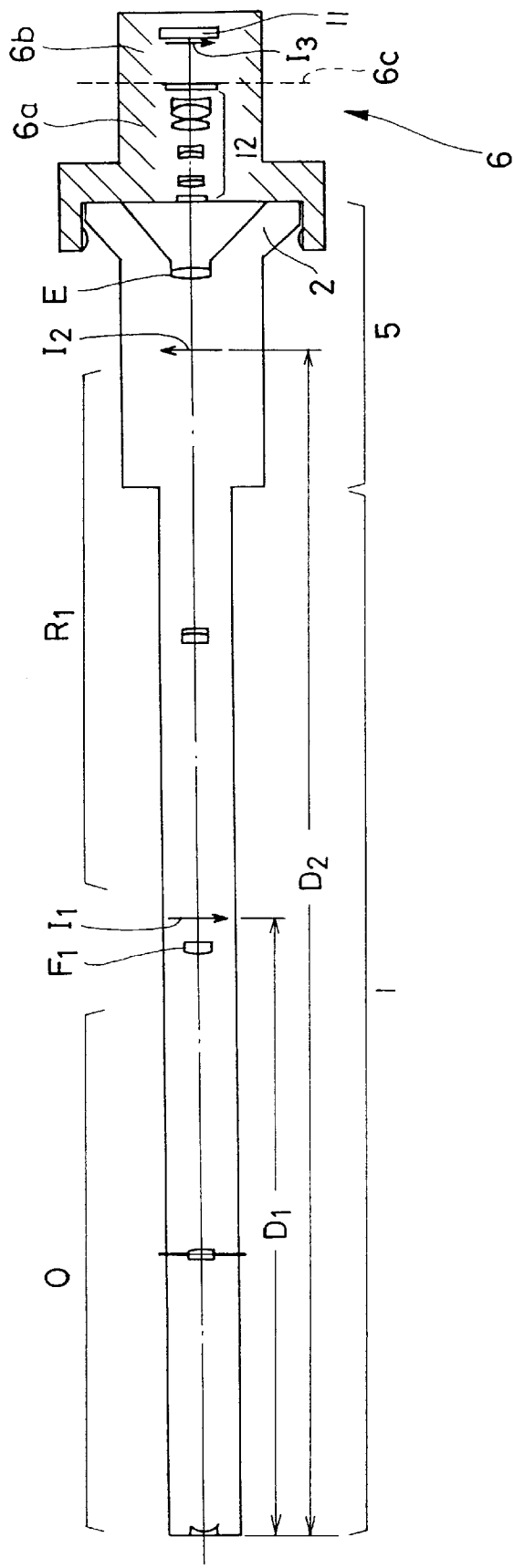
FIG. 12 shows a sectional view illustrating an optical system for the non-flexible endoscope according to the present invention which comprises a relay lens system.

Though the TV camera system 6 is mechanically integrated in FIG. 12, it is possible to compose this system of a section 6a comprising the imaging lens system IL and another section 6b comprising the solid-state image pickup device so that the system is separable along the dashed line 6C shown in FIG. 12 into the two sections which are mechanically attachable and detachable to and from each other. In this case, the section 6a which comprises the imaging lens system IL has a role of an adaptor for attaching the section 6b, or a TV camera head, to the non-flexible endoscope. When the TV camera 6 is configured so as to have a separable configuration described above, it provides a convenience to use various combinations of adaptors and TV camera heads which are prepared in plural kinds respectively.

A greatest characteristic of the optical system of the non-flexible endoscope according to the present invention which has the configuration described above lies in that a relay lens unit is configured so as to perform image relaying only in one cycle for reducing a number of lens elements to be used in the non-flexible endoscope and the objective lens system is configured so as to form the primary image nearly in the middle of a section from the leading end of the endoscope to the secondary image for preventing a numerical aperture from being reduced by the image relaying.

The optical system of the non-flexible endoscope according to the present invention comprises, in order from the side of the leading end thereof, the objective lens system O, the primary field lens $F_1$, the relay lens unit $R_1$ and the eyepiece lens system E: the objective lens system O serves for forming the primary image $I_1$ in the insertion section and the relay lens $R_1$ serves for forming the secondary image $I_2$ in the grip section 5 as described above. The primary field lens $F_1$ is disposed in the vicinity of the primary image $I_1$.

When a primary field lens is to be disposed on the side of the objective lens system O of a primary image $I_1$, it may be regarded as a lens component of the objective lens system O or when the primary field lens $F_1$ is to be disposed on the side of a relay lens unit $R_1$ of the primary image $I_1$, it may be considered as a lens component of the relay lens unit $R_1$.

In an ordinary case where a final image which is formed on the object side of the eyepiece lens system E is located in the vicinity of a near end of an insert section or in the grip section, the secondary image $I_2$ is formed as a final image on the optical system of the non-flexible endoscope according to the present invention. Accordingly, the distance as measured from the leading end of the insert section to the secondary image must be equal to or longer than an effective length of the insert section. Though a smaller effective length of the insert section makes it possible to obtain a brighter optical system, the insert section has an effective length which is determined almost dependently only on a length required for handling of a non-flexible endoscope and cannot be shorter than this length.

Since the location of the secondary image, out of the two images formed in the non-flexible endoscope according to the present invention, is determined as described above, the present invention selects a location of the primary image which is suited for obtaining a bright optical system.

Figure 13A:
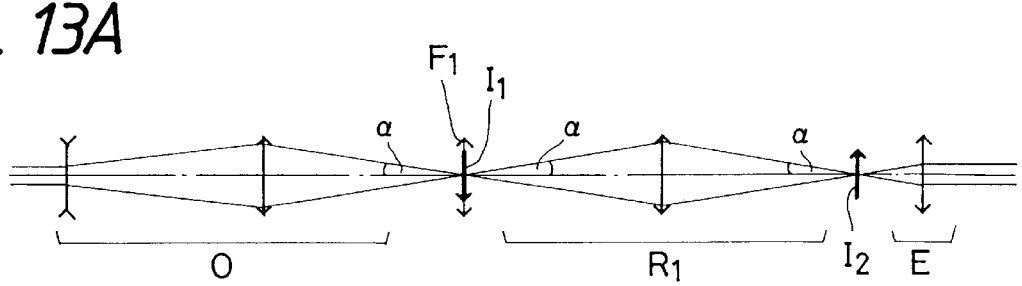
FIG. 13A, FIG. 13B and FIG. 13C show diagrams visualizing relationship between locations of primary images in non-flexible endoscopes and numerical apertures thereof.
Figure 13B:
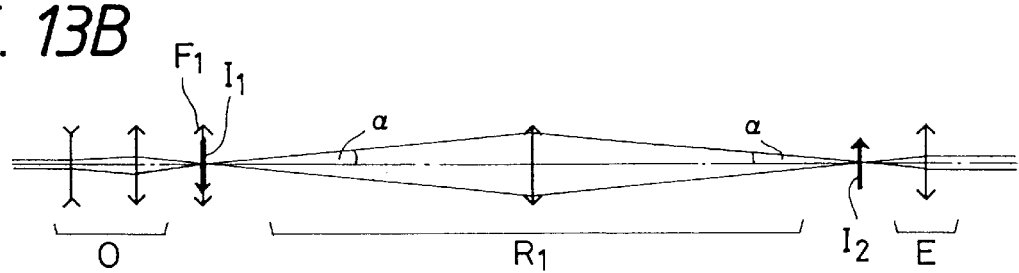
Figure 13C:
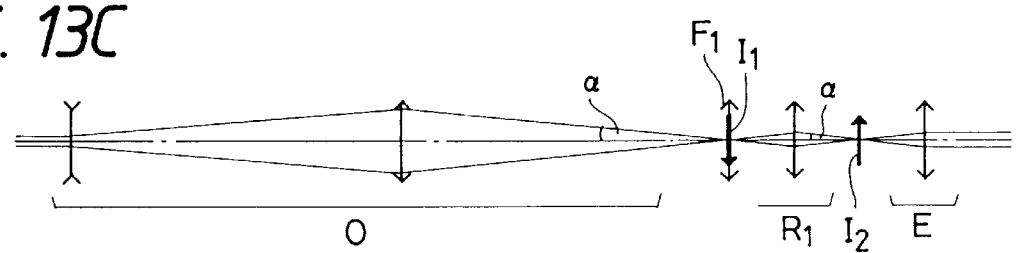

FIG. 13A, FIG. 13B and FIG. 13C show diagrams visualizing variations of numerical apertures to be caused by changing a location of a primary image. FIG. 13A illustrates a case where the primary image $I_1$ is located in the middle between the leading end of the objective lens system O and the secondary image $I_2$ by prolonging the objective lens system O, FIG. 13B visualizes a case where the location of the primary image $I_1$ is shifted toward the leading end by shortening the objective lens system O and FIG. 13C shows a case where the location of the primary image $I_1$ is shifted toward the secondary image $I_2$ by remarkably prolonging the objective lens system O. Out of these drawings, FIG. 13A shows a refractive power distribution which is most desirable for accomplishing the objects of the present invention, whereas FIG. 13B shows a composition which is similar to that in the conventional optical system for non-flexible endoscopes which uses a short objective lens system O.

In each of FIG. 13A, FIG. 13B and FIG. 13C wherein a relay lens unit $R_1$ has a magnification set at 1x and a primary field lens $F_1$ is overlapped with the primary image $I_1$, the objective lens system O has a numerical aperture on the side of incidence which is equal to a numerical aperture thereof on the side of emergence.

Numerical apertures are determined dependently on angles a which are formed between marginal rays and optical axes as shown in FIG. 13A, FIG. 13B and FIG. 13C. Speaking concretely, a numerical aperture is defined as NA=sin α and a larger angle a makes it possible to obtain a brighter optical system.

Though the marginal rays are traced at an equal maximum height in FIG. 13A, FIG. 13B and FIG. 13C, it is apparent that the angle a is the largest and permits obtaining a brightest optical system in the case shown in FIG. 13A since a lens system which determines a limit of heights of the marginal rays is not either one of the objective lens system O and the relay lens unit $R_1$ in this case. In the case illustrated in FIG. 13B, a limit of heights of the marginal rays is determined by the relay lens system $R_1$ only and the angle α is determined by a length of the relay lens unit $R_1$. In the case visualized in FIG. 13C, a limit of heights of the marginal rays is determined by the objective lens system O only and the angle α is determined by a length of the objective lens system O. In the case illustrated in FIG. 13A, in contrast, a limit of heights of the marginal rays is determined by both the objective lens system O and the relay lens unit $R_1$ either of which has a length shorter than that of the relay lens unit $R_1$ shown in FIG. 13B or that of the objective lens system O shown in FIG. 13C, whereby the location of the primary image $I_1$ shown in FIG. 13A allows to form a large angle a which makes it possible to obtain a brightest optical system when outside diameters of the lens systems are predetermined to a definite value.

Apart from the qualitative description of the optical system of the non-flexible endoscope according to the present invention, it is quantitatively sufficient to configure the optical system so as to satisfy the above-mentioned condition (5).

The reference symbol $D_1/D_2$ used in the condition (5) represents a parameter for varying brightness in the optical system and has a value of 0.5 in the condition illustrated in FIG. 13A which permits configuring the optical system so as to be brightest.

Accordingly, brightness in the optical system will be lowered if $D_1/D_2$ has a value larger or smaller than 0.5. When brightness at $D_1/D_2$ is taken as 1, brightness at various values of $D_1/D_2$ is expressed by an equation of $1/\{1+|1-(2D_1/D_2)|\}^2$ or calculated as listed below:

| $D_1/D_2$ | Brightness |
|---|---|
| 0.1, 0.9 | 0.31 |
| 0.2, 0.8 | 0.39 |
| 0.3, 0.7 | 0.51 |
| 0.4, 0.6 | 0.69 |
| 0.5 | 1 |

As is understood from the values tabulated above, brightness at $D_1/D_2$=0.3 or 0.7 is 0.51 times as high as that at $D_1/D_2$=0.5, or brightness is halved by lowering $D_1/D_2$ from 0.5 to 0.3 or enhancing it from 0.5 to 0.7. Since brightness is not allowed to be lower than that at $D_1/D_2$=0.3 or 0.7, it is necessary that the optical system satisfies the above-mentioned condition (5). If the lower limit of 0.3 of the condition (5) is exceeded, the optical system will be set in the condition shown in FIG. 13B or if the upper limit of 0.7 of the condition (5) is exceeded, the optical system will be set in the condition shown in FIG. 13C, whereby brightness will be lowered to about ½ of that at $D_1/D_2$=0.5 or the optical system will be too dark for practical use.

It is possible to obtain at least 70% of the brightness at $D_1/D_2$=0.5 when the above-mentioned condition (5) is modified so as to have a lower limit of 0.4 and an upper limit of 0.6. It is therefore more desirable to configure the optical system so as to satisfy the following condition:

$$0.4 < D_1/D_2 < 0.6$$

In FIG. 12, the primary field lens $F_1$ is disposed in the vicinity of the primary iamge $I_1$ for transmitting a pupil of the objective lens system O to the relay lens unit $R_1$. since a principal ray which emerges from the objective lens system O travels in a direction away from the optical axis, the principal ray cannot pass through the relay lens unit $R_1$ if the field lens is not disposed in the vicinity of the primary image, whereby an image will be eclipsed at a marginal portion of a visual field. For this reason, the primary field lens $F_1$ must be disposed in the vicinity of the primary image. When a surface of the field lens $F_1$ is overlapped with the primary image, however, dust or injury existing on the surface of the field lens $F_1$ will be imaged. It is therefore desirable to dispose the field lens $F_1$ so as to have air-contact surfaces located with narrow spacings reserved from the primary image $I_1$.

It is possible to carry out observation on a TV monitor which is essential for surgical operations under observation through an endoscope when a TV camera system for non-flexible endoscope is attached to a non-flexible endoscope comprising an optical system of the type which uses a relay lens system as described above. For such observation on a TV monitor, it is sufficient to connect a TV camera system 6 to a grip section 2 of a non-flexible endoscope as in the case of the non-flexible endoscope shown in FIG. 12, for example, so that an imaging lens system IL disposed in the TV camera system for non-flexible endoscope forms a ternary image $I_3$ at a location coincident with a light receiving surface of a solid-state image pickup device for allowing this device to pick up the image.

Now, description will be made of an optical system which is of a type desirable for use in the non-flexible endoscope according to the present invention and comprises not only the objective lens system O described above but also a relay lens unit $R_1$. It is desirable to compose the objective lens system O of a first lens component which is disposed in the leading end of an insert section and has a negative refractive power and a second lens component which is disposed between the first lens component and a primary field lens, and has a positive refractive power. Such a refractive power distribution is selected for the objective lens system O so that a number of lens components to be disposed in the objective lens system O is reduced while required field angle thereof. The negative refractive power is imparted to the first lens component for allowing it to have a function for widening a field angle and the positive refractive power is imparted to the second lens component for allowing it to relay a virtual image formed by the first lens component so as to form a real image. The first lens component of the objective lens system O has the strongest negative refractive power out of lens components disposed in an observation optical system and is therefore effective also for correction of curvature of field. Further, the second lens component of the objective lens system O has a role of a pupil in the objective lens system. The refractive power distribution described above permits minimizing a number of lens components to be disposed in the objective lens system O, or allows this lens system to have a simplest composition.

In the configuration shown in FIG. 12, the objective lens system is composed only of two lens elements, or a first lens component consisting of a single negative lens element and a second lens component consisting only of a positive lens element. However, a refractive power of the first lens component which consists of the single negative lens element may be insufficient for certain specifications of the optical system such as a field angle thereof and the first lens component can comprise an additional lens element having a negative refractive power. Further, the first lens component can comprise a lens element having a positive refractive power or be configured as a cemented lens component for favorably correcting lateral chromatic aberration and astigmatism. When the objective lens system is composed only of spherical lens elements, it produces barrel distortion. For correcting this distortion, it is sufficient to use an aspherical surface in the first lens component, on which the principal ray is high, so as to prevent the principal ray from being refracted excessively. Further, for correcting longitudinal chromatic aberration by the second lens component, it is sufficient to configure it so as to comprise a negative lens element having a strong dispersing power, or have a composition consisting of a positive lens element and a negative lens element. In this case, the positive lens element and the negative lens element may be cemented to each other or disposed as separate lens elements. It is most desirable that the second lens component has a magnification of approximately −1x or it should preferably have a magnification within a range from −2x to −0.5x. The objective lens system will have a pupil at a location largely apart from a middle between the leading end thereof and the primary image, whereby offaxial rays will undesirably be eclipsed if the second lens component has a magnification within a range defined by the following condition (6):

$$0.5 < |\beta_2| < 2.0 \qquad (6)$$

wherein the reference symbol $\beta_2$ represents the magnification of the second lens component.

Next, a primary field lens may be disposed on either side of the primary image, i.e., on the side of the objective lens system or on the side of the relay lens, or so as to locate the primary image therein. When the primary field lens is too far from the primary image, however, an image will be eclipsed or intensities of the marginal rays will be lowered. Therefore, it is desirable that a distance $D_3$ as measured from the primary field lens to the primary image is within 10% of a value of $D_2$ mentioned above.

In other words, it is desirable to configure the objective lens system so as to satisfy the following condition (7):

$$|D_3/D_2| \leq 0.1 \qquad (7)$$

If the distance as measured from the primary field lens to the primary image exceeds 10% of $D_2$, the primary field lens itself will eclipse the offaxial rays, thereby causing eclipse of an image at marginal portions of a visual field or lowering of intensities of the marginal rays. The primary field lens must have a positive refractive power for transmitting a pupil and can have a function sufficient for this purpose when it is composed of a single positive lens element. For correcting lateral chromatic aberration and astigmatism, however, it is desirable to configure the primary field lens as a cemented lens component consisting of a positive lens element and a negative lens element.

Further, a relay lens unit need not have a symmetrical shape or a complicated composition, unlike the relay lens system used in the conventional optical system for non-flexible endoscopes which is configured so as to perform a plurality of image relay cycles.

The relay lens unit to be used in the optical system of the non-flexible endoscope according to the present invention can be composed simply by disposing a lens component having a positive refractive power nearly in the middle between the primary image and the secondary image, and this lens component has a role of a pupil of the relay lens unit. This lens component having the positive refractive power may be composed of a single positive lens element, but for correction of longitudinal chromatic aberration it is to be composed of a positive lens element and a negative lens element. The positive lens element and the negative lens element may be cemented to each other or disposed separately.

In the optical system of the non-flexible endoscope according to the present invention in which both the second lens component of the objective lens system and the relay lens unit have roles of pupils in an observation optical system, it is sufficient for correction of longitudinal chromatic aberration in the observation optical system to compose at least either of the second lens component and the relay lens unit of a combination of a positive lens element and a negative lens element.

In the optical system of the endoscope shown in FIG. 12, the relay lens unit is configured as a cemented lens component consisting of a positive lens element and a negative lens element for correcting longitudinal chromatic aberration, whereas the second lens component of the objective lens system is composed of a single lens element.

In a case where aspherical surfaces are to be used for correcting spherical aberration, it is sufficient to configure at least either of the second lens component of the objective lens system or the relay lens unit so as to have an aspherical surface which has such a shape as to lower curvature toward a marginal portion thereof. As already described above, the relay lens unit should desirably have a magnification of approximately −1x or within a range defined by the following condition (8):

$$-2 < \beta_R < -0.5 \tag{8}$$

wherein the reference symbol $\beta_2$ represents the magnification of the relay lens system.

If the relay lens unit has a magnification largely deviated from the range defined above, the relay lens unit will have a pupil at a location largely deviated from the middle between the primary image and the secondary image, whereby the offaxial rays will be eclipsed.

The eyepiece lens system has a positive refractive power and can be composed sufficiently of a single positive lens element. For correcting lateral chromatic aberration and astigmatism, however, the eyepiece lens system may be composed of a positive lens element and a negative lens element which may be cemented to each other or disposed separately.

In the fundamental composition of the optical system of the non-flexible endoscope according to the present invention, no particular consideration is taken for an eye point of the eyepiece lens system. When positional control of the eye point is important in actual lens design, however, it is allowable to dispose a secondary field lens in the vicinity of the secondary image for positional control of the eye point by using a refractive power of the secondary field lens.

In the conventional non-flexible endoscope, a visual field mask is disposed at an imaging location for clarifying a range of a visual field to be observed. A visual field mask can be disposed also in the optical system of the non-flexible endoscope according to the present invention. In such a case, it is most desirable to dispose a visual field mask composed of a thin black metal sheet or the similar material at a location of the secondary image which imposes a weak spatial restriction, but such a visual field mask may be disposed at a location of the primary image or in the first lens component of the objective lens system on which the principal ray is low.

Listed below are numerical data of the preferred embodiments of the optical system of the non-flexible endoscape according to the present invention which is of the type described above (characterized in that it comprises at least an objective lens system and a relay lens system):

Embodiment 5

| f = 8.130 mm, object distance = −30 mm maximum image height on TV camera side = 4.08 mm, F number on TV camera side = 17.83, field angle = 60° | | | |
|---|---|---|---|
| $r_1 = \infty$ | | | |
| | $d_1 = 0.8000$ | $n_1 = 1.80610$ | $\nu_1 = 40.95$ |
| $r_2 = 5.1239$ | | | |
| | $d_2 = 80.2734$ | | |
| $r_3 = 46.7013$ | | | |
| | $d_3 = 1.5000$ | $n_2 = 1.51633$ | $\nu_2 = 64.15$ |
| $r_4 = \infty$ (stop) | | | |

-continued

| f = 8.130 mm, object distance = −30 mm maximum image height on TV camera side = 4.08 mm, F number on TV camera side = 17.83, field angle = 60° | | | |
|---|---|---|---|
| | $d_4 = 1.5000$ | $n_3 = 1.51633$ | $\nu_3 = 64.15$ |
| $r_5 = -46.7013$ | | | |
| | $d_5 = 85.1824$ | | |
| $r_6 = 45.0033$ | | | |
| | $d_6 = 3.0000$ | $n_4 = 1.51633$ | $\nu_4 = 64.15$ |
| $r_7 = -45.0033$ | | | |
| | $d_7 = 7.0000$ | | |
| $r_8 = \infty$ | | | |
| | $d_8 = 77.6197$ | | |
| $r_9 = 68.6864$ | | | |
| | $d_9 = 3.0000$ | $n_5 = 1.58913$ | $\nu_5 = 61.18$ |
| $r_{10} = -11.2095$ | | | |
| | $d_{10} = 1.0000$ | $n_6 = 1.76182$ | $\nu_6 = 26.55$ |
| $r_{11} = -23.7341$ | | | |
| | $d_{11} = 79.1246$ | | |
| $r_{12} = \infty$ | | | |
| | $d_{12} = 20.1878$ | | |
| $r_{13} = 21.8541$ | | | |
| | $d_{13} = 3.0000$ | $n_7 = 1.51633$ | $\nu_7 = 64.15$ |
| $r_{14} = -21.8541$ | | | |
| | $d_{14} = 19.2020$ | | |
| $r_{15} = \infty$ | | | |
| | $d_{15} = 1.0000$ | $n_8 = 1.51633$ | $\nu_8 = 64.15$ |
| $r_{16} = \infty$ | | | |
| | $d_{16} = 3.1818$ | | |
| $r_{17} = 13.7100$ | | | |
| | $d_{17} = 1.3700$ | $n_9 = 1.72000$ | $\nu_9 = 50.25$ |
| $r_{18} = -13.7100$ | | | |
| | $d_{18} = 1.0000$ | $n_{10} = 1.78472$ | $\nu_{10} = 25.71$ |
| $r_{19} = \infty$ | | | |
| | $d_{19} = 6.6282$ | | |
| $r_{20} = -6.8120$ | | | |
| | $d_{20} = 1.5000$ | $n_{11} = 1.84666$ | $\nu_{11} = 23.78$ |
| $r_{21} = -3.7050$ | | | |
| | $d_{21} = 0.8000$ | $n_{12} = 1.62374$ | $\nu_{12} = 47.10$ |
| $r_{22} = 8.7190$ | | | |
| | $d_{22} = 4.5260$ | | |
| $r_{23} = 18.9290$ | | | |
| | $d_{23} = 2.7600$ | $n_{13} = 1.62041$ | $\nu_{13} = 60.06$ |
| $r_{24} = -13.4420$ | | | |
| | $d_{24} = 0.2000$ | | |
| $r_{25} = 9.1970$ | | | |
| | $d_{25} = 4.7100$ | $n_{14} = 1.51633$ | $\nu_{14} = 64.15$ |
| $r_{26} = -9.1970$ | | | |
| | $d_{26} = 0.8000$ | $n_{15} = 1.85026$ | $\nu_{15} = 32.28$ |
| $r_{27} = 23.0810$ | | | |
| | $d_{27} = 3.5960$ | | |
| $r_{28} = \infty$ | | | |
| | $d_{28} = 1.0000$ | $n_{16} = 1.51633$ | $\nu_{16} = 64.15$ |
| $r_{29} = \infty$ | | | |
| | $d_{29} = 14.1000$ | | |
| $r_{30} = \infty$ | | | |
| $D_1 = 179.26$ mm, $D_2 = 340$ mm, $D_1/D_2 = 0.527$, $\beta_2 = -1.12$, $\beta_R = -1.00$ | | | |

Embodiment 6

| object distance = −30 mm, maximum image height on TV camera side = 4.08 mm, F number on TV camera side = 20.71, field angle = 60° | | | |
|---|---|---|---|
| $r_1 = \infty$ | | | |
| | $d_1 = 0.8000$ | $n_1 = 1.80610$ | $\nu_1 = 40.95$ |
| $r_2 = 5.1763$ | | | |
| | $d_2 = 68.4331$ | | |
| $r_3 = 40.1441$ | | | |
| | $d_3 = 1.5000$ | $n_2 = 1.51633$ | $\nu_2 = 64.15$ |
| $r_4 = \infty$ (stop) | | | |
| | $d_4 = 1.5000$ | $n_3 = 1.51633$ | $\nu_3 = 64.15$ |
| $r_5 = -40.1441$ | | | |
| | $d_5 = 71.3720$ | | |
| $r_6 = 43.6088$ | | | |
| | $d_6 = 3.0000$ | $n_4 = 1.51633$ | $\nu_4 = 64.15$ |

-continued object distance = −30 mm,
maximum image height on TV camera side = 4.08 mm,
F number on TV camera side = 20.71, field angle = 60°

| | | | |
|---|---|---|---|
| $r_7 = -43.6088$ | | | |
| | $d_7 = 7.0000$ | | |
| $r_8 = \infty$ | | | |
| | $d_8 = 91.7825$ | | |
| $r_9 = 29.9977$ | | | |
| | $d_9 = 1.0000$ | $n_5 = 1.76182$ | $\nu_5 = 26.55$ |
| $r_{10} = 14.1459$ | | | |
| | $d_{10} = 3.0000$ | $n_6 = 1.58913$ | $\nu_6 = 61.18$ |
| $r_{11} = -68.4094$ | | | |
| | $d_{11} = 90.6124$ | | |
| $r_{12} = \infty$ | | | |
| | $d_{12} = 20.1530$ | | |
| $r_{13} = 21.8162$ | | | |
| | $d_{13} = 3.0000$ | $n_7 = 1.51633$ | $\nu_7 = 64.15$ |
| $r_{14} = -21.8162$ | | | |

$D_1 = 153.61$ mm, $D_2 = 340$ mm, $D_1/D_2 = 0.452$,
$\beta_2 = 1.11$, $\beta_R = -1.00$ Embodiment 7 object distance = −30 mm,
maximum image height on TV camera side = 4.08 mm,
F number on TV camera side = 19.21, field angle = 70°

| | | | |
|---|---|---|---|
| $r_1 = \infty$ | | | |
| | $d_1 = 0.8000$ | $n_1 = 1.51633$ | $\nu_1 = 64.15$ |
| $r_2 = 14.4251$ | | | |
| | $d_2 = 0.6000$ | | |
| $r_3 = \infty$ | | | |
| | $d_3 = 0.8000$ | $n_2 = 1.80610$ | $\nu_2 = 40.95$ |
| $r_4 = 4.3308$ | | | |
| | $d_4 = 69.9342$ | | |
| $r_5 = 44.5266$ | | | |
| | $d_5 = 1.5000$ | $n_3 = 1.51633$ | $\nu_3 = 64.15$ |
| $r_6 = \infty$ (stop) | | | |
| | $d_6 = 1.5000$ | $n_4 = 1.51633$ | $\nu_4 = 64.15$ |
| $r_7 = -44.5266$ | | | |
| | $d_7 = 92.6837$ | | |
| $r_8 = 46.8089$ | | | |
| | $d_8 = 3.0000$ | $n_5 = 1.51633$ | $\nu_5 = 64.15$ |
| $r_9 = -46.8089$ | | | |
| | $d_9 = 7.0000$ | | |
| $r_{10} = \infty$ | | | |
| | $d_{10} = 78.3941$ | | |
| $r_{11} = 64.2273$ | | | |
| | $d_{11} = 3.0000$ | $n_6 = 1.58913$ | $\nu_6 = 61.18$ |
| $r_{12} = -10.9857$ | | | |
| | $d_{12} = 1.0000$ | $n_7 = 1.76182$ | $\nu_7 = 26.55$ |
| $r_{13} = -24.1056$ | | | |
| | $d_{13} = 79.7881$ | | |
| $r_{14} = \infty$ | | | |
| | $d_{14} = 20.1825$ | | |
| $r_{15} = 21.8483$ | | | |
| | $d_{15} = 3.0000$ | $n_8 = 1.51633$ | $\nu_8 = 64.15$ |
| $r_{16} = -21.8483$ | | | |

$D_1 = 177.82$ mm, $D_2 = 340$ mm, $D_1/D_2 = 0.523$,
$\beta_2 = -1.39$, $\beta_R = -1.00$ Embodiment 8 object distance = −30 mm,
maximum image height on TV camera side = 4.08 mm,
F number on TV camera side = 18.17, field angle = 60°

| | | | |
|---|---|---|---|
| $r_1 = \infty$ | | | |
| | $d_1 = 0.8000$ | $n_1 = 1.80610$ | $\nu_1 = 40.95$ |
| $r_2 = 5.1142$ | | | |
| | $d_2 = 82.0469$ | | |
| $r_3 = 47.8629$ | | | |
| | $d_3 = 3.0000$ | $n_2 = 1.58913$ | $\nu_2 = 61.18$ |
| $r_4 = -13.2592$ (stop) | | | |

-continued object distance = −30 mm,
maximum image height on TV camera side = 4.08 mm,
F number on TV camera side = 18.17, field angle = 60°

| | | | |
|---|---|---|---|
| | $d_4 = 1.0000$ | $n_3 = 1.76182$ | $\nu_3 = 26.55$ |
| $r_5 = -34.2575$ | | | |
| | $d_5 = 87.7317$ | | |
| $r_6 = 45.1573$ | | | |
| | $d_6 = 3.0000$ | $n_4 = 1.51633$ | $\nu_4 = 64.15$ |
| $r_7 = -45.1573$ | | | |
| | $d_7 = 7.0000$ | | |
| $r_8 = \infty$ | | | |
| | $d_8 = 76.2107$ | | |
| $r_9 = 39.3499$ | | | |
| | $d_9 = 3.0000$ | $n_5 = 1.51633$ | $\nu_5 = 64.15$ |
| $r_{10} = -39.3499$ | | | |
| | $d_{10} = 76.2107$ | | |
| $r_{11} = \infty$ | | | |
| | $d_{11} = 20.1992$ | | |
| $r_{12} = 21.8665$ | | | |
| | $d_{12} = 3.0000$ | $n_6 = 1.51633$ | $\nu_6 = 64.15$ |
| $r_{13} = -21.8665$ | | | |

$D_1 = 184.58$ mm, $D_2 = 340$ mm, $D_1/D_2 = 0.543$,
$\beta_2 = -1.12$, $\beta_R = -1.00$ Embodiment 9 object distance = −30 mm,
maximum image height on TV camera side = 4.08 mm,
F number on TV camera side = 19.54, field angle = 60°

| | | | |
|---|---|---|---|
| $r_1 = \infty$ | | | |
| | $d_1 = 0.8000$ | $n_1 = 1.80518$ | $\nu_1 = 25.43$ |
| $r_2 = 5.0888$ | | | |
| | $d_2 = 89.1783$ | | |
| $r_3 = 46.7638$ | | | |
| | $d_3 = 1.5000$ | $n_2 = 1.51633$ | $\nu_2 = 64.15$ |
| $r_4 = \infty$ (stop) | | | |
| | $d_4 = 1.5000$ | $n_3 = 1.51633$ | $\nu_3 = 64.15$ |
| $r_5 = -46.7638$ | | | |
| | $d_5 = 87.0248$ | | |
| $r_6 = \infty$ | | | |
| | $d_6 = 7.0000$ | | |
| $r_7 = 44.3580$ | | | |
| | $d_7 = 3.0000$ | $n_4 = 1.51633$ | $\nu_4 = 64.15$ |
| $r_8 = -44.3580$ | | | |
| | $d_8 = 75.2496$ | | |
| $r_9 = 48.0450$ | | | |
| | $d_9 = 3.0000$ | $n_5 = 1.58913$ | $\nu_5 = 61.18$ |
| $r_{10} = -10.6465$ | | | |
| | $d_{10} = 1.0000$ | $n_6 = 1.76182$ | $\nu_6 = 26.55$ |
| $r_{11} = -25.7579$ | | | |
| | $d_{11} = 70.7473$ | | |
| $r_{12} = \infty$ | | | |
| | $d_{12} = 20.2187$ | | |
| $r_{13} = 21.8878$ | | | |
| | $d_{13} = 3.0000$ | $n_7 = 1.51633$ | $\nu_7 = 64.15$ |
| $r_{14} = -21.8878$ | | | |

$D_1 = 180$ mm, $D_2 = 340$ mm, $D_1/D_2 = 0.529$,
$\beta_2 = -0.92$, $\beta_R = -0.82$ Embodiment 10 object distance = −30 mm,
maximum image height on TV camera side = 4.08 mm,
F number on TV camera side = 18.72, field angle = 60°

| | | | |
|---|---|---|---|
| $r_1 = \infty$ | | | |
| | $d_1 = 0.8000$ | $n_1 = 1.80610$ | $\nu_1 = 40.95$ |
| $r_2 = 5.1065$ | | | |
| | $d_2 = 85.2715$ | | |
| $r_3 = 45.9553$ | | | |
| | $d_3 = 1.5000$ | $n_2 = 1.51633$ | $\nu_2 = 64.15$ |
| $r_4 = \infty$ (stop) | | | |
| | $d_4 = 1.5000$ | $n_3 = 1.51633$ | $\nu_3 = 64.15$ |

-continued object distance = −30 mm,
maximum image height on TV camera side = 4.08 mm,
F number on TV camera side = 18.72, field angle = 60°

| | | | | |
|---|---|---|---|---|
| $r_5 =$ | −45.9553 | | | |
| | $d_5 = 83.3820$ | | | |
| $r_6 =$ | 41.9389 | | | |
| | $d_6 = 6.0000$ | $n_4 = 1.51633$ | $\nu_4 = 64.15$ | |
| $r_7 =$ | ∞ | | | |
| | $d_7 = 6.0000$ | $n_5 = 1.51633$ | $\nu_5 = 64.15$ | |
| $r_8 =$ | −41.9389 | | | |
| | $d_8 = 75.0594$ | | | |
| $r_9 =$ | 57.8740 | | | |
| | $d_9 = 3.0000$ | $n_6 = 1.58913$ | $\nu_6 = 61.18$ | |
| $r_{10} =$ | −10.9911 | | | |
| | $d_{10} = 1.0000$ | $n_7 = 1.76182$ | $\nu_7 = 26.55$ | |
| $r_{11} =$ | −25.5483 | | | |
| | $d_{11} = 76.4871$ | | | |
| $r_{12} =$ | ∞ | | | |
| | $d_{12} = 20.1964$ | | | |
| $r_{13} =$ | 21.8634 | | | |
| | $d_{13} = 3.0000$ | $n_8 = 1.51633$ | $\nu_8 = 64.15$ | |
| $r_{14} =$ | −21.8634 | | | |

$D_1 = 178.45$ mm, $D_2 = 340$ mm, $D_1/D_2 = 0.525$,
$\beta_2 = -0.97$, $\beta_R = -0.95$ Embodiment 11 object distance = −30 mm,
maximum image height on TV camera side = 4.08 mm,
F number on TV camera side = 18.26, field angle = 60°

| | | | | |
|---|---|---|---|---|
| $r_1 =$ | ∞ | | | |
| | $d_1 = 0.8000$ | $n_1 = 1.49216$ | $\nu_1 = 57.50$ | |
| $r_2 =$ | 2.4305 (aspherical surface) | | | |
| | $d_2 = 74.6460$ | | | |
| $r_3 =$ | 43.1965 (aspherical surface) | | | |
| | $d_3 = 1.5000$ | $n_2 = 1.49216$ | $\nu_2 = 57.50$ | |
| $r_4 =$ | ∞ (stop) | | | |
| | $d_4 = 1.5000$ | $n_3 = 1.49216$ | $\nu_3 = 57.50$ | |
| $r_5 =$ | −43.1965 (aspherical surface) | | | |
| | $d_5 = 88.0859$ | | | |
| $r_6 =$ | 43.7851 | | | |
| | $d_6 = 3.0000$ | $n_4 = 1.49216$ | $\nu_4 = 57.50$ | |
| $r_7 =$ | −43.7851 | | | |
| | $d_7 = 7.0000$ | | | |
| $r_8 =$ | ∞ | | | |
| | $d_8 = 79.0426$ | | | |
| $r_9 =$ | 64.0973 | | | |
| | $d_9 = 3.0000$ | $n_5 = 1.58913$ | $\nu_5 = 61.18$ | |
| $r_{10} =$ | −10.9645 | | | |
| | $d_{10} = 1.0000$ | $n_6 = 1.76182$ | $\nu_6 = 26.55$ | |
| $r_{11} =$ | −24.2504 | | | |
| | $d_{11} = 80.4254$ | | | |
| $r_{12} =$ | ∞ | | | |
| | $d_{12} = 20.2086$ | | | |
| $r_{13} =$ | 20.8614 | | | |
| | $d_{13} = 3.0000$ | $n_7 = 1.49216$ | $\nu_7 = 57.50$ | |
| $r_{14} =$ | −20.8614 | | | | aspherical surface cofficients
(2nd surface) P = 0.2285, (3rd surface) P = 1.5536,
(5th surface) P = 1.5536
$D_1 = 176.53$ mm, $D_2 = 340$ mm, $D_1/D_2 = 0.519$,
$\beta_2 = -1.25$, $\beta_R = -1.00$ Embodiment 12 object distance = −30 mm,
maximum image height on TV camera side = 4.08 mm,
F number on TV camera side = 20.83, field angle = 60°

| | | | | |
|---|---|---|---|---|
| $r_1 =$ | ∞ | | | |
| | $d_1 = 0.8000$ | $n_1 = 1.49216$ | $\nu_1 = 57.50$ | |
| $r_2 =$ | 2.4413 (aspherical surface) | | | |
| | $d_2 = 67.2311$ | | | |

-continued object distance = −30 mm,
maximum image height on TV camera side = 4.08 mm,
F number on TV camera side = 20.83, field angle = 60°

| | | | | |
|---|---|---|---|---|
| $r_3 =$ | 39.1495 | | | |
| | $d_3 = 1.5000$ | $n_2 = 1.49216$ | $\nu_2 = 57.50$ | |
| $r_4 =$ | ∞ (stop) | | | |
| | $d_4 = 1.5000$ | $n_3 = 1.49216$ | $\nu_3 = 57.50$ | |
| $r_5 =$ | −39.1495 | | | |
| | $d_5 = 78.7484$ | | | |
| $r_6 =$ | 42.1398 | | | |
| | $d_6 = 3.0000$ | $n_4 = 1.49216$ | $\nu_4 = 57.50$ | |
| $r_7 =$ | −42.1398 | | | |
| | $d_7 = 7.0000$ | | | |
| $r_8 =$ | ∞ | | | |
| | $d_8 = 83.0137$ | | | |
| $r_9 =$ | −38.7763 | | | |
| | $d_9 = 1.0000$ | $n_5 = 1.76182$ | $\nu_5 = 26.55$ | |
| $r_{10} =$ | 38.7763 | | | |
| | $d_{10} = 1.0000$ | | | |
| $r_{11} =$ | 16.8362 (aspherical surface) | | | |
| | $d_{11} = 3.0000$ | $n_6 = 1.49216$ | $\nu_6 = 57.50$ | |
| $r_{12} =$ | −16.8362 (aspherical surface) | | | |
| | $d_{12} = 92.2068$ | | | |
| $r_{13} =$ | ∞ | | | |
| | $d_{13} = 20.1708$ | | | |
| $r_{14} =$ | 20.8221 | | | |
| | $d_{14} = 3.0000$ | $n_7 = 1.49216$ | $\nu_7 = 57.50$ | |
| $r_{15} =$ | −20.8221 | | | | aspherical surface coefficient
(2nd surface) P = 0.2230, (11th surface) P = −0.7877,
(12th surface) P = −0.7877
$D_1 = 159.78$ mm, $D_2 = 340$ mm, $D_1/D_2 = 0.470$
$\beta_2 = -1.25$, $\beta_R = -1.00$ Embodiment 13 object distance = −30 mm,
maximum image height on TV camera side = 4.08 mm,
F number on TV camera side = 23.67, field angle = 60°

| | | | | |
|---|---|---|---|---|
| $r_1 =$ | ∞ | | | |
| | $d_1 = 0.8000$ | $n_1 = 1.49216$ | $\nu_1 = 57.50$ | |
| $r_2 =$ | 2.4989 (aspherical surface) | | | |
| | $d_2 = 57.0401$ | | | |
| $r_3 =$ | 33.5464 | | | |
| | $d_3 = 1.5000$ | $n_2 = 1.49216$ | $\nu_2 = 57.50$ | |
| $r_4 =$ | ∞ (stop) | | | |
| | $d_4 = 1.5000$ | $n_3 = 1.49216$ | $\nu_3 = 57.50$ | |
| $r_5 =$ | −33.5464 | | | |
| | $d_5 = 65.5966$ | | | |
| $r_6 =$ | 39.9491 | | | |
| | $d_6 = 3.0000$ | $n_4 = 1.49216$ | $\nu_4 = 57.50$ | |
| $r_7 =$ | −39.9491 | | | |
| | $d_7 = 7.0000$ | | | |
| $r_8 =$ | ∞ | | | |
| | $d_8 = 93.8257$ | | | |
| $r_9 =$ | −28.0116 | | | |
| | $d_9 = 1.0000$ | $n_5 = 1.58423$ | $\nu_5 = 30.30$ | |
| $r_{10} =$ | 28.0116 | | | |
| | $d_{10} = 1.0000$ | | | |
| $r_{11} =$ | 16.9806 (aspherical surface) | | | |
| | $d_{11} = 3.0000$ | $n_6 = 1.49216$ | $\nu_6 = 57.50$ | |
| $r_{12} =$ | −16.9806 (aspherical surface) | | | |
| | $d_{12} = 104.7376$ | | | |
| $r_{13} =$ | ∞ | | | |
| | $d_{13} = 20.1462$ | | | |
| $r_{14} =$ | 20.7965 | | | |
| | $d_{14} = 3.0000$ | $n_7 = 1.49216$ | $\nu_7 = 57.50$ | |
| $r_{15} =$ | −20.7965 | | | | aspherical surface coefficients
(2nd surface) P = 0.2408, (11th surface) P = −0.5399,
(12th surface) P = −0.5399
$D_1 = 136.44$ mm, $D_2 = 340$ mm, $D_1/D_2 = 0.401$,
$\beta_2 = -1.24$, $\beta_R = -1.00$

Embodiment 14 object distance = −30 mm,
maximum image height on TV camera side = 4.08 mm,
F number on TV camera side = 19.87, field angle = 60°

| | | | |
|---|---|---|---|
| $r_1 = \infty$ | | | |
| | $d_1 = 0.8000$ | $n_1 = 1.80400$ | $\nu_1 = 46.57$ |
| $r_2 = 5.0891$ | | | |
| | $d_2 = 86.7040$ | | |
| $r_3 = 47.6811$ | | | |
| | $d_3 = 1.5000$ | $n_2 = 1.51633$ | $\nu_2 = 64.15$ |
| $r_4 = \infty$ (stop) | | | |
| | $d_4 = 1.5000$ | $n_3 = 1.51633$ | $\nu_3 = 64.15$ |
| $r_5 = -47.6811$ | | | |
| | $d_5 = 81.9098$ | | |
| $r_6 = 43.6719$ | | | |
| | $d_6 = 3.0000$ | $n_4 = 1.51633$ | $\nu_4 = 64.15$ |
| $r_7 = -43.6719$ | | | |
| | $d_7 = 7.0000$ | | |
| $r_8 = \infty$ | | | |
| | $d_8 = 76.5667$ | | |
| $r_9 = 39.9780$ | | | |
| | $d_9 = 3.0000$ | $n_5 = 1.58913$ | $\nu_5 = 61.18$ |
| $r_{10} = -12.5062$ | | | |
| | $d_{10} = 1.0000$ | $n_6 = 1.76182$ | $\nu_6 = 26.55$ |
| $r_{11} = -30.4039$ | | | |
| | $d_{11} = 76.8498$ | | |
| $r_{12} = \infty$ | | | |
| | $d_{12} = 7.0000$ | | |
| $r_{13} = 96.5673$ | | | |
| | $d_{13} = 3.0000$ | $n_7 = 1.78472$ | $\nu_7 = 25.71$ |
| $r_{14} = -96.5673$ | | | |
| | $d_{14} = 11.3766$ | | |
| $r_{15} = 12.0529$ | | | |
| | $d_{15} = 3.0000$ | $n_8 = 1.51633$ | $\nu_8 = 64.15$ |
| $r_{16} = -157.9337$ | | | |

$D_1 = 182.41$ mm, $D_2 = 340$ mm, $D_1/D_2 = 0.537$
$\beta_2 = -1.01, \beta_R = -1.00$

Embodiment 15 object distance = −30 mm,
maximum image height on TV camera side = 4.08 mm,
F number on TV camera side = 17.62, field angle = 70°

| | | | |
|---|---|---|---|
| $r_1 = \infty$ | | | |
| | $d_1 = 0.8000$ | $n_1 = 1.80610$ | $\nu_1 = 40.95$ |
| $r_2 = 4.3638$ | | | |
| | $d_2 = 79.1915$ | | |
| $r_3 = 46.7018$ | | | |
| | $d_3 = 1.5000$ | $n_2 = 1.51633$ | $\nu_2 = 64.15$ |
| $r_4 = \infty$ (stop) | | | |
| | $d_4 = 1.5000$ | $n_3 = 1.51633$ | $\nu_3 = 64.15$ |
| $r_5 = -46.7018$ | | | |
| | $d_5 = 87.4834$ | | |
| $r_6 = 45.2400$ | | | |
| | $d_6 = 3.0000$ | $n_4 = 1.51633$ | $\nu_4 = 64.15$ |
| $r_7 = -45.2400$ | | | |
| | $d_7 = 7.0000$ | | |
| $r_8 = \infty$ | | | |
| | $d_8 = 77.0461$ | | |
| $r_9 = 65.5076$ | | | |
| | $d_9 = 3.0000$ | $n_5 = 1.58913$ | $\nu_5 = 61.18$ |
| $r_{10} = -11.2103$ | | | |
| | $d_{10} = 1.0000$ | $n_6 = 1.76182$ | $\nu_6 = 26.55$ |
| $r_{11} = -23.8871$ | | | |
| | $d_{11} = 78.4789$ | | |
| $r_{12} = \infty$ | | | |
| | $d_{12} = 19.5030$ | | |
| $r_{13} = 49.7945$ | | | |
| | $d_{13} = 1.0000$ | $n_7 = 1.72916$ | $\nu_7 = 54.68$ |
| $r_{14} = 18.6044$ | | | |
| | $d_{14} = 3.0000$ | $n_8 = 1.51823$ | $\nu_8 = 58.96$ |
| $r_{15} = -12.2921$ | | | |

$D_1 = 180.47$ mm, $D_2 = 340$ mm, $D_1/D_2 = 0.531$,
$\beta_2 = -1.17, \beta_R = -1.00$

Embodiment 16 object distance = −30 mm,
maximum image height on TV camera side = 4.08 mm,
F number on TV camera side = 13.28, field angle = 60°

| | | | |
|---|---|---|---|
| $r_1 = \infty$ | | | |
| | $d_1 = 0.8000$ | $n_1 = 1.80518$ | $\nu_1 = 25.43$ |
| $r_2 = 4.9043$ | | | |
| | $d_2 = 3.0000$ | | |
| $r_3 = 34.9905$ | | | |
| | $d_3 = 84.4997$ | $n_2 = 1.51633$ | $\nu_2 = 64.15$ |
| $r_4 = -41.4453$ | | | |
| | $d_4 = 1.0000$ | | |
| $r_5 = \infty$ (stop) | | | |
| | $d_5 = 1.0000$ | | |
| $r_6 = 27.6766$ | | | |
| | $d_6 = 84.3592$ | $n_3 = 1.51633$ | $\nu_3 = 64.15$ |
| $r_7 = -29.6190$ | | | |
| | $d_7 = 7.0000$ | | |
| $r_8 = \infty$ | | | |
| | $d_8 = 7.0000$ | | |
| $r_9 = 30.9409$ | | | |
| | $d_9 = 87.2633$ | $n_4 = 1.51633$ | $\nu_4 = 64.15$ |
| $r_{10} = \infty$ | | | |
| | $d_{10} = 1.0000$ | | |
| $r_{11} = 36.4798$ | | | |
| | $d_{11} = 3.0000$ | $n_5 = 1.58913$ | $\nu_5 = 61.18$ |
| $r_{12} = -10.8874$ | | | |
| | $d_{12} = 1.0000$ | $n_6 = 1.76182$ | $\nu_6 = 26.55$ |
| $r_{13} = -24.1409$ | | | |
| | $d_{13} = 59.0777$ | | |
| $r_{14} = \infty$ | | | |
| | $d_{14} = 20.2847$ | | |
| $r_{15} = 21.8841$ | | | |
| | $d_{15} = 3.0000$ | $n_7 = 1.51454$ | $\nu_7 = 54.69$ |
| $r_{16} = -21.8841$ | | | |

$D_1 = 181.66$ mm, $D_2 = 340$ mm, $D_1/D_2 = 0.534$,
$\beta_2 = -0.97, \beta_R = -0.88$

Embodiment 17 object distance = −30 mm,
maximum image height on TV camera side = 4.08 mm,
F number on TV camera side = 14.47, field angle = 60°

| | | | |
|---|---|---|---|
| $r_1 = \infty$ | | | |
| | $d_1 = 0.8000$ | $n_1 = 1.80610$ | $\nu_1 = 40.95$ |
| $r_2 = 4.8021$ | | | |
| | $d_2 = 3.0000$ | | |
| $r_3 = 27.9253$ | | | |
| | $d_3 = 93.1871$ | $n_2 = 1.51633$ | $\nu_2 = 64.15$ |
| $r_4 = -38.3056$ | | | |
| | $d_4 = 1.0000$ | | |
| $r_5 = \infty$ (stop) | | | |
| | $d_5 = 1.0000$ | | |
| $r_6 = 37.4772$ | | | |
| | $d_6 = 102.2232$ | $n_3 = 1.51633$ | $\nu_3 = 64.15$ |
| $r_7 = -18.4422$ | | | |
| | $d_7 = 7.0000$ | | |
| $r_8 = \infty$ | | | |
| | $d_8 = 63.4974$ | | |
| $r_9 = 41.4556$ | | | |
| | $d_9 = 3.0000$ | $n_4 = 1.58913$ | $\nu_4 = 61.18$ |
| $r_{10} = -11.2437$ | | | |
| | $d_{10} = 1.0000$ | $n_5 = 1.76182$ | $\nu_5 = 26.55$ |
| $r_{11} = -23.5963$ | | | |
| | $d_{11} = 64.2923$ | | |
| $r_{12} = \infty$ | | | |
| | $d_{12} = 20.2460$ | | |
| $r_{13} = 21.9177$ | | | |
| | $d_{13} = 3.0000$ | $n_6 = 1.51633$ | $\nu_6 = 64.15$ |
| $r_{14} = -21.9177$ | | | |

$D_1 = 208.21$ mm, $D_2 = 340$ mm, $D_1/D_2 = 0.612$,
$\beta_2 = -1.26, \beta_R = -1.00$ Embodiment 18

| object distance = −30 mm, maximum image height on TV camera side = 4.08 mm, F number on TV camera side = 13.87, field angle = 60° | | | |
|---|---|---|---|
| $r_1 = \infty$ | | | |
| | $d_1 = 0.8000$ | $n_1 = 1.80610$ | $v_1 = 40.95$ |
| $r_2 = 3.5575$ | | | |
| | $d_2 = 35.6752$ | | |
| $r_3 = 41.1433$ | | | |
| | $d_3 = 3.0000$ | $n_2 = 1.51633$ | $v_2 = 64.15$ |
| $r_4 = -41.1433$ | | | |
| | $d_4 = 78.3719$ | | |
| $r_5 = 41.1433$ | | | |
| | $d_5 = 3.0000$ | $n_3 = 1.51633$ | $v_3 = 64.15$ |
| $r_6 = -41.1433$ | | | |
| | $d_6 = 39.1529$ | | |
| $r_7 = \infty$ | | | |
| | $d_7 = 41.3193$ | | |
| $r_8 = 147.2366$ | | | |
| | $d_8 = 1.0000$ | $n_4 = 1.78472$ | $v_4 = 25.71$ |
| $r_9 = 17.9531$ | | | |
| | $d_9 = 3.0000$ | $n_5 = 1.51633$ | $v_5 = 64.15$ |
| $r_{10} = -16.3775$ | | | |
| | $d_{10} = 44.6807$ | | |
| $r_{11} = \infty$ (stop) | | | |
| | $d_{11} = 44.6807$ | | |
| $r_{12} = 16.3775$ | | | |
| | $d_{12} = 3.0000$ | $n_6 = 1.51633$ | $v_6 = 64.15$ |
| $r_{13} = -17.9531$ | | | |
| | $d_{13} = 1.0000$ | $n_7 = 1.78472$ | $v_7 = 25.71$ |
| $r_{14} = -147.2366$ | | | |
| | $d_{14} = 41.3193$ | | |
| $r_{15} = \infty$ | | | |
| | $d_{15} = 14.6359$ | | |
| $r_{16} = 15.9009$ | | | |
| | $d_{16} = 3.0000$ | $n_8 = 1.51633$ | $v_8 = 64.15$ |
| $r_{17} = -15.9009$ | | | |
| $D_1 = 160$ mm, $D_2 = 340$ mm, $D_1/D_2 = 0.471$, | | | |
| $\beta_2 = -1.00$ | | | | wherein the reference symbols $r_1$, $r_2$, . . . represent radii of curvature on surfaces of respective lens elements, the reference symbols $d_1$, $d_2$, . . . designate thicknesses of the respective lens elements and airspaces reserved therebetween, the reference symbols $n_1$, $n_2$, . . . denote refractive indices of the respective lens elements, and the reference symbols $v_1$, $v_2$, . . . represent Abbe's numbers of the respective lens elements.

Figure 14:
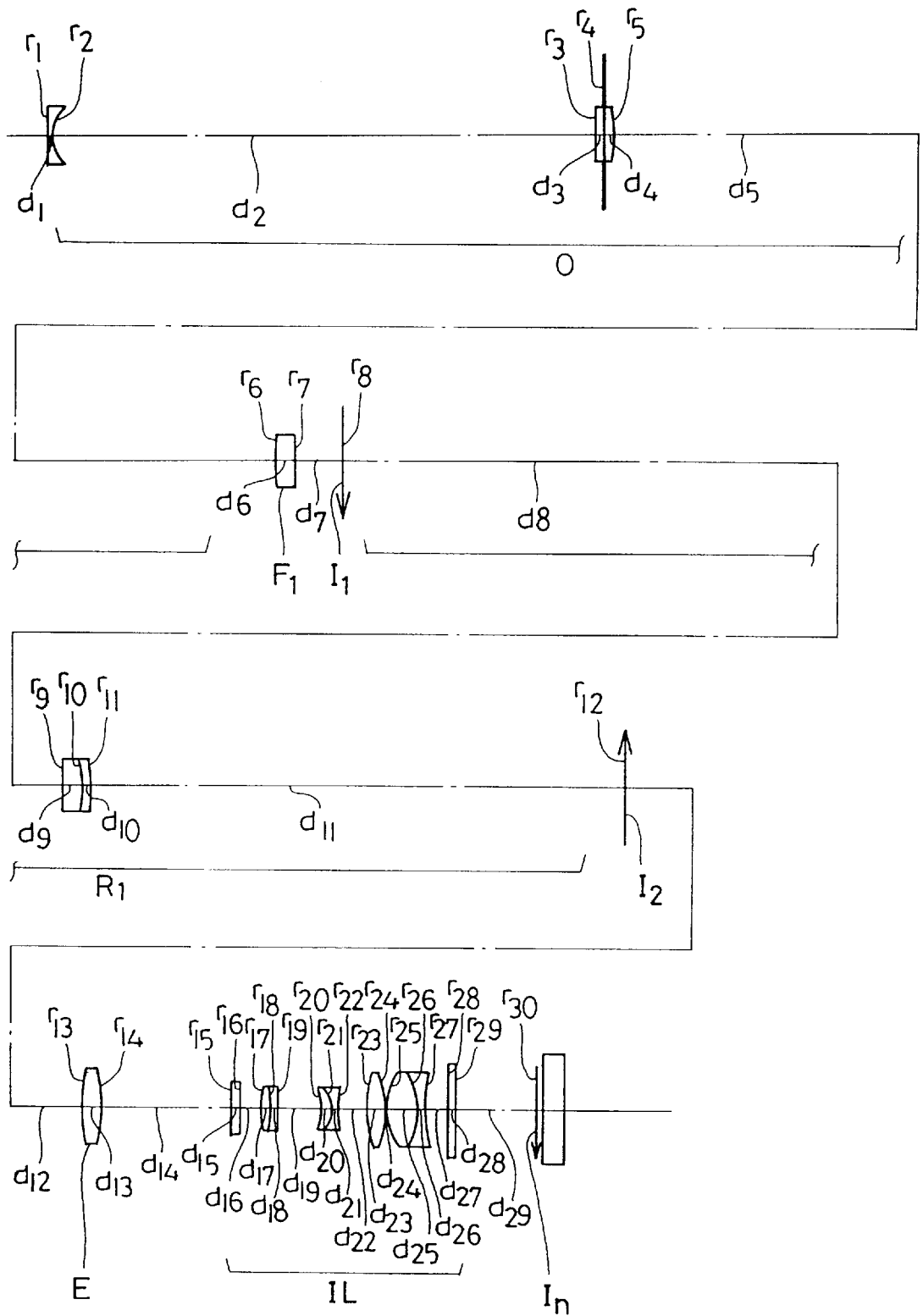
FIG. 14 shows a sectional view illustrating a composition of a fifth embodiment of the non-flexible endoscope according to the present invention.

The fifth embodiment of the present invention has a configuration shown in FIG. 12 and uses an optical system which has a composition illustrated in FIG. 14 on an enlarged scale. The fifth embodiment consists of: an objective lens system O ($r_1$ through $r_5$) which is composed of a first lens component consisting of a single negative plano-concave lens element and a second lens component consisting of a single biconvex positive lens element having the same radius of curvature on both surfaces thereof; a primary field lens $F_1$ ($r_6$ and $r_7$) which consists of a single positive biconvex lens element having the same radius of curvature on both surfaces thereof; a relay lens system $R_1$ ($r_9$ through $r_{11}$) which is composed of a cemented lens component having a positive refractive power, and consisting of a positive lens element and a negative lens element; and an eyepiece lens system ($r_{13}$ and $r_{14}$) which is composed of a single biconvex lens element having the same radius of curvature on both surfaces thereof. The fifth embodiment is composed only of the six lens element for manufacturing at a low cost. Further, all the lens elements other than the plano-concave lens element and those used for composing the cemented lens component are symmetrical with regard to vertical axes perpendicular to the right-to-left direction and require no discrimination between sides to be set on the object side and the image side, thereby facilitating assembling procedures. Furthermore, a distance as measured from $r_1$ to $r_8$ corresponds to $D_1$, whereas a distance as measured from $r_1$ to $r_{12}$ corresponds to $D_2$ when the fifth embodiment is combined with the imaging lens system IL ($r_{15}$ through $r_{29}$) shown in FIG. 14, the optical system has aberration characteristics illustrated in FIG. 48A, FIG. 48B, FIG. 48C and FIG. 48D. The reference symbol $r_{30}$ used in FIG. 14 represents an imaging location $I_n$.

Figure 15:
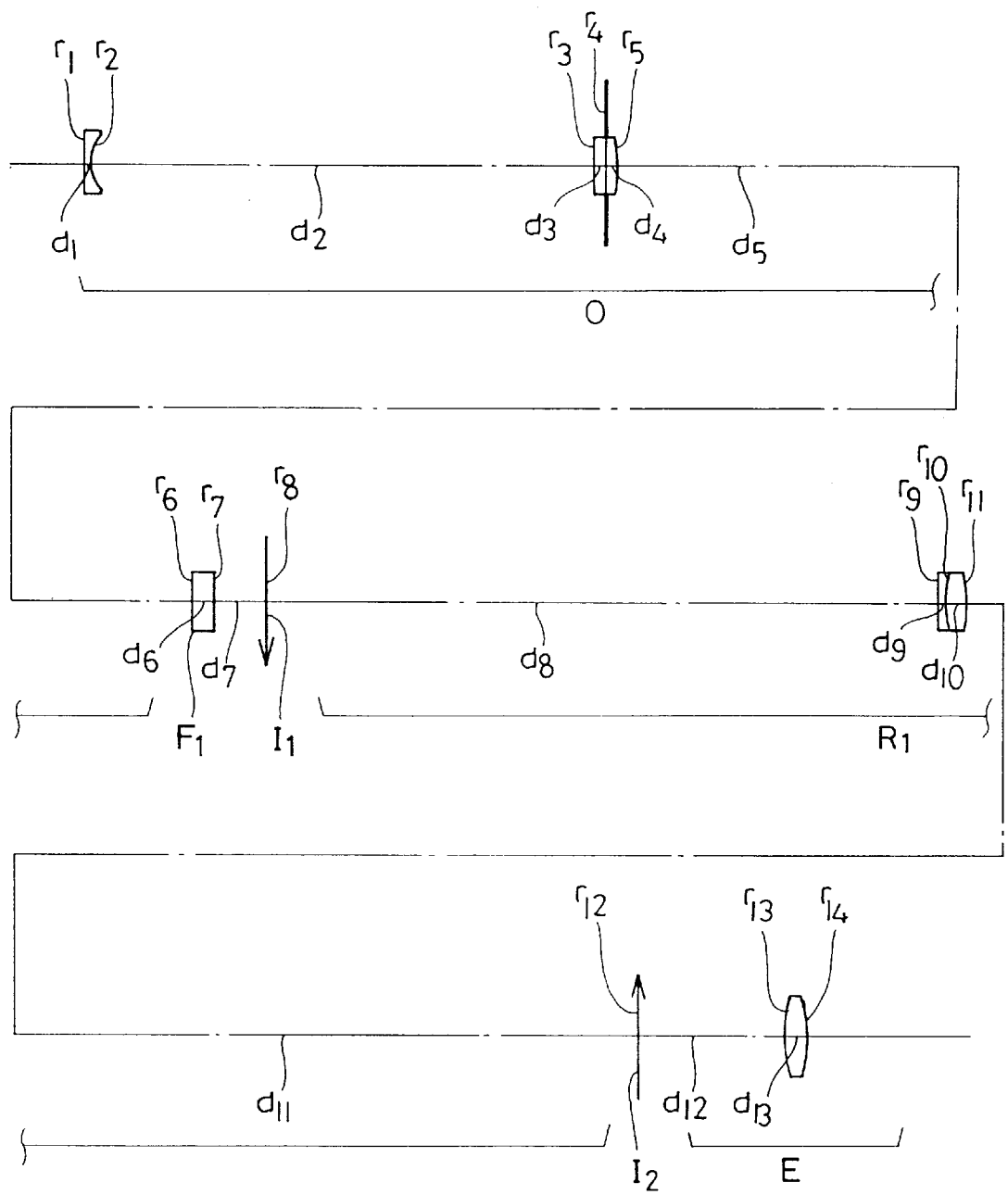
FIG. 15 shows a sectional view illustrating a composition of a sixth embodiment of the non-flexible endoscope according to the present invention.

The sixth embodiment has a composition illustrated in FIG. 15 which is similar to that of the fifth embodiment, except for a cemented lens surface ($r_{10}$) which is set in an opposite direction. Aberration characteristics of the sixth embodiment are illustrated in FIG. 49A, FIG. 49B, FIG. 49C and FIG. 49D.

Figure 16:
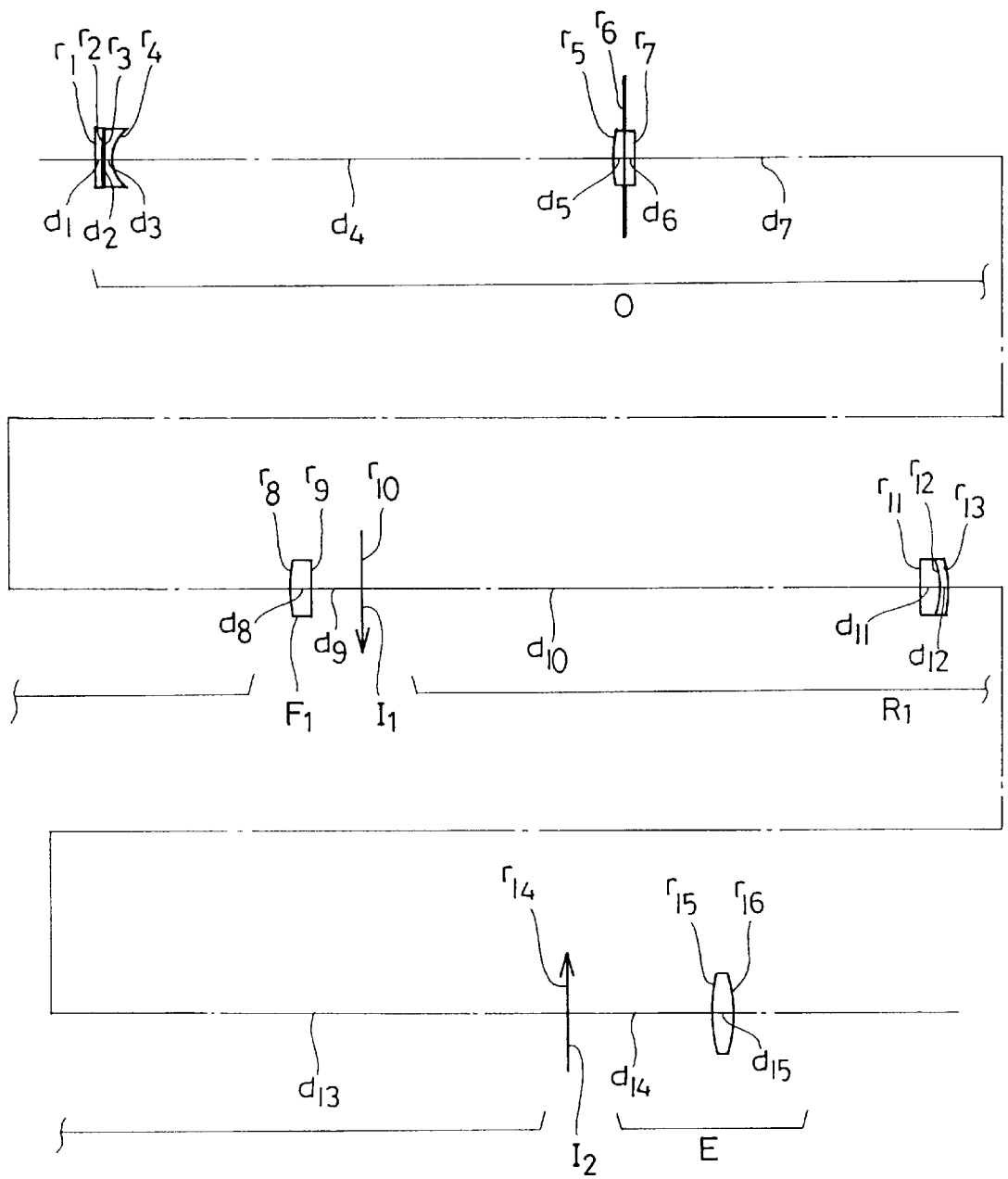
FIG. 16 shows a sectional view illustrating a composition of a seventh embodiment of the non-flexible endoscope according to the present invention.

The seventh embodiment has a composition illustrated in FIG. 16 which is similar to that of the fifth embodiment, except for a first lens component of the objective lens system O which is composed of two negative plano-concave lens elements in the seventh embodiment. Speaking more concretely of the seventh embodiment, $r_1$ through $r_7$ correspond to the objective lens system O, $r_8$ and $r_9$ correspond to a primary field lens $F_1$, $r_{11}$ through $r_{13}$ correspond to a relay lens system $R_1$, $r_{15}$ and $r_{16}$ correspond to and eyepiece lens system E; $r_{10}$ represents a primary image $I_1$, $r_{14}$ designates a secondary image $I_2$, a distance as measured from $r_1$ to $r_{10}$ corresponds to $D_1$, and a distance as measured from $r_1$ to $r_{14}$ corresponds to $D_2$.

The seventh embodiment has aberration characteristics illustrated in FIG. 50A, FIG. 50B, FIG. 50C and FIG. 50D.

Figure 17:
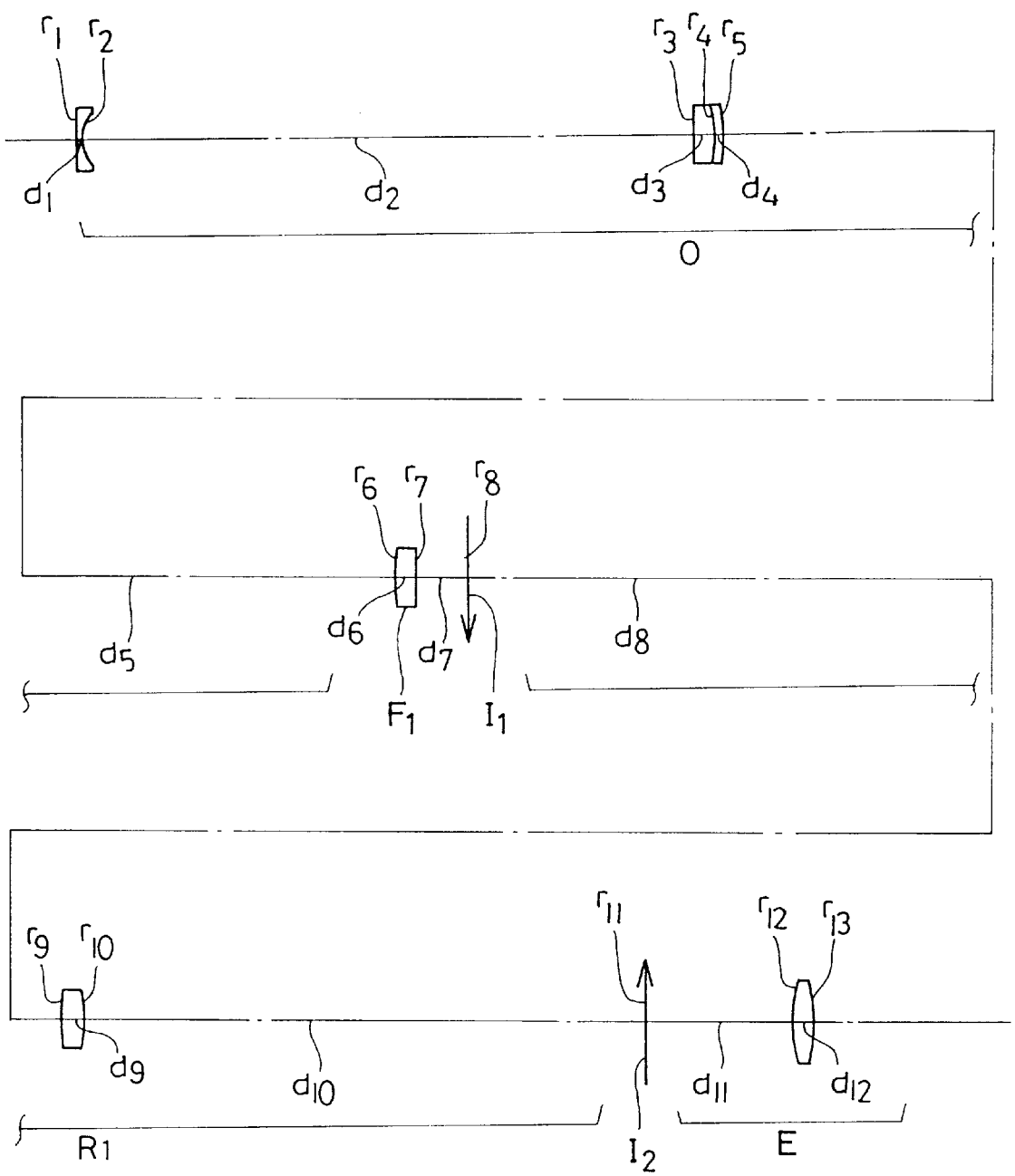
FIG. 17 shows a sectional view illustrating a composition of an eighth embodiment of the non-flexible endoscope according to the present invention.

The eighth embodiment has a composition illustrated in FIG. 17 and is different from the fifth embodiment in that a second lens component of an objective lens system O is a positive cemented lens component consisting of a positive lens element and a negative lens element, and a relay lens system $R_1$ is composed of a single positive biconvex lens element having the same radius of curvature on both surfaces thereof in the eighth embodiment. In other words, the composition of the eighth embodiment is obtained by using the cemented lens component which is disposed in the relay lens system $R_1$ as the second lens component of the objective lens system O in the composition of the fifth embodiment. Accordingly, $r_1$ through $r_5$ corresponds to the objective lens system O, $r_6$ and $r_7$ coerspnod to a primary field lens $F_1$, $r_9$ and $r_{10}$ correspond to a relay lens system $R_1$, and $r_{12}$ and $r_{13}$ correspond to an eyepiece lens system E in the eighth embodiment. Further, $r_8$ represents a primary image $I_1$, $r_{11}$ designates a secondary image $I_2$, a distance as measured from $r_1$ to $r_8$ corresponds to $D_1$, and a distance as measured from $r_1$ to $r_{11}$ corresponds to $D_2$.

The eighth embodiment has aberration characteristics which are visualized in FIG. 51A, FIG. 51B, FIG. 51C and FIG. 51D.

Figure 18:
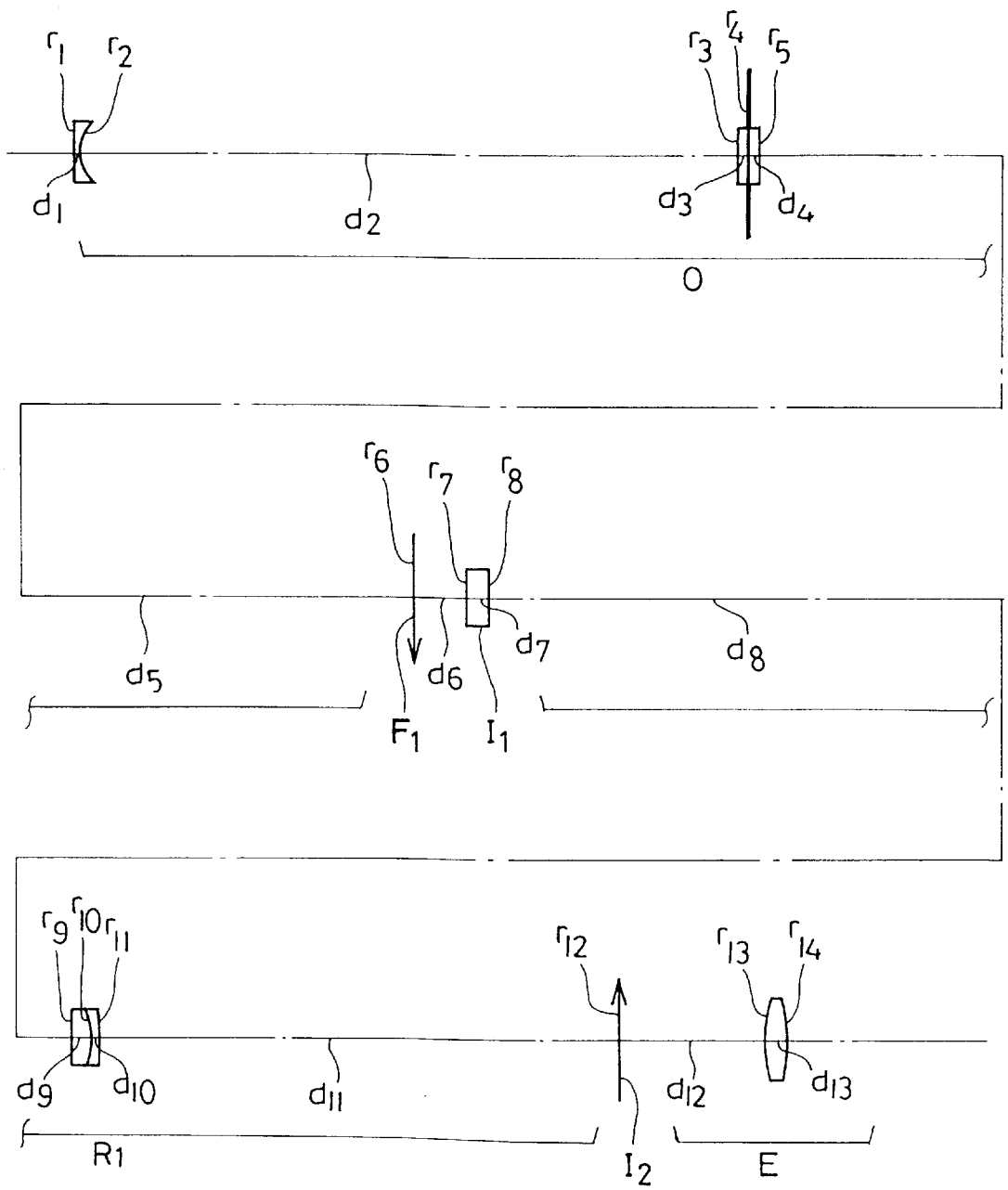
FIG. 18 shows a sectional view illustrating a composition of a ninth embodiment of the non-flexible endoscope according to the present invention.

The ninth embodiment has a composition illustrated in FIG. 18 which is similar to that of the fifth embodiment, except for a primary field lens $F_1$ which is disposed on the side of a relay lens system $R_1$, or the right side of a primary image $I_1$ in the ninth embodiment. Speaking concretely, $r_1$ through $r_5$ correspond to an objective lens system O, $r_7$ and $r_8$ correspond to the primary field lens $F_1$, $r_9$ through $r_{11}$ correspond to the relay lens system $R_1$, and $r_{13}$ and $r_{14}$ correspond to an eyepiece lens system E in the ninth embodiment. Further, a distance as measured from $r_1$ to $r_6$ corresponds to $D_1$ and a distance as measured from $r_1$ to $r_{12}$ corresponds to $D_2$.

Aberration characteristics of the ninth embodiment are visualized in FIG. 52A, FIG. 52B, FIG. 52C and FIG. 52D.

Figure 19:
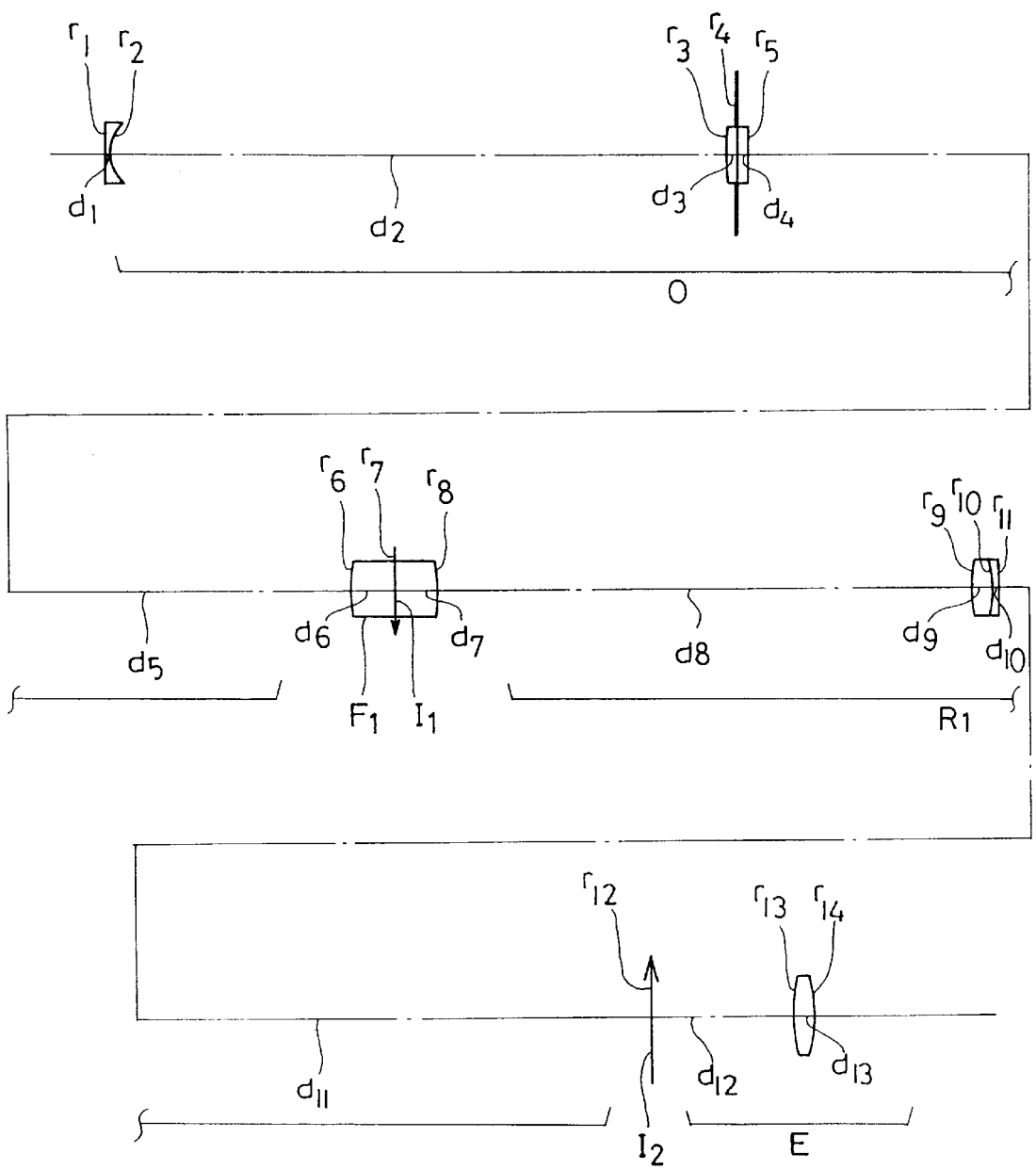
FIG. 19 shows a sectional view illustrating a composition of a tenth embodiment of the non-flexible endoscope according to the present invention.

The tenth embodiment has a composition illustrated in FIG. 19 which is characterized in that a primary image is formed in a primary field lens $F_1$. Accordingly, $r_1$ through $r_5$ correspond to an objective lens system O, $r_6$ through $r_8$ correspond to the primary field lens $F_1$, $r_9$ through $r_{11}$ correspond to a relay lens system $R_1$, and $r_{13}$ and $r_{14}$ correspond to an eyepiece lens system E. Further, $r_{17}$ represents a primary image $I_1$ formed in the primary field lens $F_1$ and $r_{12}$ designates a secondary image $I_2$.

Figures 53A, 53B, 53C, 53D:
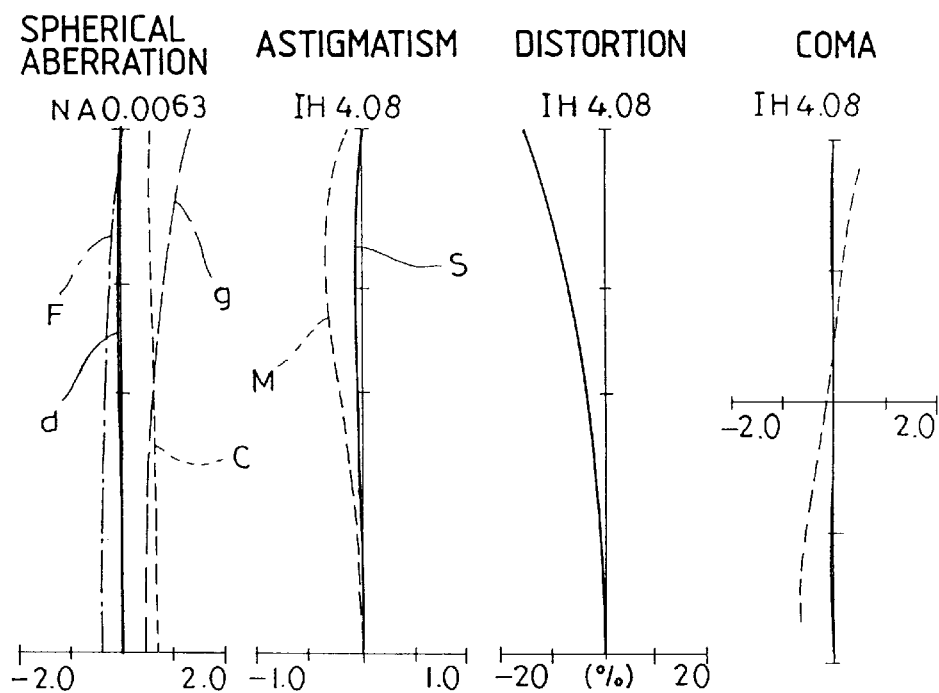
FIG. 53A, FIG. 53B, FIG. 53C and FIG. 53D show graphs illustrating aberration characteristics of an optical system used in the tenth embodiment of the non-flexible endoscope according to the present invention.

The tenth embodiment has aberration characteristics visualized in FIG. 53A, FIG. 53B, Fib. 53C and FIG. 53D.

The eleventh embodiment has a composition illustrated in FIG. 20 which is similar to that of the fifth embodiment wherein a distance as measured from $r_1$ to $r_8$ corresponds to $D_1$ and a distance as measured from $r_1$ to $r_{12}$ corresponds to $D_2$. The eleventh embodiment uses aspherical surfaces on a first lens component and a second lens component of an objective lens system. Speaking more concretely, the eleventh embodiment adopts the aspherical surfaces as a surface $r_2$ of the first lens component which is disposed on the side of the second lens component and both $r_3$, $r_5$ surface of the second lens component. Further, the eleventh embodiment is designed on an assumption that all the lens elements other than those used for composing the cemented lens comopnent are to be made of an acrylic plastic material for reducing a manufacturing cost of the non-flexible endoscope according to the present invention through mass production. Furthermore, a concave surface $r_2$ of the first lens component of the objective lens system is configured as an aspherical surface having such a shape as to lower curvature toward a margin thereof for correcting distortion.

The aspherical surfaces used in the eleventh embodiment have shapes which are expressed by the above-mentioned formula (a).

Aspherical surfaces used in the other embodiments of the present invention also have shapes expressed by this formula.

The eleventh embodiment has aberration characteristics shown in FIG. 54A, FIG. 54B, FIG. 54C and FIG. 54D.

Figure 21:
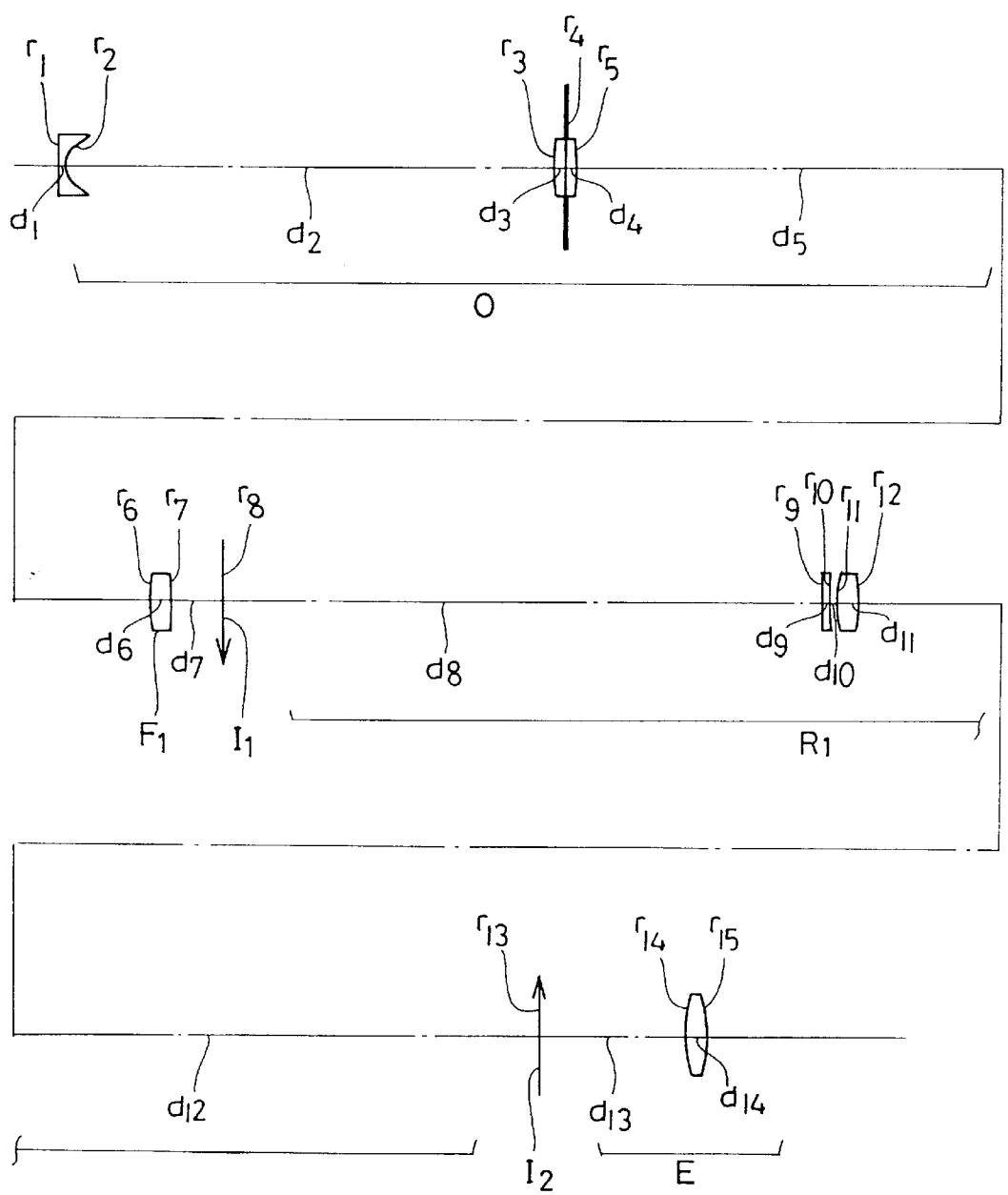
FIG. 21 shows a sectional view illustrating a composition of a twelfth embodiment of the non-flexible endoscope according to the present invention.

The twelfth embodiment has a composition visualized in FIG. 21 and is different from the fifth embodiment in that the twelfth embodiment uses a relay lens unit $R_1$ which is composed on a negative lens element and a positive lens element disposed separately, and has a positive refractive power. Speaking concretely, $r_1$ through $r_5$ correspond to an objective lens system O, $r_6$ and $r_7$ represent a primary field lens $F_1$, $r_9$ through $r_{12}$ correspond to the relay lens unit $R_1$, and $r_{14}$ and $r_{15}$ designate an eyepiece lens system E. Further, $r_8$ denotes a primary image $I_1$, $r_{13}$ represents a secondary image $I_2$, a distance as measured from $r_1$ to $r_8$ corresponds to $D_1$ and a distance as measured from $r_1$ to $r_{13}$ corresponds to $D_2$. Furthermore, a concave surface $r_2$ of a first lens component of the objective lens system O which is located on the side of a second lens component, and both surfaces $r_{11}$ and $r_{12}$ of the positive lens element of the relay lens unit $R_1$ are configured as aspherical surfaces. Moreover, all the lens elements other than the negative lens element ($r_9$ and $r_{10}$) of the relay lens unit $R_1$ are made of an acrylic plastic material for reduction of the manufacturing cost of the non-flexible endoscope according to the present invention through mass production. Like the eleventh embodiment, the twelfth embodiment uses an aspherical surface as a concave surface $r_2$ of the first lens component which is disposed on the side of the second lens component for correcting distortion.

The twelfth embodiment has aberration characteristics visualized in FIG. 55A, FIG. 55B, FIG. 55C and FIG. 55D.

Figure 22:
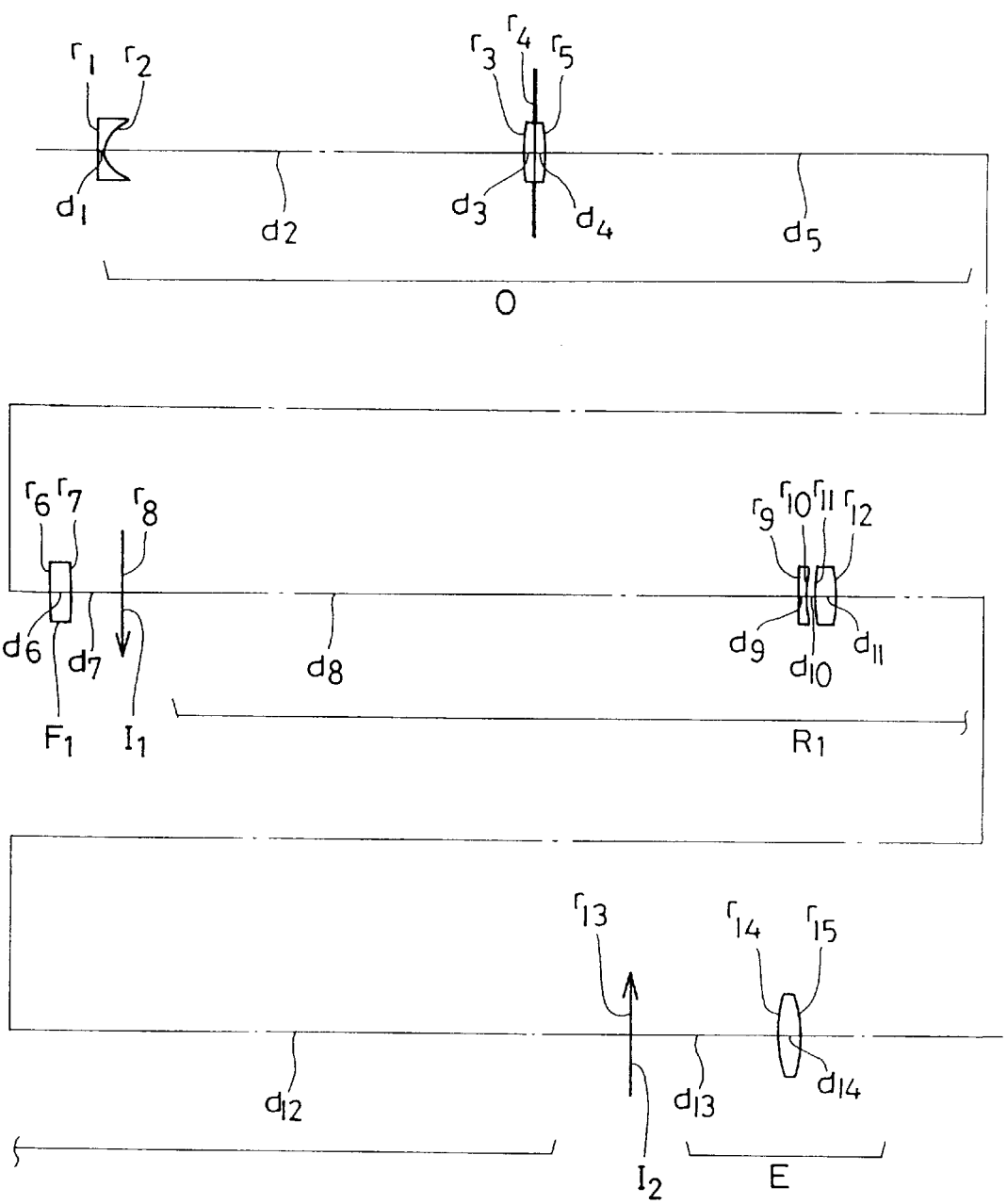
FIG. 22 shows a sectional view illustrating a composition of a thirteenth embodiment of the non-flexible endoscope according to the present invention.

The thirteenth embodiment has a composition illustrated in FIG. 22 and uses, like the twelfth embodiment, a relay lens unit $R_1$ which is composed of a negative lens element and a positive lens element disposed separately. Speaking concretely, $r_1$ through $r_5$ correspond to an objective lens system O, $r_6$ and $r_7$ represent a primary field lens $F_1$, $r_9$ through $r_{12}$ correspond to the relay lens unit $R_1$, $r_{14}$ and $r_{15}$ designate an eyepiece lens system E, $r_8$ denotes a primary image $I_1$, $r_{13}$ represents a secondary image $I_2$, a distance as measured from $r_1$ to $r_8$ corresponds to $D_1$, and a distance as measured from $r_1$ to $r_{13}$ corresponds to $D_2$. Further, a surface $r_2$ of a first lens component of the objective lens system O which is disposed on the side of a second lens component thereof, and both surfaces $r_{11}$ and $r_{12}$ of the positive lens elemenet of the relay lens unit $R_1$ are configured as aspherical surfaces. The thirteenth embodiment is configured on an assumption that all lens elements to be used for composing the optical system are to be made of plastic materials: the negative lens element of the relay lens system $R_1$ which is disposed on the side of the primary image $I_1$ to be made of a polycarbonate material and the other lens elements to be made of an acrylic plastic material.

Aberration characteristics of the thirteenth embodiment are visualized in FIG. 56A, FIG. 56B, FIG. 56C and FIG. 56D.

Figure 23:
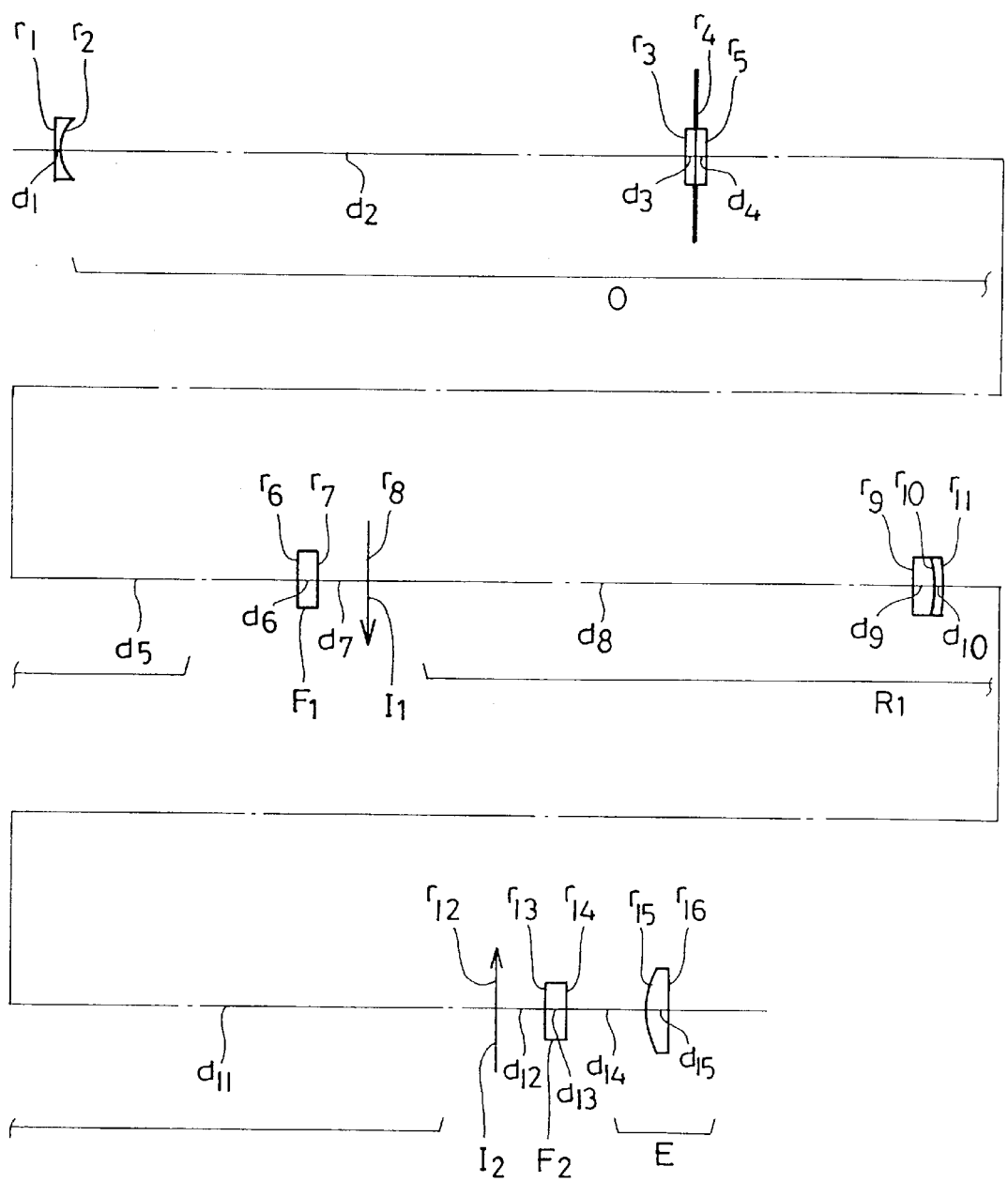
FIG. 23 shows a sectional view illustrating a composition of a fourteenth embodiment of the non-flexible endoscope according to the present invention.

The fourteenth embodiment has a composition illustrated in FIG. 23 and is different from the fifth embodiment in that the fourteenth embodiment uses a secondary field lens $F_2$ ($r_{13}$ and $r_{14}$) which is disposed on the side of an eyepiece lens system E, or right side, of a secondary image $r_{12}$. In the fourteenth embodiment, $r_1$ through $r_5$ correspond to an objective lens system O, $r_6$ and $r_7$ represent a primary field lens $F_1$, $r_9$ through $r_{11}$ correspond to a relay lens unit $R_1$, $r_{13}$ and $r_{14}$ designate the above-mentioned secondary field lens $F_2$, $r_{15}$ and $r_{16}$ denote an eyepiece lens system E, $r_8$ represents a primary image $I_1$, $r_{12}$ designates a secondary image $I_2$, a distance as measured from $r_1$ to $r_8$ corresponds to $D_1$, and a distance as measured from $r_1$ to $r_{12}$ corresponds to $D_2$.

The fourteenth embodiment which uses the secondary field lens $F_2$ permits controlling a distance as measured from the eyepiece lens system E to an eyepiece attaching surface, or allows this distance to be shorter than the distances corresponding thereto in the other embodimetns.

The fourteenth embodiment has aberration characteristics which are visualized in FIG. 57A, FIG. 57B, FIG. 57C and FIG. 57D.

Figure 24:
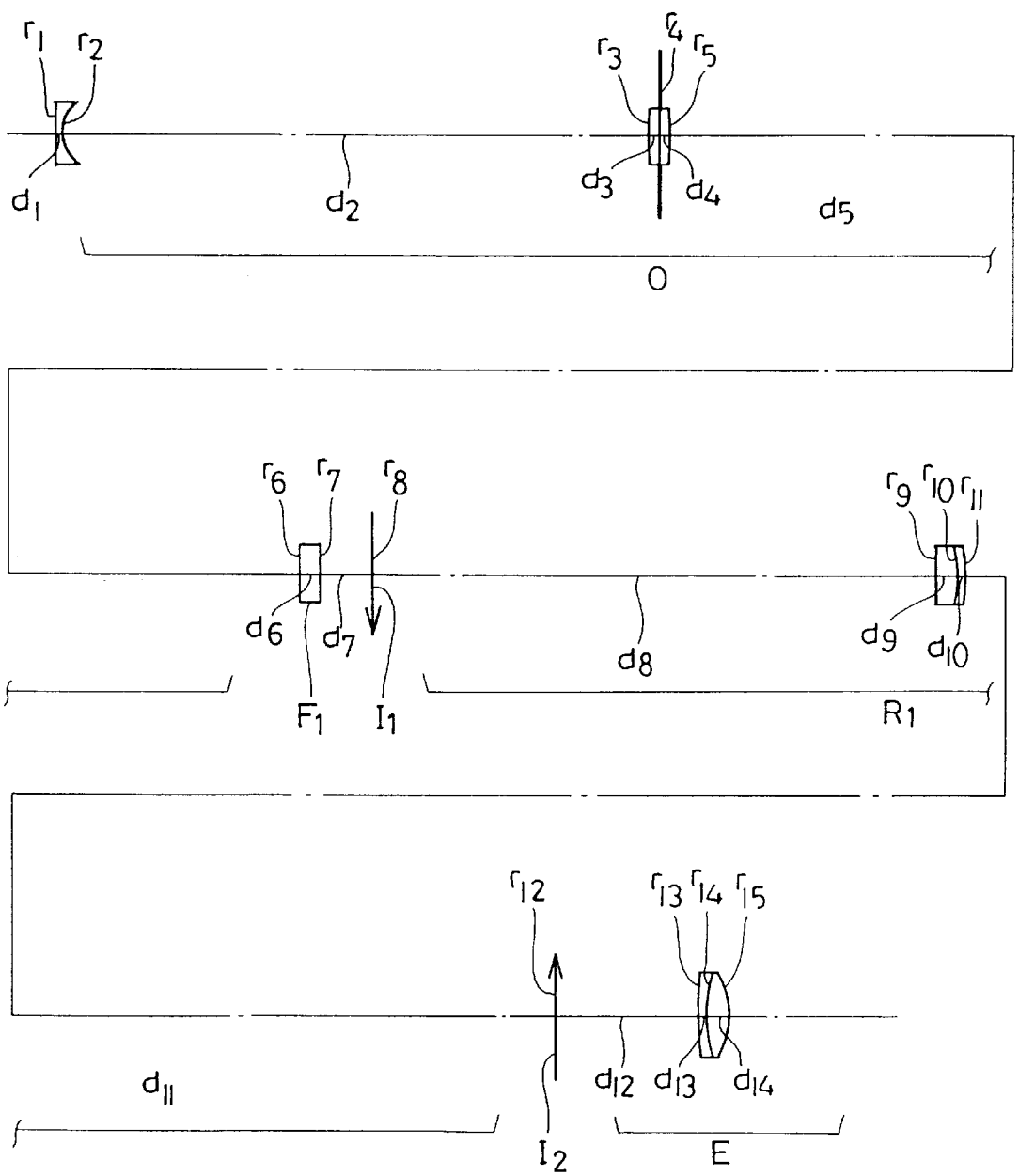
FIG. 24 shows a sectional view illustrating a composition of a fifteenth embodiment of the non-flexible endoscope according to the present invention.

The fifteenth embodiment has a composition illustrated in FIG. 24 and is characterized in that an eyepiece lens system E is composed of a cemented lens component consisting of a negative lens element and a positive lens element. Speaking concretely of the fifteenth embodiment, $r_1$ through $r_5$ correspond to an objective lens system O, $r_6$ and $r_7$ represent a primary field lens $F_1$, $r_9$ through $r_{11}$ correspond to a relay lens unit $R_1$, and $r_{13}$ through $r_{15}$ correspond to an eyepiece lens system E. Further, $r_8$ represents a primary image $I_1$, $r_{12}$ represents a secondary image $I_2$, a dsitance as measured from $r_1$ to $r_8$ corresponds to $D_1$ and a distance as measured from $r_1$ to $r_{12}$ corresponds to $D_2$.

Aberratin characteristics of the fifteenth embodiment are illustrated in FIG. 58A, FIG. 58B, FIG. 58C and FIG. 58D.

Figure 25:
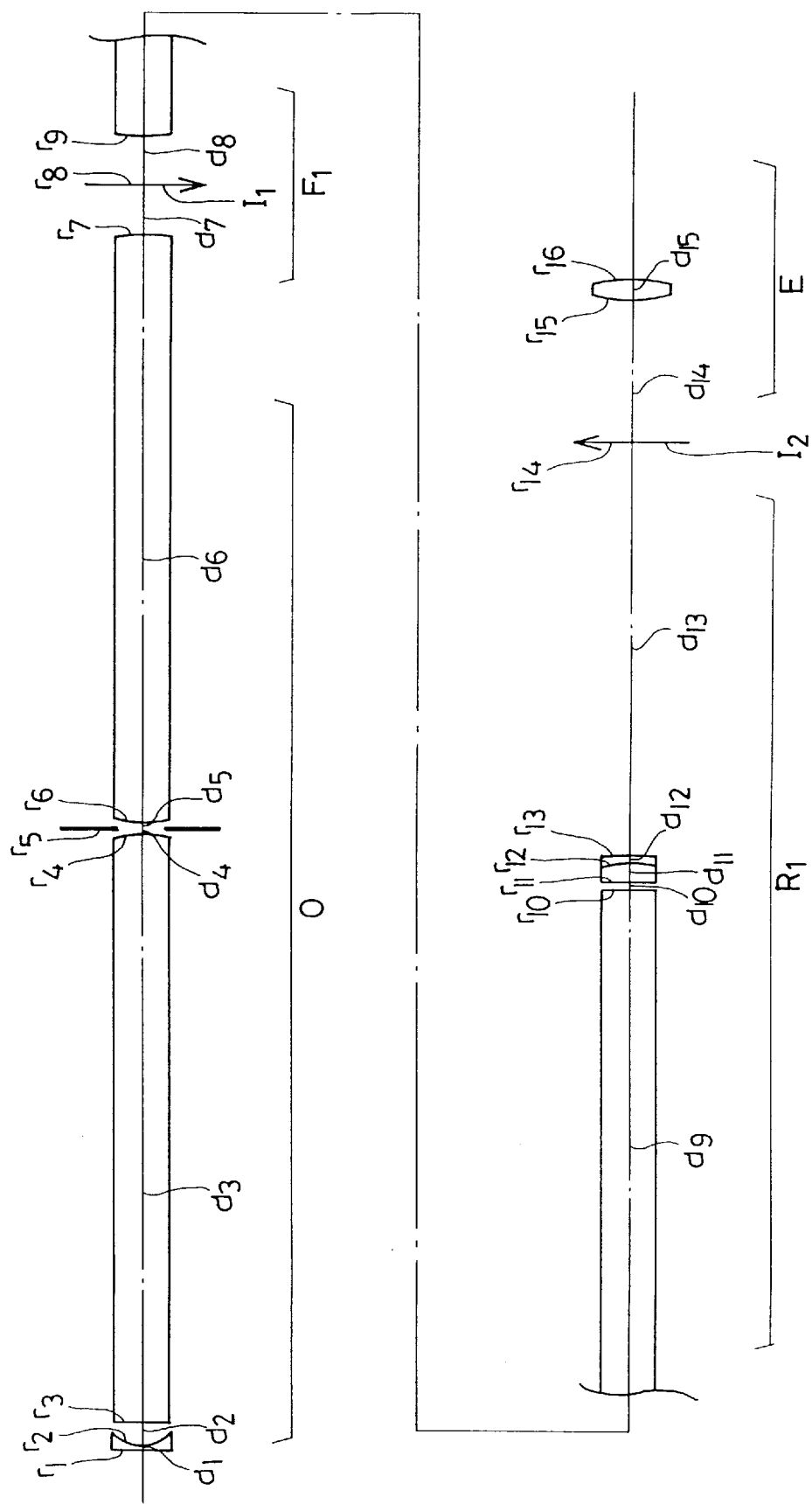
FIG. 25 shows a sectional view illustrating a composition of a sixteenth embodiment of the non-flexible endoscope according to the present invention.

The sixteenth embodiment has a composition illustrated in FIG. 25 and is characterized in that an objective lens system O and a relay lens unit $R_1$ thereof comprise long rod-shaped lens components. Speaking concretely of the optical system preferred as the sixteenth embodiment, the objective lens system and the eyepiece lens system are composed of a negative plano-concave lens element, a first biconvex rod-shaped lens component, a second biconvex rod-shaped lens component, a third convex-planar rod-shaped lens component, and a cemented lens component consisting of a positive lens element and a negative lens element. A pupil is located between the first and second rod-shaped lens components.

In the sixteenth embodiment, certain lens elements are replaced with air lenses. An airspace reserve between a surface of emergence ($r_4$) of the first rod-shaped lens component and a surface of incidence ($r_6$) of the second rod-shaped lens component functions as a biconcave air lens having a positive refractive power so that the objective lens system O is composed of a first lens component which consists of the plano-concave lens element ($r_1$ and $r_2$) and a surface of incidence of the first rod-shaped lens component, and a second lens component which consists of the air lens. Further, an airspace reserved between a surface of emergence ($r_7$) of the second rod-shaped lens component and a surface of incidence ($r_9$) of the third rod-shaped lens component forms rather a thick biconcave air lens which functions as a primary field lens $F_1$ in which a primary image $I_1$ is-to be formed. The relay lens unit $R_1$ is composed of a surface of emergence ($r_{10}$) of the third rod-shaped lens component and a cemented lens component ($r_{11}$ through $r_{13}$) to which all of a refractive power of the relay lens unit is imparted.

In addition, an eyepiece lens system E is composed of a positive biconvex lens element ($r_{15}$ and $r_{16}$). The reference symbol $r_8$ represents a primary image $I_1$, the reference symbol $r_{14}$ designates a secondary image $I_2$, a distance as measured from $r_1$ to $r_8$ corresponds to $D_1$ and a distance as measured from $r_1$ to $r_{14}$ corresponds to $D_2$.

In the field of optical systems for non-flexible endoscopes, it is conventionally known that brightness can be enhanced by filling internal spaces thereof with glass materials and this conventional technique is applies to the sixteenth embodiment of the present invention.

The sixteenth embodiment, in which the airspaces reserved in each of the fifth to fifteenth embodiments are filled with a glass material having a high refractive index, provides an effect equivalent to shortening of an effective length of an insert section calculated in terms of an optical path length, whereby the sixteenth embodiment has a larger numerical aperture or is a brighter optical system. The sixteenth embodiment actually has an F number which is smaller than the F number of any one of the fifth to fifteenth embodiments.

Though the objective lens system O, the primary field lens $F_1$ and the relay lens unit $R_1$ are composed of the thin lens elements in each of the fifth to fifteenth embodiments, it is possible to use air lenses formed among three long rod-shaped lens components as in the case of the sixteenth embodiment.

From a fact that the sixteenth embodiment has a composition which is similar to that illustrated in FIG. 13A when it is decomposed into the individual refracting surfaces, it will be understood that the sixteenth embodiment can accomplish the objects of the present invention.

The sixteenth embodiment has aberration characteristics which are visualized in FIG. 59A, FIG. 59B, FIG. 59C and FIG. 59D.

Figure 26:
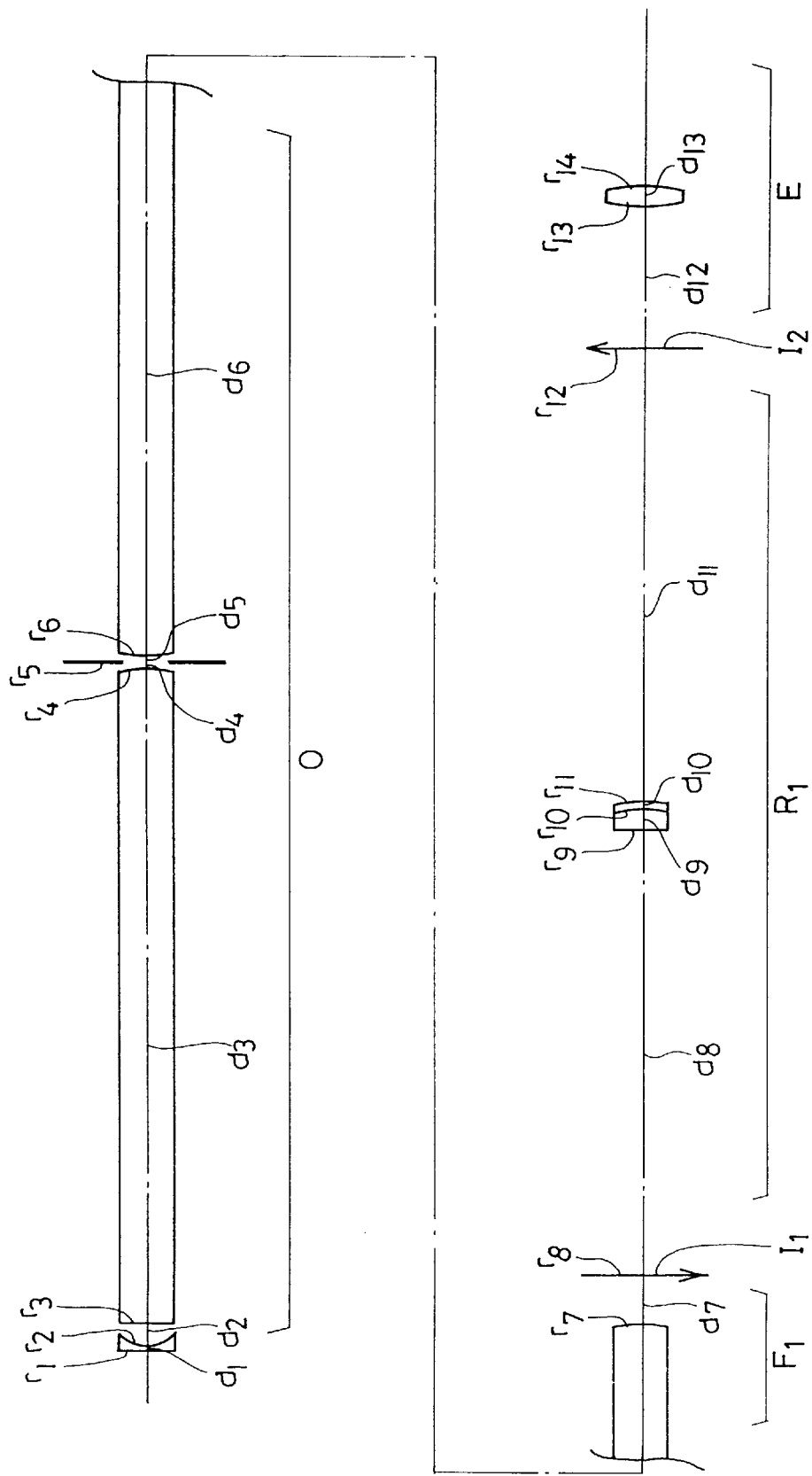
FIG. 26 shows a sectional view illustrating a composition of a seventeenth embodiment of the non-flexible endoscope according to the present invention.

The seventeenth embodiment has a composition illustrated in FIG. 26. From a viewpoint of the composition, the seventeenth embodiment is equivalent to the sixteenth embodiment in which the third rod-shaped lens component is omitted. Accordingly, an objective lens system O is composed of a first lens component which consists of a single negative plano-concave lens element ($r_1$ and $r_2$) and a surface of incidence ($r_3$) of a first rod-shaped lens component, and a second lens component which consists of an air lens ($r_4$ and $r_6$) formed between the first rod-shaped lens component and a second rod-shaped lens component in the seventeenth embodiment. A first field lens $F_1$ is composed of a surface of emergence ($r_7$) of the second rod-shaped lens component. In the specification of the non-flexible endoscope according to the present invention, a term "lens" may be used for expressing a refracting surface which has a refractive power. A relay lens unit $R_1$ is composed of a cemented lens component ($r_9$ through $r_{11}$) which consists of a positive lens element and a negative lens element. An eyepiece lens system $E_1$ is composed of a single positive biconvex lens element which has the same radius of curvature on both surfaces thereof.

The seventeenth embodiment is configured so as to have an F number which is as small as that of the sixteenth embodiment by composing the objective lens system O and the primary field lens $F_1$ of the long rod-shaped lens components. Though the primary field lens $F_1$ is composed not of a single lens element but of a single refracting surface, the seventeenth embodiment has such a refractive power distribution as that shown in FIG. 13A and can accomplish the objects of the present invention.

In addition, a distance as measured from $r_1$ to $r_8$ corresponds to $D_1$ and a distance as measured from $r_1$ to $r_{12}$ corresponds to $D_2$. Aberration characteristics of the seventeenth embodiment are visualized in FIG. 60A, FIG. 60B, FIG. 60C and FIG. 60D.

The sixteenth embodiment and the seventeenth embodiment use the long rod-shaped lens components. These long rod-shaped lens components need not be used as described with reference to these embodiments, but may be optionally disposed between the first lens component of the objective lens system and the secondary image $I_2$. These long rod-shaped lens components may be used so as to fill almost all spaces reserved between the first lens component of the objective lens system and the secondary image for brightening the optical systems or so as to fill only portions of the spaces so far as refractive power distributions are such as that shown in FIG. 13A.

Figure 27:
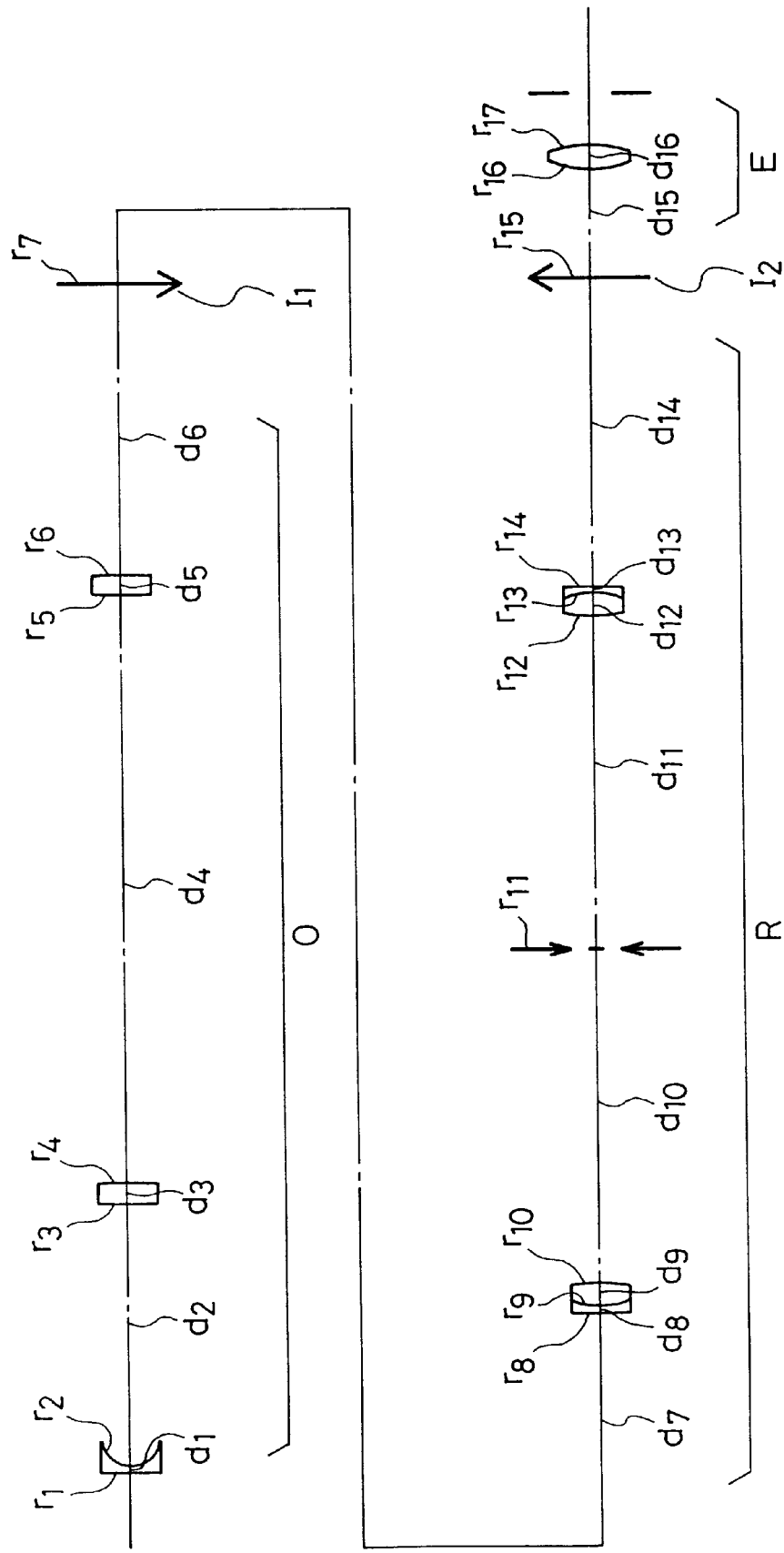
FIG. 27 shows a sectional view illustrating a composition of an eighteenth embodiment of the non-flexible endoscope according to the present invention.

The eighteenth embodiment has a composition illustrated in FIG. 27. In the eighteenth embodiment, an objective lens system O ($r_1$ through $r_6$) is composed of a first lens component consisting of a negative plano-concave lens element and a biconvex lens element, and a second lens component consisting of a single biconvex lens element; a relay lens unit $R_1$ ($r_8$ through $r_{14}$) is composed of a positive cemented lens component consisting of a negative lens element and a positive lens element, and a positive cemented lens component consisting of a positive lens element and a negative lens element; and an eyepiece lens system E ($r_{16}$ and $r_{17}$) is composed of a positive lens element.

The eighteenth embodiment uses no primary field lens and has aberration characteristics visualized in FIG. 61A, FIG. 61B, FIG. 61C and FIG. 61D.

FIG. 47A, FIG. 47B, FIG. 47C and FIG. 47D through FIG. 61A, FIG. 61B, FIG. 61C and FIG. 61D, i.e., the graphs illustrating the aberration characteristics of the sixth through eighteenth embodiments, visualize aberration characteristics of the optical systems composed of sections from the objective lens systems to the eyepiece lens system when they are combined with the imaging lens system ($r_{15}$ through $r_{30}$) used in the fifth embodiment.

Aberration characteristics only of the imaging lens system disposed in the TV camera (the imaging lens system IL shown in FIG. 14) has aberration characteristics illustrated in FIG. 62A, FIG. 62B, FIG. 62C and FIG. 62D.

Since each of the embodiments is configured so as to correct aberrations sufficiently in the optical system considered as an independent section in the non-flexible endoscope according to the present invention, the optical system as a whole has favorable aberration characteristics even when it is combined with the imaging lens system.

The above-mentioned distance $D_3$, which is a distance as measured from the primary field lens $F_1$ to the primary image $I_1$, is defined as an optical path length as measured from the primary image to a refracting surface which is disposed at a shortest distance therefrom and has a positive refractive power. In such a case as the fifth embodiment wherein the field lens $F_1$ is disposed on the side of the objective lens system of the primary image $I_1$, the distance $D_3$ corresponds to a distance as measured from a surface of the primary field lens $F_1$ which is located on the side of the relay lens unit $R_1$ to the primary image. Further, in such a case as the ninth embodiment wherein the primary field lens $F_1$ is disposed on the side of the relay lens unit $R_1$ of the primary image, the distance $D_3$ corresponds to a distance as measured from the primary image to a surface of the primary field lens $F_1$ which is located on the side of the objective lens system O. Furthermore, in such a case as the tenth embodiment wherein the primary field lens $F_1$ is disposed at a location of the primary image $I_1$ or such a case as the sixteenth embodiment wherein an air lens is used as the primary field lens $F_1$, the distance $D_3$ corresponds to a distance, expressed in terms of an optical path length, as measured from the primary image to one of surfaces of the primary field lens whichever is nearer the primary image. In addition, in the case of the eleventh embodiment or the sixteenth embodiment wherein the primary iamge $I_1$ is formed between both surfaces of the primary field lens, the distance may be measured from either of the surfaces to the primary image so far as it is unnecessary to consider a positive or negative sign of the distance $D_3$. In the seventeenth embodiment wherein the surface $r_7$ has a refractive power which has a role of the primary field lens $F_1$, the distance $D_3$ corresponds to a distance as measured from the surface $r_7$ to the primary image.

Figure 30:
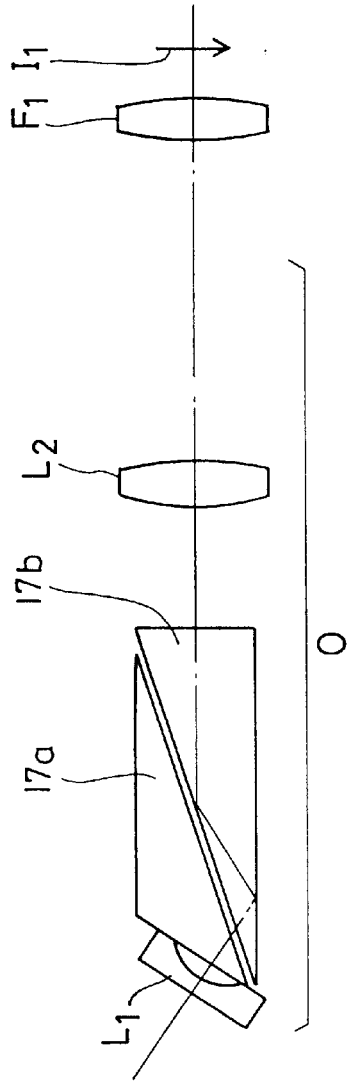
FIG. 30 shows a sectional view illustrating a configuration of prisms which are to be employed when the non-flexible endoscope according to the present invention is to be used for oblique viewing.

Though all of the fifth through seventeenth embodiments are configured for straight viewing, the optical systems preferred as these embodiments are usable also for oblique viewing. FIG. 30 shows a sectional view illustrating the composition of an objective lens system of the non-flexible endoscope configured for straight viewing which can be modified for oblique viewing by disposing prisms 17a and 17b for oblique viewing on the side of the first lens component of the objective lens system in a section between the first lens component and the second lens component thereof. A narrow space reserved between the prism 17a and the prism 17b is filled with a medium such as air or a cementing agent having a low refractive index.

Rays coming from an object pass through the first lens component of the objective lens system O and the prism 17a, transmit through the medium having the low refractive index used for filling a space between the prism 17a and the prism 17b, and are reflected by a bottom surface of the prism 17b so as to reach a slant surface of the prism 17b, where the rays are totally reflected by a boundary surface between the slant surface and the medium having the low refractive index so as to travel toward the second lens component of the objective lens system. Though it is desirable to coat the bottom surface of the prism 17b with a reflective film of a metal such a aluminium, such a metallic film is unnecessary in a case where the rays can be totally reflected by using a prism having a high refractive index. Though it is desirable to select materials having high refractive indices for the prisms 17a and 17b, such materials are limited to glass materials and hardly allow to reduce manufacturing costs of the prisms. When the non-flexible endoscope according to the present invention is to be configured so as to be disposable, a manufacturing cost thereof can be reduced by selecting optical plastic materials such as acrylic plastic materials for the prisms 17a and 17b, and manufacturing these prisms by injection molding. Since the prisms made of such materials have low refractive indices, it is necessary for assuring total reflection on the slant surface of the prism 17b to fill an airspace reserved between the prisms 17a and 17b with air.

Though it is difficult to configure the objective lens system for the optical system of the non-flexible endoscope according to the present invention, in which heights of rays are larger than those in the objective lens system for the conventional non-flexible endoscope, so as to allow to dispose prisms for oblique viewing therein, it is possible to design an optical system for oblique viewing non-flexible endoscopes by selecting the composition described above which permits reserving sufficient effective diameters in prisms.

Figure 28:
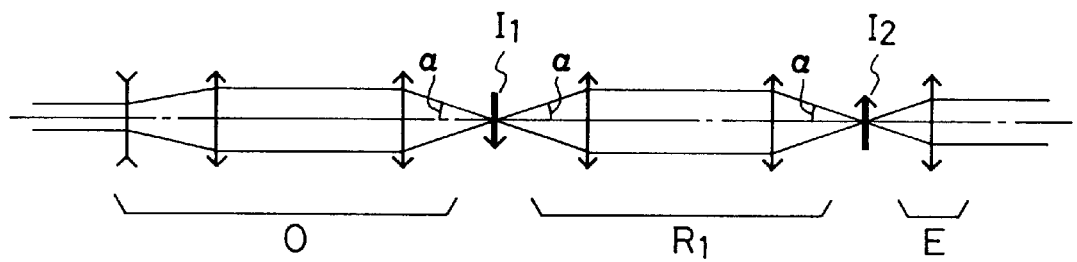
FIG. 28 shows a sectional view visualizing relationship between a primary image and a numerical aperture in the fourteenth embodiment of the present invention.
Figure 29A:
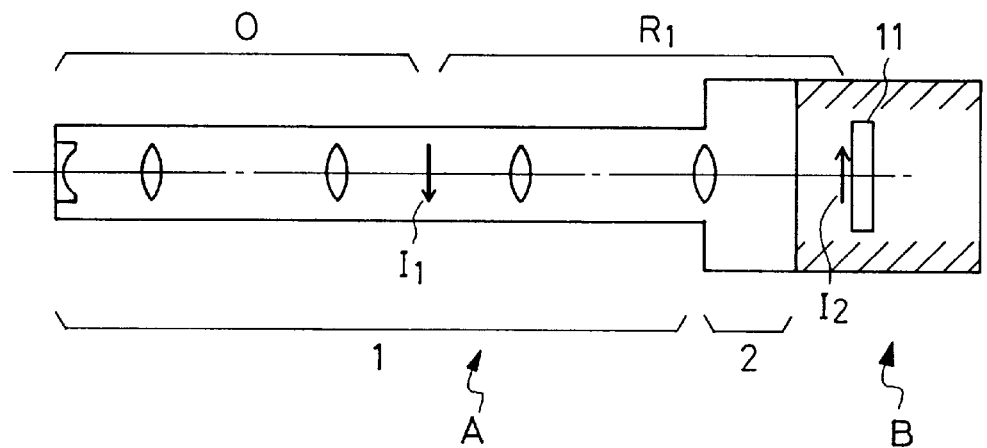
FIG. 29A and FIG. 29B show sectional views exemplifying non-flexible endoscopes comprising no eyepiece lens system.
Figure 29B:
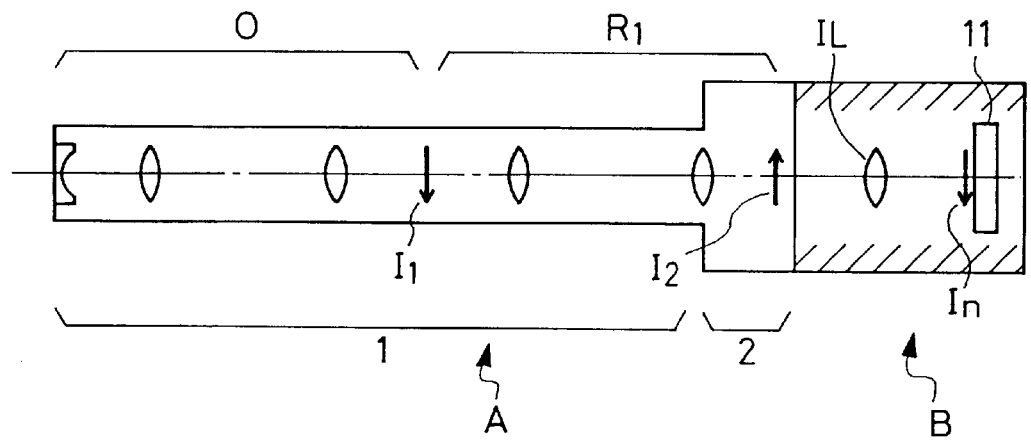

The optical system of the non-flexible endoscope according to the present invention of the type which accommodates the objective lens system and the relay lens system also comprises the eyepiece lens system E as shown in FIG. 28. That is to say, the eyepiece lens system E is disposed after the secondary image $I_2$ as shown in FIG. 28. However, the eyepiece lens system E may not be used as illustrated in FIG. 29A and FIG. 29B. In other words, the secondary image $I_2$ can be picked up directly by the solid-state image pickup device 11. In this case, the observation optical system disposed in an non-flexible endoscope consists only of the objective lens system O and the relay lens system $R_1$, and the solid-state image pickup device 11 is disposed in the TV camera B for directly picking up the secondary image $I_2$.

By selecting the configuration described above for the non-flexible endoscope from which the insertion section 1, the grip section 5 and the TV camera system 6 are detachable, it is pssible to obtain a merit that the endoscope has a simple configuration and is disposable at a low cost. Even when the non-flexible endoscope is not discarded, it can be exchanged with another non-flexible endoscope. Further, the endoscope can be configured so as to be bearable of autoclaving since it can have a configuration comprising no electrical system. Moreover, it is possible to obtain a non-flexible video scope by integrating the non-flexible endoscope with the TV camera.

FIG. 29B shows an optical system which is configured so as to perform an additional relay cycle for the secondary image $I_2$ before image pickup. Speaking concretely, an imaging lens system IL is disposed in a TV camera B so as to allow an image pickup device 11 to pickup an image. The configuration illustrated in FIG. 29B like that shown in FIG. 29A, allows the TV camera to be detached from the non-flexible endoscope or to integrate the TV camera with the non-flexible endoscope.

The above-mentioned condition (9) should be satisfied also in the configuration illustrated in FIG. 29A or FIG. 29B. In this case, the optical system of the non-flexible endoscope according to the present invention comprises an objective lens system and a relay lens system which are disposed in order from the leading end in a slender insert section; is configured so that the objective lens system forms a primary image in the insert section and the relay lens system forms a secondary image by relaying the primary image; and satisfies the condition (9). Further, the non-flexible endoscope according to the present invention can comprise an image pickup device for picking up the secondary image or an imaging lens system for further relaying the secondary image and an image pickup device for picking up an image $I_n$ formed by the imaging lens system. Each of the non-flexible endoscopes satisfies the condition (5).

Now, description will be made of another type of optical system which is desirable for use in the non-flexible endoscope according to the present invention and comprises a relay lens system performing a single of a plurality of cycles of image relayings.

The optical system of the non-flexible endoscope according to the present invention of the type using the above-mentioned relay lens system consists of: an objective lens system which is disposed in a leading end of a slender insert section to be inserted into cavities of living bodies for observing interiors thereof so as to form a primary image; and a relay lens system which is disposed in the insert section so as to relay the primary image in a single or a plurality of cycles for forming a final image in the vicinity of a near end of the insert section or in a grip section attached to the insert section. This optical system is also configured so as to satisfy the above-mentioned condition (9).

Figure 1:
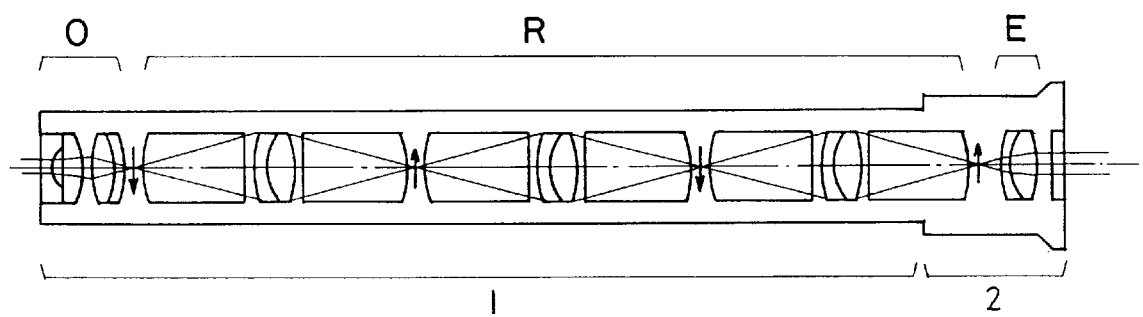
FIG. 1 shows a sectional view illustrating a composition of a conventional optical system for non-flexible endoscopes.

The non-flexible endoscope according to the present invention which uses the optical system described above is similar to the conventional endoscope having the eyepiece section 2 illustrated in FIG. 1. That is to say, the non-flexible endoscope according to the present invention which uses the optical system described above has a configuration shown in FIG. 31 wherein the endoscope consists of a slender insert section 1 to be inserted into cavities of living bodies and the like, and a grip section 5 which is to be kept outside the cavities even during use of the non-flexible endoscope and has a near end configured as an eyepiece section 2.

The optical system of the non-flexible endoscope according to the present invention consists, for example, of an objective lens system O disposed in the leading end of the insert section 1, a relay lens system R for relaying a primary image $I_1$ formed by the objective lens system O and an eyepiece lens system E disposed in the eyepiece section 2 for forming a nearly parallel light bundle from rays which come from a final image $I_n$ formed by the relay lens system R.

Figure 32:
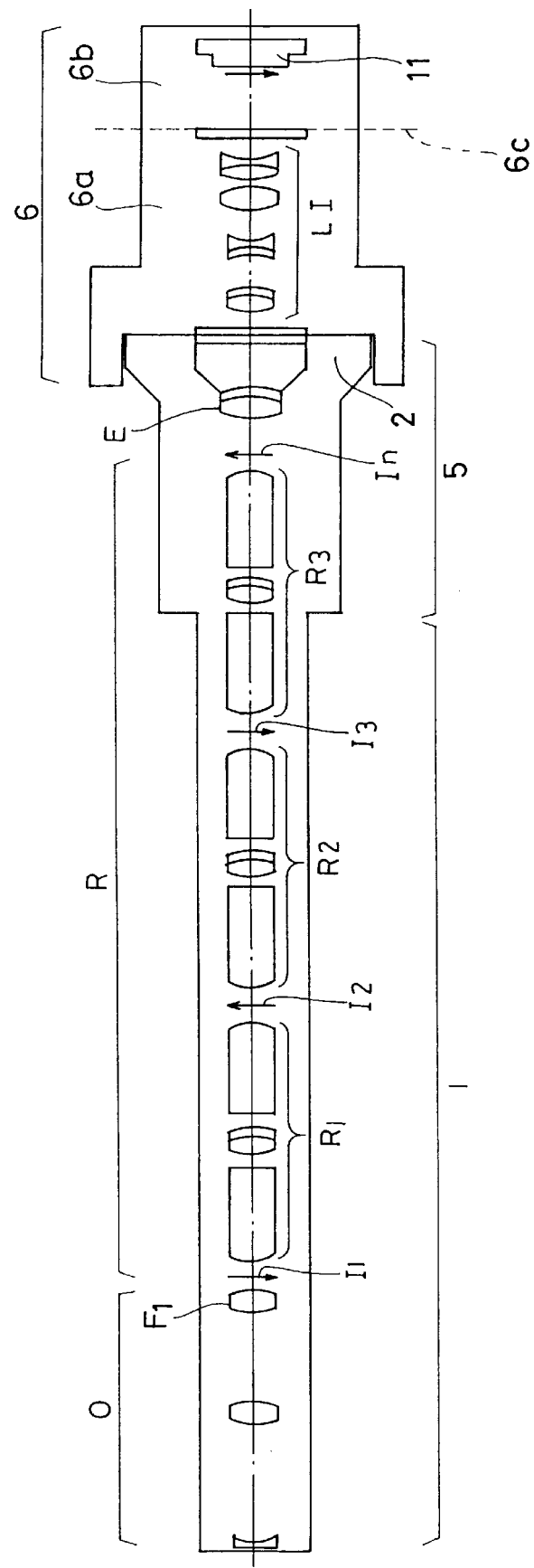
FIG. 32 shows a sectional view illustrating a twentieth embodiment of the non-flexible endoscope according to the present invention.

Further, the non-flexible endoscope according to the present invention permits attaching a TV camera system 6 for endoscopes which is configured separately from the grip section 5 to the eyepiece section 2 as shown in FIG. 32. Disposed in this TV camera system 6 are an imaging lens system IL and a solid-state image pickup device 11. Though the non-flexible endoscope shown in FIG. 32 uses the TV camera system 6 which is mechanically integrated, this TV camera system may be divided along a dashed line 6c shown in FIG. 32 so as to compose an adaptor 6a comprising the imaging lens system IL and a TV camera head 6b comprising the solid-state image pickup device 11, and the adaptor 6b and the TV camera head 6b can be configured so as to be mechanically attachable and detachable to and from each other. When the adaptor 3 and the TV camera head 6a are configured so as to be attachable and detachable, it is possible to perform photographing by using various combinations of these members each of which is prepared in a plurality of kinds.

Figure 31:
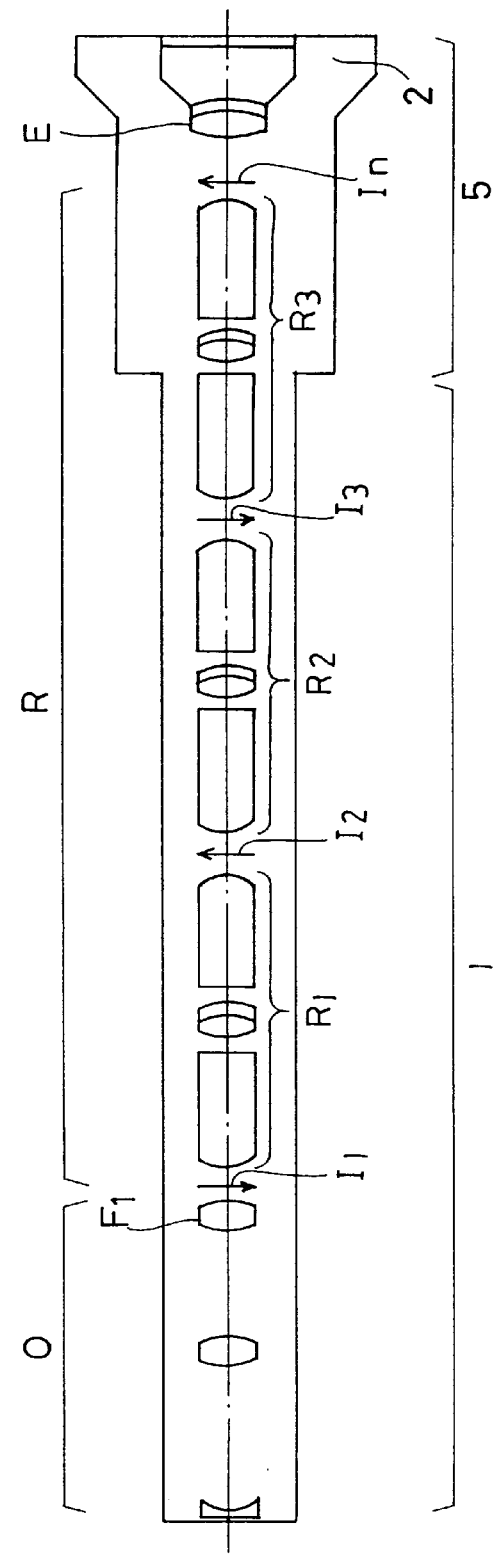
FIG. 31 shows a sectional view illustrating a composition of a nineteenth embodiment of the non-flexible endoscope according to the present invention.

The optical system of the non-flexible endoscope according to the present invention is composed, as shown in FIG. 31 or FIG. 32 for example, of the objective lens system O which is disposed on the side of the leading end in the insert section 1 for forming the primary image $I_1$ in the insert section 1, a relay lens system R for relaying the primary image $I_1$ in a single or a plurality of cycles so as to form a final image $I_n$ in the near end of the insert section 1 or the grip section 5, and an eyepiece lens system E which is disposed in the eyepiece section 2 of the grip section 5 for allowing rays incident from the final image $I_n$ to emerge in a condition of a nearly parallel light bundle which is observable by naked eyes.

Now, description will be made of the optical system for the non-flexible endoscope which has the composition described above and is configured so as to perform three cycles of image relaying as shown in FIG. 31 or FIG. 32. The optical system of the non-flexible endoscope according to the present invention is characterized in that the above-mentioned distances $D_1$ and $D_R$ are nearly equal to each other for enlarging a numerical aperture or obtaining a bright optical system while reserving a length (an effective length) of the insert section required for the non-flexible endoscope.

As in an ordinary case where a final image which must be formed on the object side of an eyepiece lens system E is formed in the vicinity of an insertion section 1, a quaternary image shown in FIG. 31 or FIG. 32 corresponds to the final image $I_n$ in the optical system of the non-flexible endoscope according to the present invention and is formed, for example, in the grip section 5 as shown in FIG. 31 or FIG. 32. Accordingly, it is necessary that a distance as measured from the leading end of the insert section to the final image $I_n$ must be equal to or longer than an effective length of the insert section. Though a shorter distance as measured from the leading end of the insert section to the final image permits configuring a brighter optical system, the effective length of the insert section is determined nearly dependently only on a length required for surgical operations and cannot be shorter than this length.

When the optical system of the non-flexible endoscope according to the present invention is configured so as to perform three cycles of image relaying, it forms four images including the final image $I_n$ which is formed at the location determined as described above. Further, a relay lens system R is composed of relay lens unit $R_1, R_2, \ldots$ each of which relays an image at a magnification of 1x and the present invention provides a bright optical system by using the relay lens units repeatedly, and adequately selecting an objective lens system and a relay lens system as described below.

When the optical system of the non-flexible endoscope according to the present invention is configured so as to peform three cycles of image relaying as described above, for example, it forms four images including a secondary image, an intermediate image and a final image which are to be formed at locations determined for the reasons described above. Therefore, the present invention selects an adequate location for a primary image so as to obtain a bright optical system.

Figure 33A:
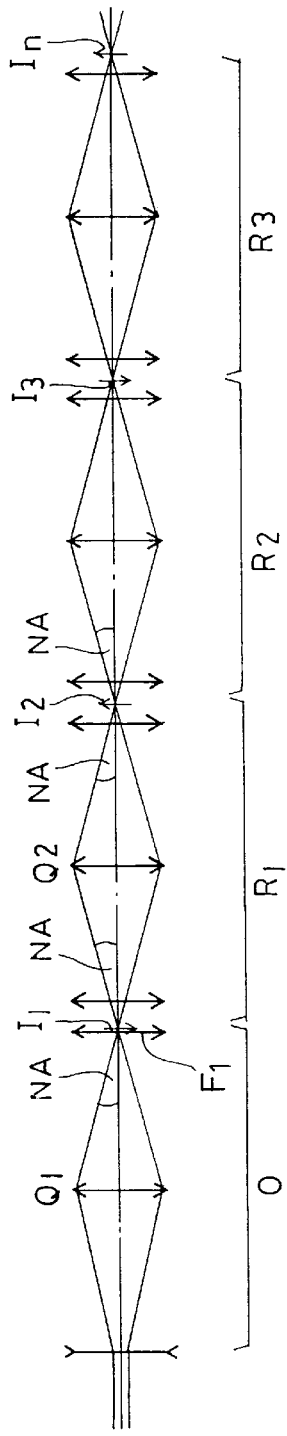
FIG. 33A, FIG. 33B and FIG. 33C show diagrams visualizing relationship between locations of primary images in an optical system for endoscopes which is configured so as to perform three cycles of image relaying and numerical apertures thereof.
Figure 33B:
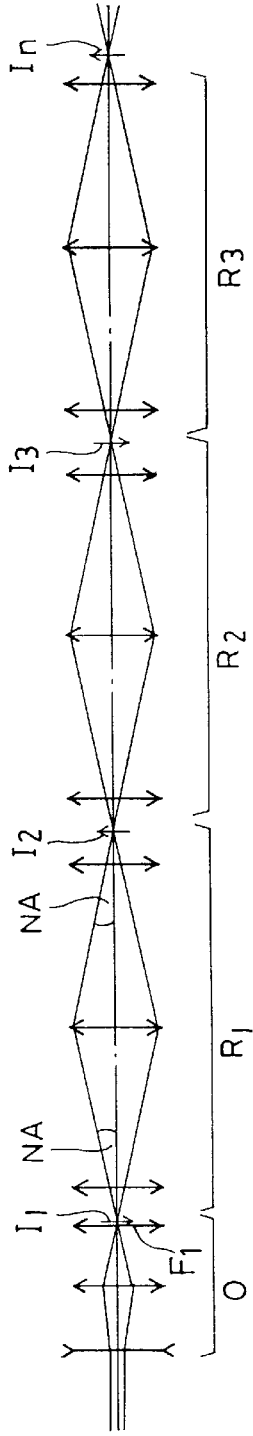
Figure 33C:
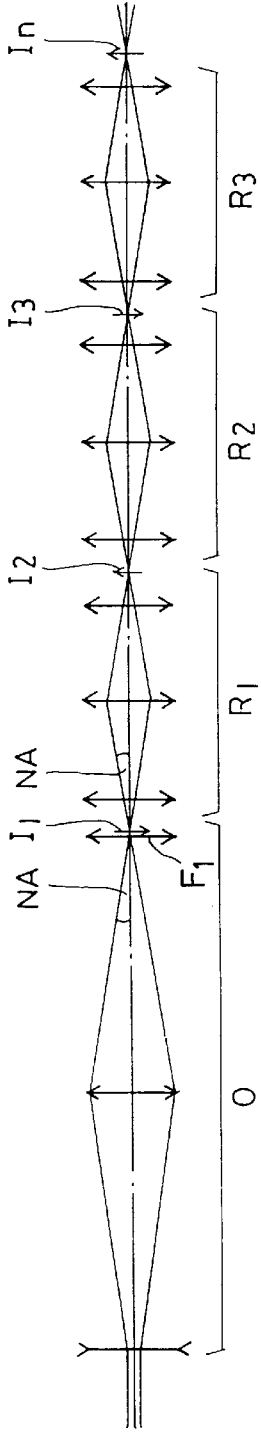

FIG. 33A, FIG. 33B and FIG. 33C show diagrams illustrating variaitons of numerical apertures to be caused by changing a location of the primary image in a typical optical system of the non-flexible endoscope according to the present invention which is configured to perform three cycles of image relaying.

FIG. 33A shows a case where the objective lens system O is prolonged so as to have a length $D_1$ which is equal to a length $D_R$ of each of relay lens units $R_1, R_2$ and $R_3$ required for a single cycle of image relaying, FIG. 33B illustrates a case where the objective lens system is shortened so as to form a primary image $I_1$ at a location shifted toward the leading end, and FIG. 33C visualizes a case where the objective lens system O is remarkably prolonged so as to form the primary image $I_1$ at a location shifted toward an intermediate image $I_2$. Out of the three cases shown in FIG. 33A, FIG. 33B and FIG. 33C, a refractive power distribution which is most desirable for accomplishing the objects of the present invention is obtained in the case shown in FIG. 33A. The case shown in FIG. 33B corresponds to a composition which is similar to that of the conventional optical system for non-flexible endoscopes using a short objective lens system.

In each of FIG. 33A, FIG. 33B and FIG. 33C, numerical apertures are equal to each other between a side of incidence and a side of emergence at the location of the primary image $I_1$ formed by the objective lens system O since each of the relay lens untis $R_a$, $R_2$ and $R_3$ of the relay lens system R is set at a magnification of 1x and the primary field lens $F_1$ is disposed at a location coincident with the primary image $I_1$. A "numerical aperture" means an angle which is formed between a marginal ray and an optical axis.

Though maximum heights of marginal rays are traced equal in FIG. 33A, FIG. 33B and FIG. 33C, it is apparent that the optical system shown in FIG. 33A has a largest numerical aperture or is brightest since a limit for heights of the marginal rays is not determined only either one of the objective lens system and the relay lens system. In the case shown in FIG. 33B, a limit for heights of the marginal rays is determined by the relay lens system and a numerical aperture is determined dependently only on a length of the relay lens system. In the case shown in FIG. 33C, in contrast, a limit for heights of the marginal rays is determined by the objective lens system and a numerical aperture is determined dependently on a length of the objective lens system.

In the case shown in FIG. 33A, the limit for heights of the marginal rays is determiend by both the objective lens system and the relay lens system, either of which has a length larger than that of the relay lens system shown in FIG. 33B or that of the objective lens system shown in FIG. 33C, thereby allowing an optical system having a given outside diameter to have a large numerical aperture.

The condition (9) is required for obtaining a large numerical aperture.

$D_1/D_R$ used in the condition (9) is a parameter for varying brightness and brightness is maximum at $D_1/D_R = 1.0$ which corresponds to the condition shown in FIG. 33A. When $D_1/D_R$ is deviated from 1.0, brightness is lowered to values listed below which are expressed taking brightness at $D_1/D_R = 1.0$ as 1:

(When $D_1/D_R < 1.0$) $[\{1+(N-1) \times D_R/D_1\}/N]^2$ (When $D_1/D_R > 1.0$) $[\{1+D_1/(N-1)/D_R\} \times (N-1)/N]^2$ wherein the reference symbol N represents a number of imaging cycles to be performed by the relay lens system.

For the optical system of the non-flexible endoscope according to the present invention which has the typical composition for three cycles of image relaying, or N=4, ratios of brightness at various values of $D_1/D_R$ relative to brightness at $D_1/D_R=1$ are calculated as listed below:

| $D_1/D_R$ | Ratio in brightness |
|---|---|
| 0.01 and 1.42 | 0.57 |
| 0.33 and 1.29 | 0.69 |
| 1.0 | 1.0 |

As is seen from the calculation values listed above, $D_1/D_R$ having a value of 0.01 or 1.42 lowers brightness to a half of that at $D_1/D_R=1.0$ below which brightness is allowed to be lowered. That is to say, if the lower limit or the upper limit of the condition (9) is exceeded, the optical system will be set in the condition shown in FIG. 33B or FIG. 33C, whereby the optical system will have brightness lower than a maximum level which is available with the utmost capability thereof and is not bright enough for practical use. Further, it is desirable, for obtaining at least 70% of the brightness available with the utmost capability of the optical system, to configure it so as to satisfy, instead of the condition (9), the following condition:

$0.33 < D_1/D_R < 1.29$

In the optical system shown in FIG. 31, the primary field lens $F_1$ which is disposed in the vicinity of the primary image $I_1$ has a function to relay a pupil of the objective lens system O to the relay lens system R. Since a principal ray emerging from the objective lens system O travels in a direction away from the optical axis, the principal ray cannot pass through the relay lens system R and an image will be eclipsed at a marginal portion of a visual field if the primary field lens $F_1$ is not disposed in the vicinity of the primary image $I_1$. It is therefore necessary to dispose the field lens $F_1$ in the vicinity of the primary image $I_1$. When an air-contact surface of the primary field lens $F_1$ is overlapped with the primary image $I_1$, however, dust or injury on the surface of the primary field lens $F_1$ will be imaged. It is therefore desirable to dispose the field lens $F_1$ so as to have air-contact surfaces located slightly apart from the primary image $I_1$.

The foregoing description which is made of the typical relay lens system configured for three cycles of image relaying (N=4) is applicable also to relay lens systems which are configured for two cycles, three cycles, four cycles, . . . n cycles of image relaying. It is desirable to select values of $D_1/D_R$ within ranges defined below so that the optical system has brightness of at least 70% of that available with the maximum capability thereof when they are configured for numbers of imaging cycles of 2, 3, 4, . . . to 10:

TABLE 3

| N (number of imaging cycle) | |
|---|---|
| 2 | $0.66 < D_1/D_R < 1.5$ |
| 3 | $0.56 < D_1/D_R < 1.29$ |
| 4 | $0.33 < D_1/D_R < 1.29$ |
| 5 | $0.3 < D_1/D_R < 1.26$ |
| 6 | $0.3 < D_1/D_R < 1.25$ |
| 7 | $0.3 < D_1/D_R < 1.25$ |
| 8 | $0.3 < D_1/D_R < 1.24$ |
| 9 | $0.3 < D_1/D_R < 1.22$ |
| 10 | $0.3 < D_1/D_R < 1.2$ |

By attaching a TV camera system for non-flexible endoscopes to the optical system of the non-flexible endoscope according to the present invention which has the fundamental composition described above, it is possible to carry out observation on a TV monitor indispensable to surgical operations under observation through endoscopes. For such observation on a TV monitor, it is sufficient to attach a TV camera system 6 to a grip section 1 as in the non-flexible endoscope-shown in FIG. 31 so that an imaging lens system IL disposed in this TV camera system forms a final image $I_n$ at a location coincident with a light receiving surface of a solid-state image pickup device 5 for picking up the final image $I_n$.

Now, description will be made below of a composition desirable for the objective lens system which is to be used in the optical system of the non-flexible endoscope according to the present invention. Speaking concretely, it is desirable to compose the objective lens system, in order from the object side, of a first lens component which is disposed in the leading end of an insert section and has a negative refractive power, and a second lens component which is disposed between the first lens component and a primary field lens $F_1$, and has a positive refractive power. This refractive power distribution in the objective lens system is desirable for composing the lens system of a reduced number of lens elements while reserving a field angle required for the objective lens system. The negative refractive power of the first lens component has a function to widen a field angle, whereas the positive refractive power of the second lens component has a role to form a real primary image by imaging a virtual image of an object which is formed by the first lens component. Since the first lens component of the objective lens system has the strongest refractive power among those of lens components disposed in an observation optical system which consists of the objective lens system and a relay lens system, the first lens component has a function to correct curvature of field. Further, the second lens component has a role to determine a pupil in the objective lens system. Accordingly, the refractive power distribution described above permits minimizing a number of lens elements required for composing the objective lens system.

The objective lens system of the optical system shown in FIG. 31, for example, is composed of the first lens component which consists of a single negative lens element and the second lens component which consists of a single positive lens element. In a case where the first lens component which consists of the single negative lens element has a refractive power insufficient for a certain specification item such as a field angle of the objective lens system, it is allowable to dispose an additional lens element having a negative refractive power in the first lens component. Further, it is allowable to dispose a lens element having a positive refractive power or use a cemented lens component for favorably correcting lateral chromatic aberration and astigmatism.

For correcting barrel distortion produced by an objective lens system which is composed only of spherical lens elements, it is sufficient to prevent a principal ray from being refracted excessively by using an aspherical surface in the first lens component on which the principal ray is high. Further, it is necessary for correcting longitudinal chromatic aberration by the second lens component to use a negative lens element having a high dispersing power and it is sufficient for this purpose to compose the second lens component of a combination of a positive lens element and a negative lens element. In such a case, the positive lens element and the negative lens element may be cemented to each other or disposed separately from each other. For the second lens component for which a magnification of approximately –1x is most desirable, it is sufficient to select a magnification within a range from –2x to –0.5x. If the second lens component has a magnification outside the range from –2x to –0.5x, the objective lens system will have a pupil at a location largely deviated from the middle between the leading end and a primary image, whereby marginal rays will undesirably be eclipsed.

Since the objective lens system which is to be used in the optical system of the non-flexible endoscope according to the present invention is configured so as to be long and have a numerical aperture nearly equal to that of a relay lens system, it is necessary to transmit a pupil together with an image. An image cannot be relayed with unchanged brightness unless a diameter of a light bundle which has passed through the pupil $Q_2$ of the relay lens system R is changed from that of the light bundle at a stage where it has passed through the pupil $Q_1$ of the objective lens system. Accordingly, it is desirable that a diameter $\phi_1$ of the light bundle as measured at the pupil $Q_1$ of the objective lens system and a diameter $\phi_2$ of the light bundle as measured at the pupil $Q_2$ of the relay lens system satisfy the following condition (10):

$$0.5 < \phi_1/\phi_2 < 1.5 \tag{10}$$

Further, when a distance $D_4$ as measured from the pupil $Q_1$ of the objective lens system O to the primary image $I_1$ is nearly equal to a distance $D_5$ as measured from the pupil $Q_2$ of the relay lens system R to the primary image $I_1$ the pupil $Q_1$ and the pupil $Q_2$ are located nearly symmetrical with regard to the primary image $I_1$, whereby a pupil can be relayed favorably with little loss of light intensity. Further, the primary field lens $F_1$ may be disposed on the side of the objective lens system O or the side of the relay lens system R of the primary image or can be located so as to comprise the primary field lens $F_1$ therein. However, intensity of marginal rays will be lowered when the primary field lens $F_1$ is too far from the primary image $I_1$. It is therefore desirable to dispose the primary field lens $F_1$ so as to reserve, between the primary field lens $F_1$ and the primary image $I_1$, a distance which is shorter than 10% of $D_3$. If the distance reserved between the primary field lens $F_1$ and the primary image $I_1$ exceeding 10% of $D_3$, the primary field lens $F_1$ itself will eclipse the offaxial rays, thereby eclipsing an image at a marginal portion of a visual field or lowering intensity of the marginal rays. The primary field lens $F_1$ must have a positive refractive power for transmitting a pupil and can be composed of a sing positive lens element so as to have a sufficient function thereof. When the primary field lens $F_1$ is to be used for correcting lateral chromatic aberration and astigmatism, however, it may be composed of a cemented lens component consisting of a positive lens element and a negative lens element.

Like the conventional non-flexible endoscope which uses a visual field mask disposed at an imaging location for clarifying a range of a visual field to be observed, the non-flexible endoscope according to the present invention may comprise a visual field mask. In such a case, it is most desirable to dispose a visual field mask consisting of a thin black metal sheet or the like at a location of a final intermediate image $I_n$ at which a spatial restriction is minimum. However, a visual field mask may be disposed at a location of the primary image $I_1$, any one of the other intermediate images $I_2$, $I_3$, . . . or in the first lens component of the objective lens system O on which the marginal rays are low and the principal ray is high.

Now, description will be made of an optical system which is to be used in the non-flexible endoscope according to the present invention and of a type comprising an objective lens system and a plurality of relay lens units.

The nineteenth embodiment of the present invention has a configuration illustrated in FIG. 31 which has already been described above. Speaking concretely, the nineteenth embodiment consists of an insert section 1 which is to be inserted into cavities of living bodies and the like, and a grip section 2 which is to be kept outside the cavities and comprises an eyepiece section 2 disposed in the vicinity of a near end thereof. An objective lens system is disposed in the leading end of the insert section 1 of the non-flexible endoscope, a relay lens system R for relaying a primary image $I_1$ of an object formed by the objective lens system O is disposed in the insert section 1, and an eyepiece lens system E which converts a light bundle coming from a final image $I_n$ into a nearly parallel light bundle is disposed in the eyepiece section 2.

The relay lens system R which is used in the optical system of the non-flexible endoscope preferred as the nineteenth embodiment illustrated in FIG. 31 is composed of relay lens units $R_1$, $R_2$ and $R_3$ for relaying an image in three cycles.

The optical system preferred as the nineteenth embodiment is configured so that a ratio between the length $D_1$ and $D_R$, i.e., the parameter ($D_1/D_R$) expressing a ratio between the length $D_1$ as measured from the leading end of the objective lens system O to the primary image $I_1$ and the distance as measured from the primary image $I_1$ to the next image $I_2$, satisfies the condition (9).

The twentieth embodiment illustrated in FIG. 32 has a configuration which is obtained by connecting a TV camera system 6 to the grip section 5 of the nineteenth embodiment, and uses on objective lens system O, a relay lens system R and an eyepiece lens system E which are the same as those disposed in the nineteenth embodiment. The TV camera system 6 comprisees an imaging lens system IL and a solid-state image pickup device 11 disposed at a location of an image formed by the imaging lens system IL.

When the TV camera system 6 is detachable from the grip section 5 in the twentieth embodiment, it is usable in various modes while exchanging the TV camera system 6 with different types of TV camera systems. Further, when the TV camera system 6 is configured so as to be dividable along a dashed line 6c, the twentieth embodiment can be used in a variety of modes by using a large number of combinations of a multiple kinds of adaptors 3a comprising imaging lens systems IL and a multiple kinds of TV camera heads 4b which are prepared at hand.

Furthermore, the twentieth embodiment can have a focusing fucntion and a vari-focal function which provide convenient adjustments of focusing positions and image surface sizes when lens elements to be disposed in the imaging lens system IL are configured so as to be movable in the adaptor 3a.

Figure 34:
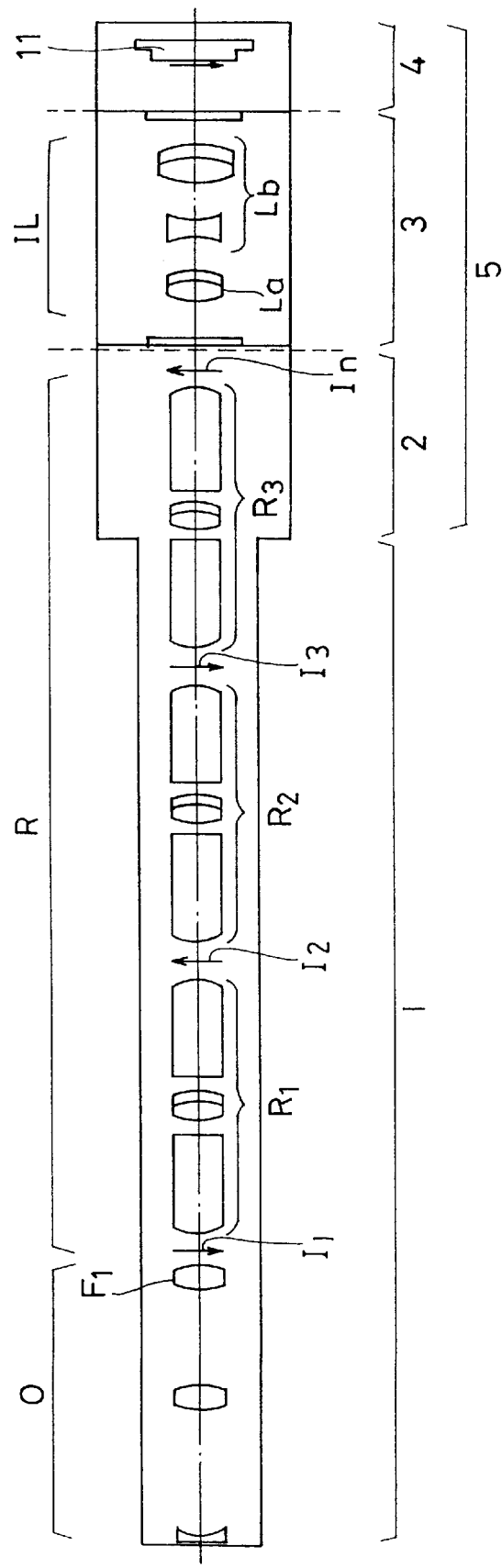
FIG. 34 shows a sectional view illustrating a composition of a twenty-first embodiment of the non-flexible endoscope according to the present invention.

The twenty-first embodiment of the present invention has a configuration illustrated in FIG. 34, or consists of an insert section 1, a grip section 5, an adaptor 3 connected to the grip section 5 and a TV camera head 4. An objective lens system O and a relay lens system R are disposed in the insertion sect 1 and the grip section 5, whereas an imaging lens system IL is disposed in the adaptor 3 for reimaging a final image $I_n$ formed by the relay lens system R onto a light receiving surface of an image pickup device 11 disposed in the TV camera head 4.

Unlike the nineteenth embodiment or the twentieth embodiment, the twenty-first embodiment uses no eyepice lens system, and therefore permits configuring a non-flexible endoscope and a TV adaptor compacter. Further, when the twenty-first embodiment is configured so as to permit detaching the insert section 1, the adaptor 3 and the TV camera head 4 from one another, it is usable in a variety of modes by using a large number of combinations of adaptors and TV camera heads which are prepared in a pluralities of kinds.

The twenty-first embodiment can have a focusing function and a vari-focal function for permitting adjustments of focusing locations and image surface sizes when a lens element $L_a$ or $L_b$, which is used for composing the imaging lens system IL disposed in the adaptor 3 is movable.

Figure 35:
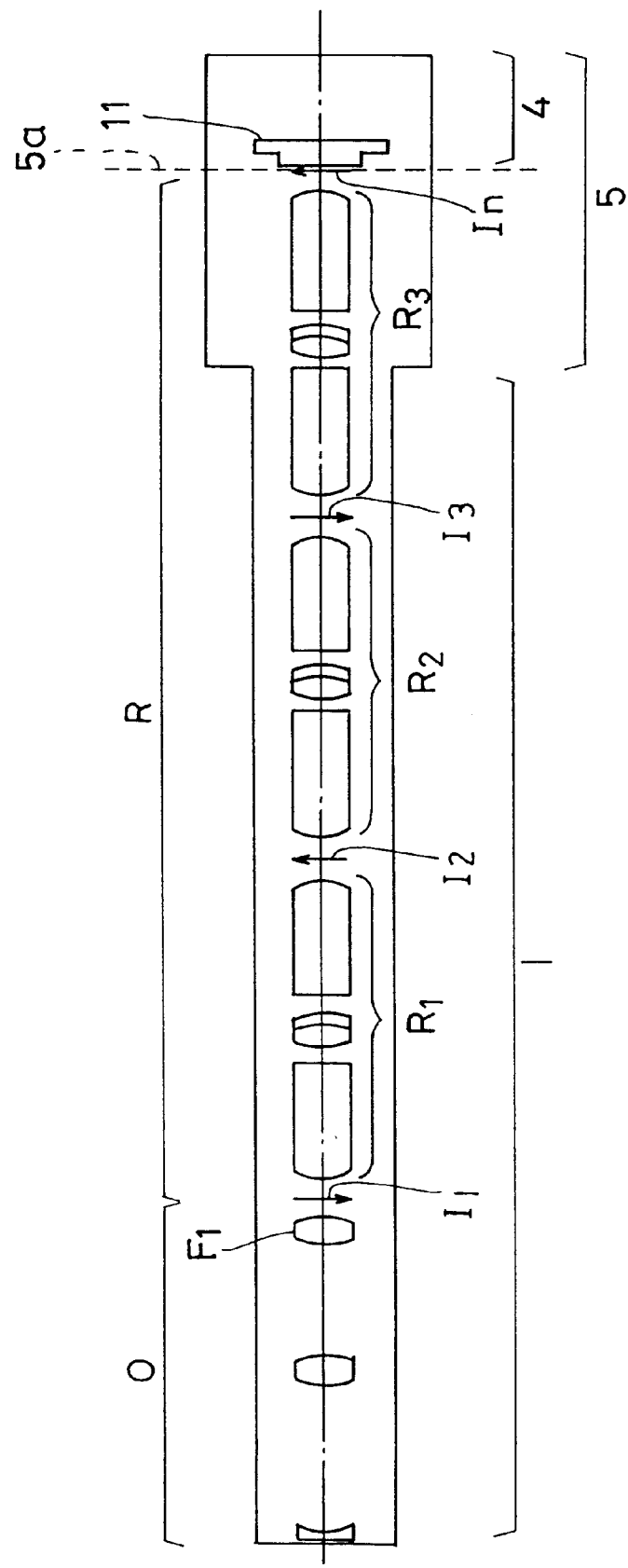
FIG. 35 shows a sectional view illustrating a composition of a twenty-second embodiment of the non-flexible endoscope according to the present invention.

The twenty-second embodiment of the present invention has a configuration illustrated in FIG. 35, or consists of an insert section 1 and a grip section 5. An objective lens system O and a relay lens system R are disposed in the insert section 1 and the grip section 5 respectively. Further, disposed in the grip section 5 is a solid-state image pickup device 11 for reimaging a final image $I_n$ formed in the optical system onto a light receiving surface of the solid-state image pickup device 11. Accordingly, the twenty-second embodiment permits configuring a TV observation system for the non-flexible endoscope compacter and enhancing operability thereof.

The twenty-second embodiment also permits configuring a TV camera head 4 so as to be detachable from the other sections and exchangeable with another.

Figure 36:
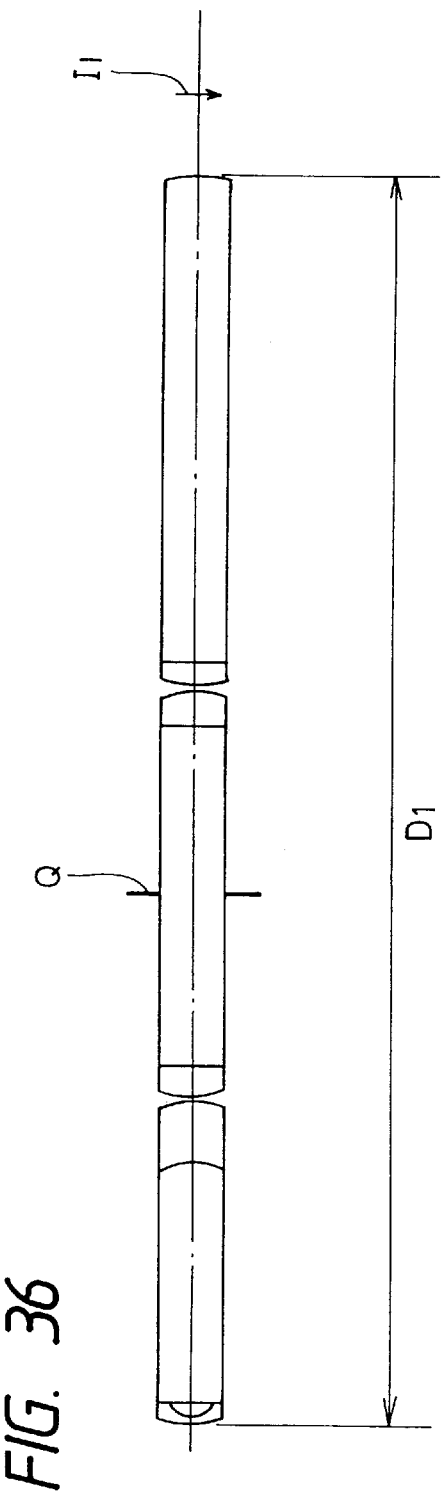
FIG. 36 shows a sectional view illustrating another example of the objective lens system to be used in the optical system of the non-flexible endoscope according to the present invention.
Figure 37:
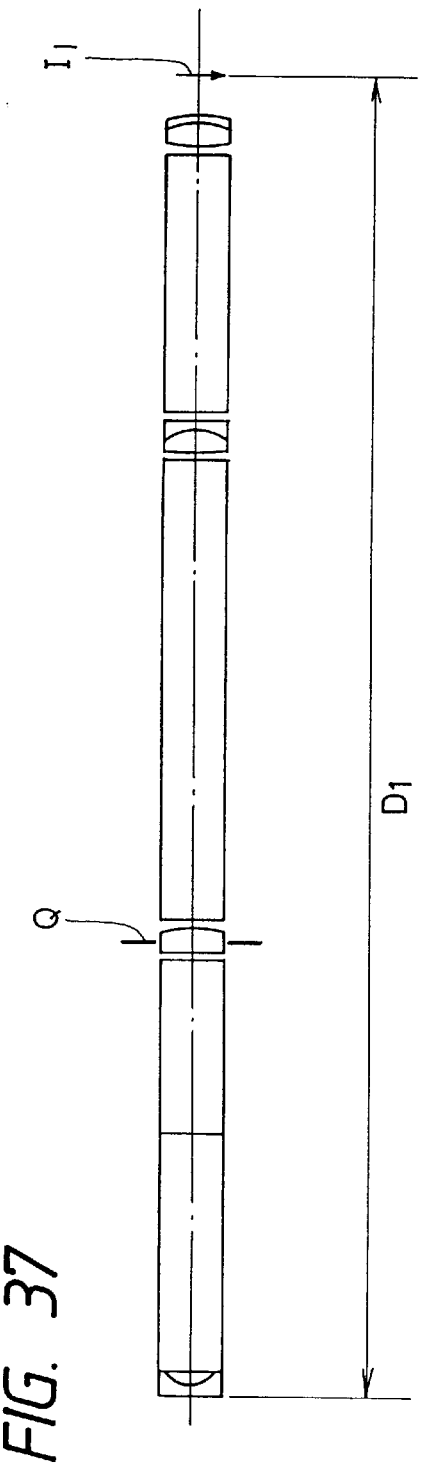
FIG. 37 shows a sectional view illustrating a still another example of the objective lens system to be used in the optical system of the non-flexible endoscope according to the present invention.

FIG. 36 and FIG. 37 exemplify objective lens systems which are composed of long rod-shaped lens components. When an objective lens system having a large total length is composed of a small number of lens components, it requires very long spacing rings for reserving required airspaces among the lens components. An optical system can be brightened by filling these airspaces with a glass material as in the conventional endoscope.

The objective lens systems illustrated in FIG. 36 and FIG. 37, in which the airspaces filled with air in the embodiment described above are filled with glass materials having high refractive indices, provide an effect equivalent to that available by shortening an effective length by prolonging an optical path length, thereby enabling to obtain optical systems which have enlarged numerical apertures or are brighter.

Figure 38:
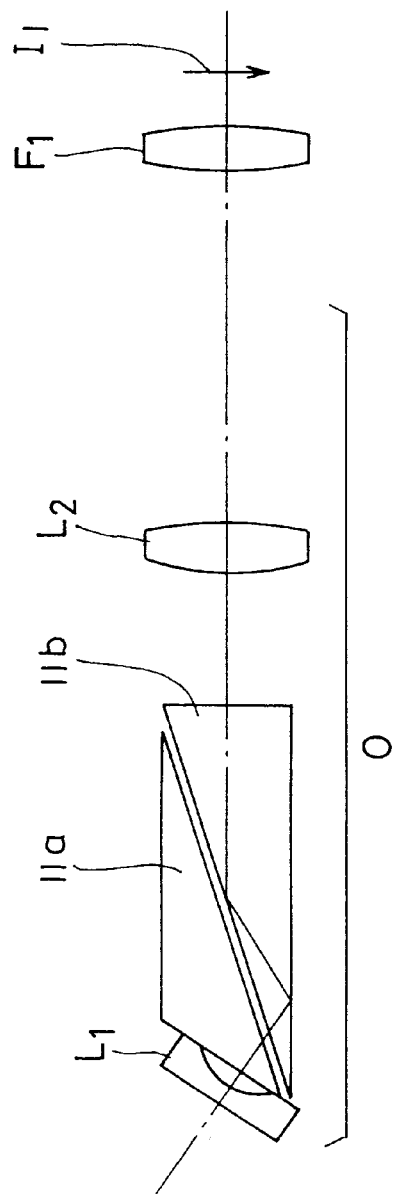
FIG. 38 shows a sectional view illustrating a composition of an objective lens system for oblique viewing to be used in the optical system of the non-flexible endoscopes according to the present invention.
Figure 39:
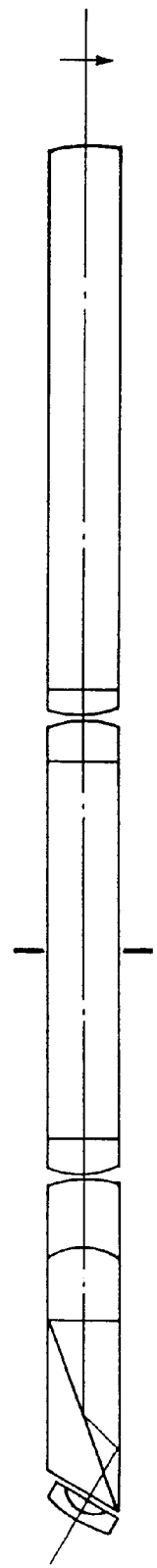
FIG. 39 shows a sectional view illustrating a composition of the objective lens system shown in FIG. 36 for the non-flexible endoscope according to the present invention when the objective lens system is modified for oblique viewing.

FIG. 38 and FIG. 39 illustrate oblique viewing optical systems for non-flexible endoscopes. These optical systems are usable also for straight viewing.

FIG. 38 is a sectional view illustrating an objective lens system O for the oblique viewing optical system for non-flexible endoscopes wherein oblique viewing prisms 11a and 11b are disposed on the side of a first lens component in a section between the first lens component and a second lens component of the objective lens system for configuring the optical system for oblique viewing. A space reserved between the prisms 11a and 11b is filled with air or an optical cementing agent which has a refractive index lower than a material of the prisms.

In this objective lens system, a light bundle incident thereon from an object passes through the first lens component and the prism 11a, transmits through a layer of the medium having the low refractive index, passes into the prism 11b, is totally reflected by a bottom surface of the prism 11b, reaches a slant surface of the prism 11b, and is reflected totally by a boundary between the layer of the medium having the low refractive index and the slant surface so as to travel toward the second lens component. It is desirable to coat the bottom surface of the prism 11b with a reflective film of a metal such as aluminium, but such a reflective metal film is unnecessary when a prism having high refractive index is used for total reflection. Though it is desirable to make the prisms 11a and 11b of a material having a high refractive index, such a material is limited to one of glass materials and can hardly allow manufacturing costs thereof to be reduced. Therefore, it is desirable for obtaining disposable prisms to select an optical plastic material such as an acrylic plastic material for the prisms 11a and 11b, and manufacture them by injection molding for reduction of manufacturing cost thereof. In this case, the prisms have a low refractive index and it is sufficient for total reflection on the slant surface of the prism 11b to reserve a space between the prisms 11a and 11b so as to form an air layer.

Figure 40:
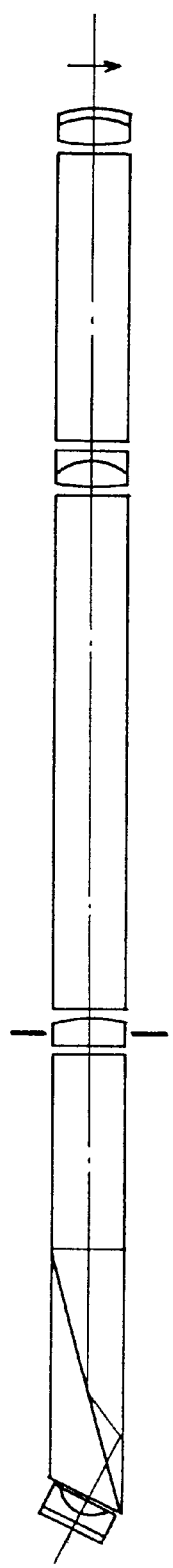
FIG. 40 shows a sectional view illustrating a composition of the objective lens system shown in FIG. 37 for the non-flexible endoscope according to the present invention when the objective lens system is modified for oblique viewing.

FIG. 39 and FIG. 40 show examples of oblique viewing objective lens systems which are obtained by modifying the objective lens systems illustrated in FIG. 36 and FIG. 37 respectively, and have compositions which can be realized by using oblique viewing prisms (the prisms 17a and 17b shown in FIG. 38) in place of the bar-shaped lens component disposed after the first lens component (the concave lens component) out of the bar-shaped lens components in the objective lens system shown in FIG. 36 or FIG. 37 in which spaces are filled with an optical material.

It is rather hard to design oblique viewing prisms for the objective lens system to be used in the optical system of the non-flexible endoscope according to the present invention in which rays are higher in the first lens component than the rays in the first lens component of the conventional objective lens systems which has a small total length. However, the composition which is described above permits reserving a sufficient effective diameter in prisms and makes it possible to design objective lens systems for oblique viewing non-flexible endoscopes.

Figure 41:
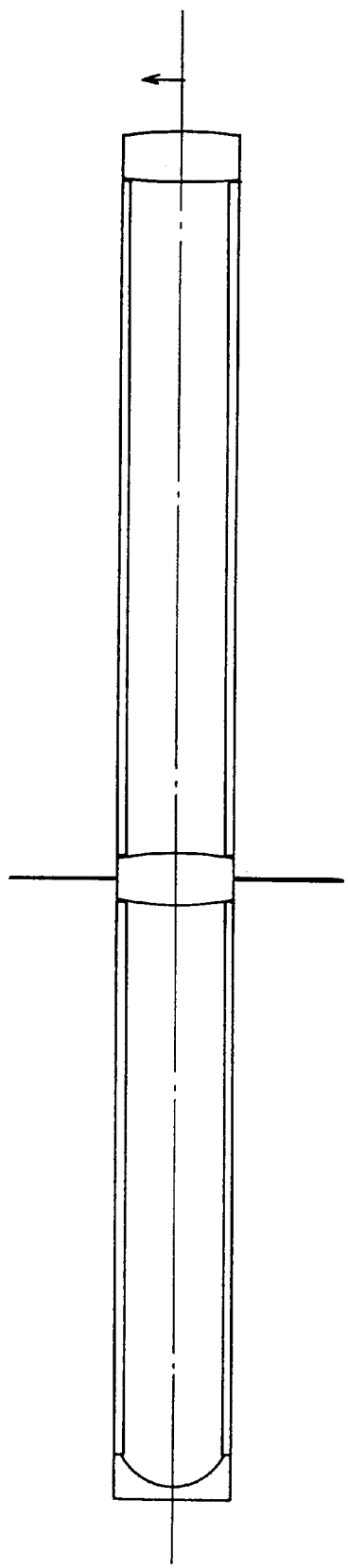
FIG. 41 shows a sectional view illustrating a composition of an objective lens system which is to be used in combination with a relay lens system performing three cycles of image relaying.

As is seen from FIG. 41 (illustrating an objective lens system for endoscopes performing three cycles of image relaying) and FIG. 42 (showing an objective lens system for non-flexible endoscopes performing five cycles of image relaying), the objective lens systems which are to be used in the optical system of the non-flexible endoscope according to the present invention comprise airspaces which are remarkably wider than those reserved in the conventional objective lens system for non-flexible endoscopes. It is therefore undesirable to use metallic spacing rings for holding the lens components at predetermined spacings in the objective lens systems for the non-flexible endoscope according to the present invention since such metallic spacing rings have inside surfaces which allow detrimental rays to be incident due to reflection thereon, thereby producing flare. The objective lens systems for the optical system of the non-flexible endoscope according to the present invention use spacing rings having inside surfaces which are roughened or sand-blasted so as to lower reflection thereon and prevent production of flare. Further, it is possible to obtain spacing rings having roughened inside surfaces by fabricating them with synthetic resin materials and mixing a foreign matter such as glass with the synthetic resin material at molding stages. These spacing rings can prevent produciton of flare.

Though the lens components to be used for composing the optical system of the non-flexible endoscope according to the present invention are ordinarily made of glass materials, a manufacturing cost of the optical system can be lowered by manufacturing the lens components by injection molding of optical plastic materials such a acrylic materials. It is desirable to compose each of the lens components of a single lens element and two lens elements may be disposed separately with a slight airspace reserved therebetween when a cemented lens component is required for composing the optical system.

In the objective lens system shown in FIG. 36 or FIG. 37, the location of the pupil Q is shifted toward the first lens component (the concave lens component) so that a small virtual image is formed in the vicinity of the first lens component and the principal ray is low on this lens component, thereby preventing a visual field from being eclipsed.

Figure 44:
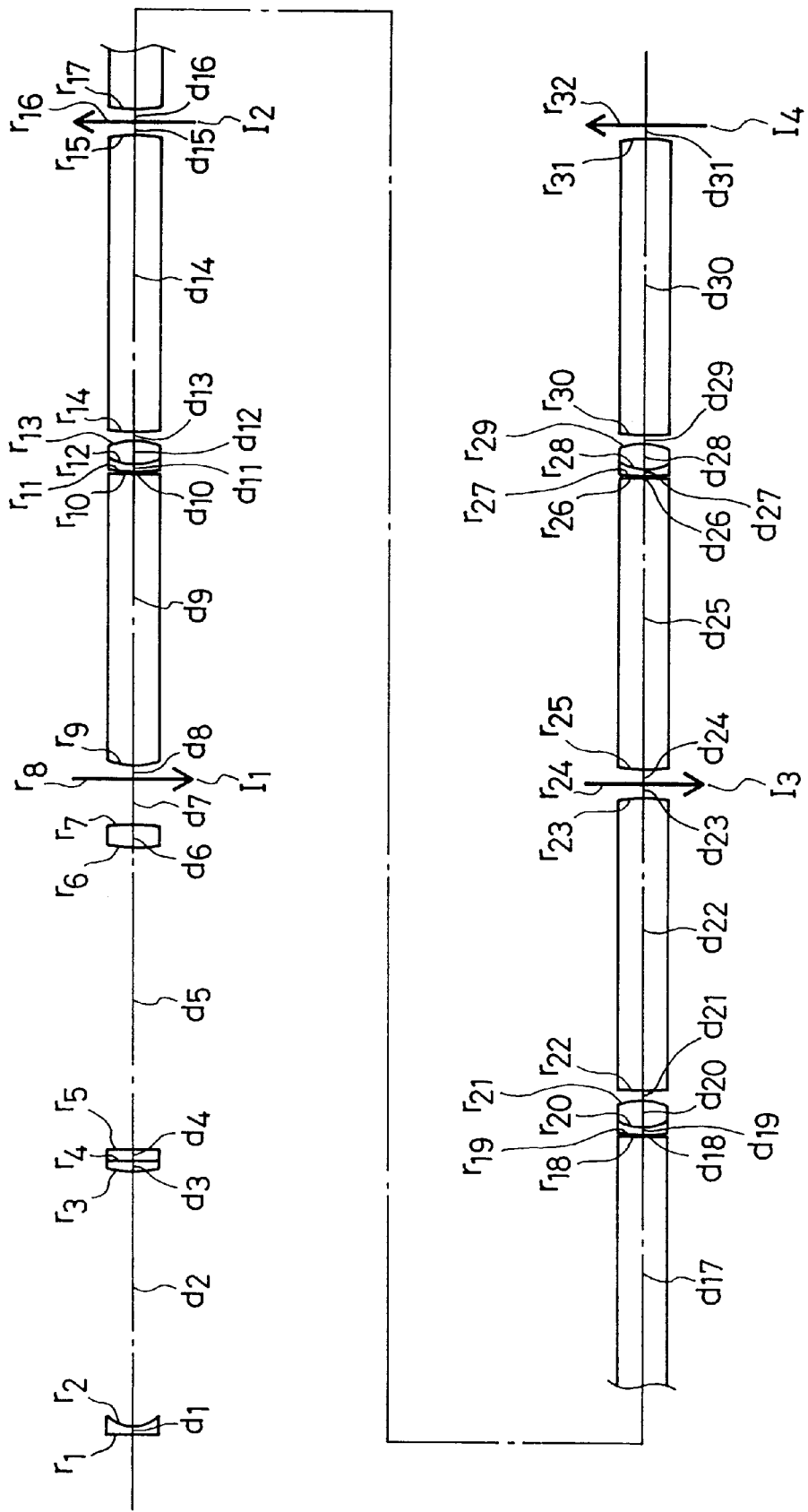
FIG. 44 shows a sectional view illustrating a composition of an optical system to be used in a twenty-third embodiment of the non-flexible endoscope according to the present invention.
Figure 45:
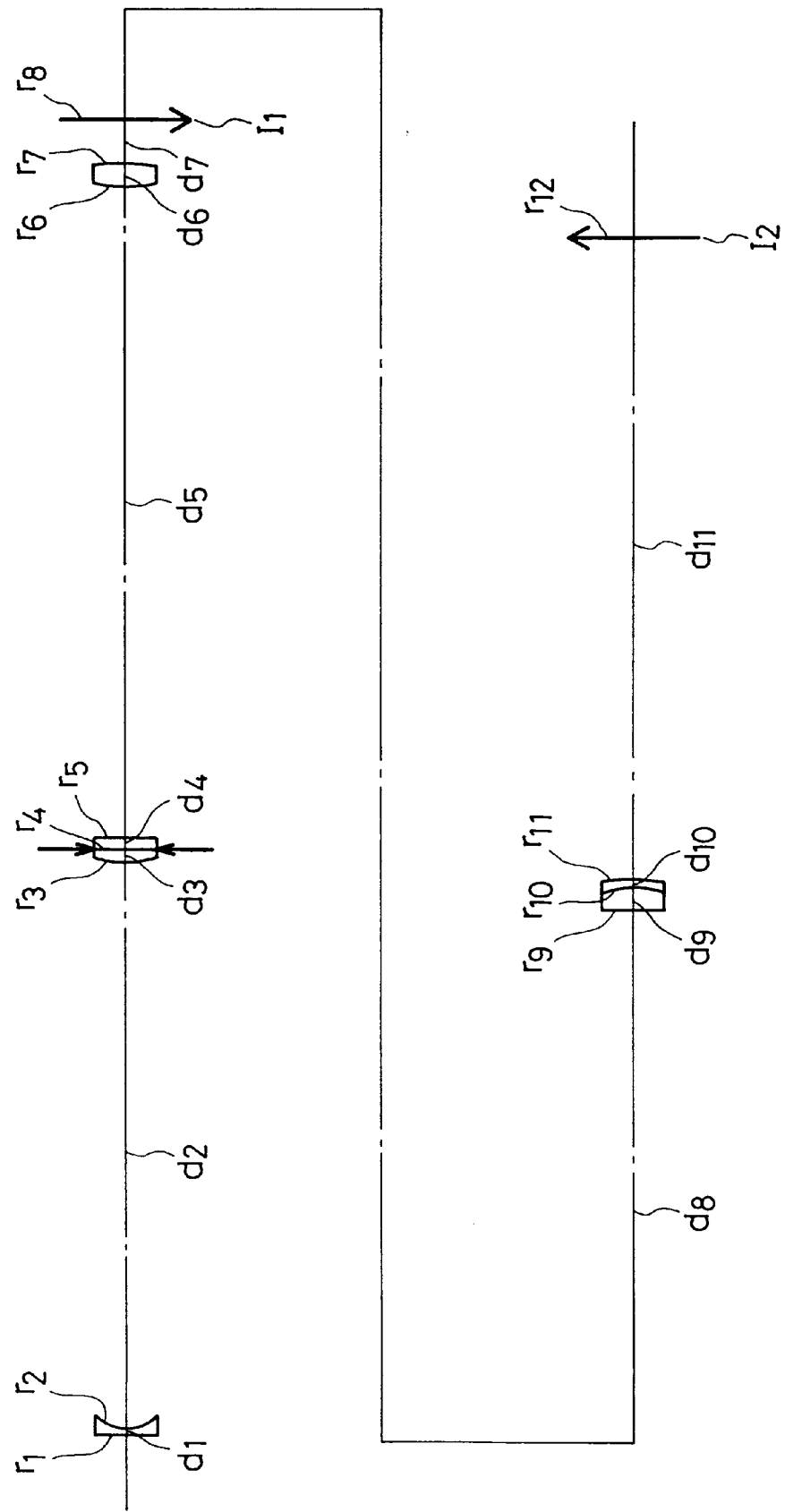
FIG. 45 shows a sectional view illustrating a composition of an optical system to be used in a twenty-fourth embodiment of the non-flexible endoscope according to the present invention.
Figures 46A, 46B, 46C, 46D:
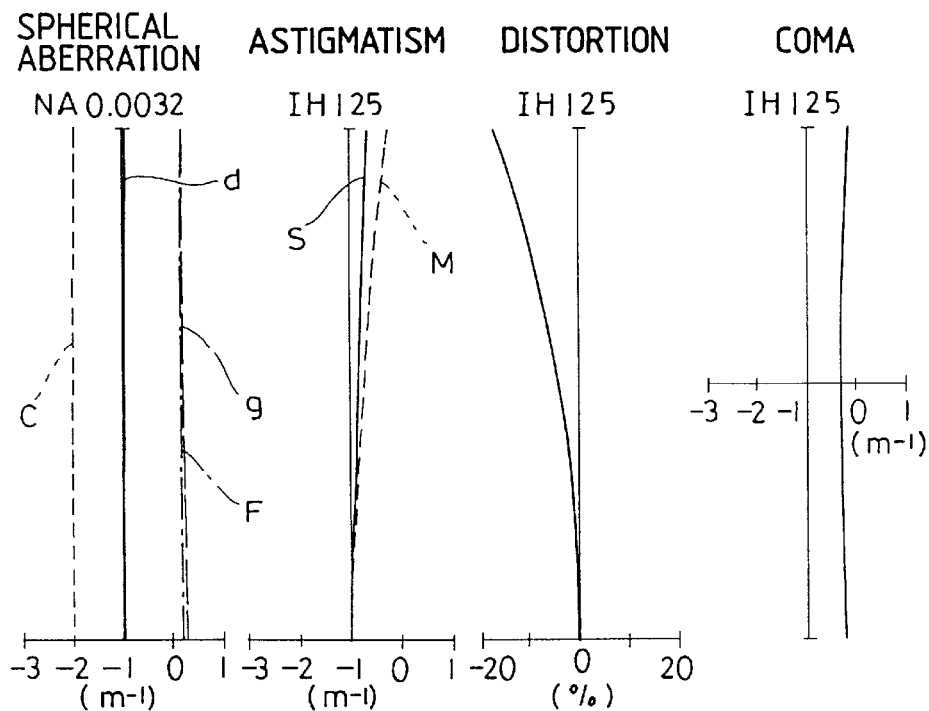
FIG. 46A, FIG. 46B, FIG. 46C and FIG. 46D show curves visualizing aberration characteristics of an optical system used in the first embodiment of the non-flexible endoscope according to the present invention.
Figures 47A, 47B, 47C, 47D:
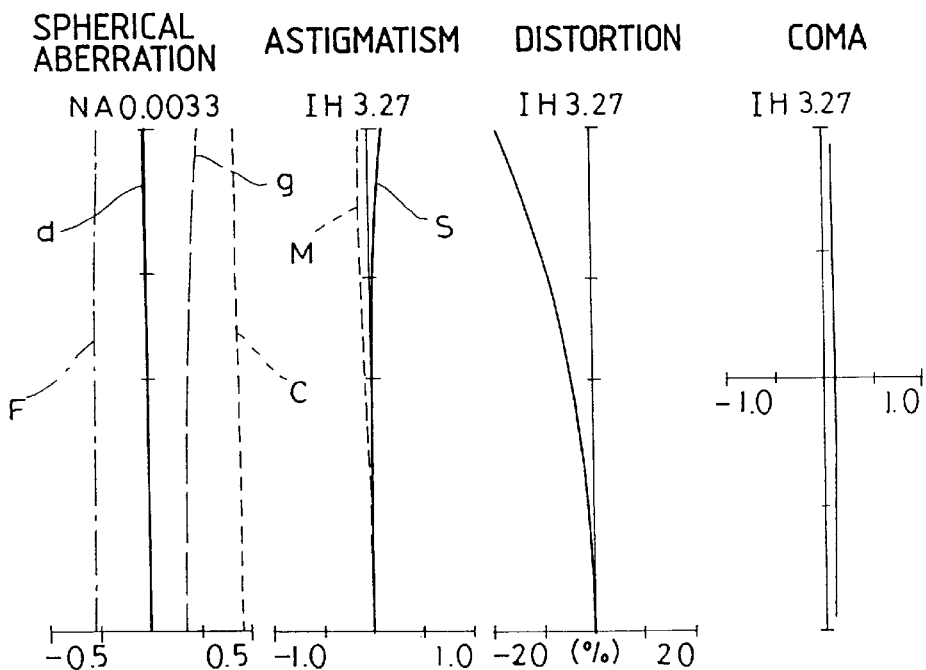
FIG. 47A, FIG. 47B, FIG. 47C and FIG. 47D show curves visualizing aberration characteristics of an optical system used in the second embodiment of the non-flexible endoscope according to the present invention.
Figures 52A, 52B, 52C, 52D:
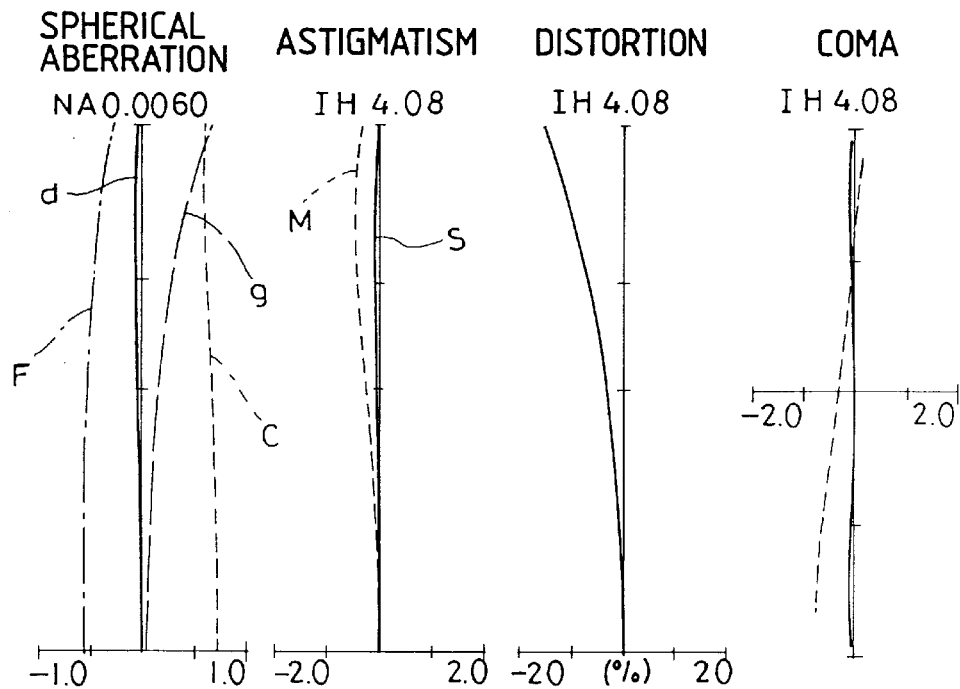
FIG. 52A, FIG. 52B, FIG. 52C and FIG. 52D show graphs illustrating aberration characteristics of an optical system used in the ninth embodiment of the non-flexible endoscope according to the present invention.

FIG. 44 and FIG. 45 (Embodiemnt 23 and Embodiment 24) show concrete examples of optical systems of the non-flexible endoscopes according to the present invention which are configured so as to perform a single image relaying cycle or a plurality of image relaying cycles, uses relay lens systems having shortened lengths and have numerical data listed below:

Embodiment 23 object distance = −30 mm, F No. = 7.16
image height = 2.18 mm, field angle = 60°
effective diameter of lens element = ⌀5.8 mm $r_1 = \infty$
$d_1 = 0.800$    $n_1 = 1.80610$    $\nu_1 = 40.95$
$r_2 = 3.5063$
$d_2 = 34.6896$
$r_3 = 22.3925$
$d_3 = 1.5000$    $n_2 = 1.51633$    $\nu_2 = 64.15$
$r_4 = \infty$
$d_4 = 1.5000$    $n_3 = 1.51633$    $\nu_3 = 64.15$
$r_5 = -22.3258$
$d_5 = 40.0104$
$r_6 = 42.0295$
$d_6 = 3.0000$    $n_4 = 1.51633$    $\nu_4 = 64.15$
$r_7 = -42.2079$
$d_7 = 6.0000$
$r_8 = \infty$ -continued object distance = −30 mm, F No. = 7.16
image height = 2.18 mm, field angle = 60°
effective diameter of lens element = ⌀5.8 mm $d_8 = 1.6886$
$r_9 = 17.0754$
$d_9 = 39.1310$    $n_5 = 1.62004$    $\nu_5 = 36.26$
$r_{10} = \infty$
$d_{10} = 0.2955$
$r_{11} = 20.9646$
$d_{11} = 1.0000$    $n_6 = 1.80610$    $\nu_6 = 40.95$
$r_{12} = 5.7017$
$d_{12} = 3.0000$    $n_7 = 1.65160$    $\nu_7 = 58.52$
$r_{13} = -10.5362$
$d_{13} = 1.5653$
$r_{14} = \infty$
$d_{14} = 39.1310$    $n_8 = 1.62004$    $\nu_8 = 36.26$
$r_{15} = -17.0754$
$d_{15} = 1.6886$
$r_{16} = \infty$
$d_{16} = 1.6886$
$r_{17} = 17.0754$
$d_{17} = 39.1310$    $n_9 = 1.62004$    $\nu_9 = 36.26$
$r_{18} = \infty$
$d_{18} = 0.2955$
$r_{19} = 20.9646$
$d_{19} = 1.0000$    $n_{10} = 1.80610$    $\nu_{10} = 40.95$
$r_{20} = 5.7017$
$d_{20} = 3.0000$    $n_{11} = 1.65160$    $\nu_{11} = 58.52$
$r_{21} = -10.5362$
$d_{21} = 1.5653$
$r_{22} = \infty$
$d_{22} = 39.1310$    $n_{12} = 1.62004$    $\nu_{12} = 36.26$
$r_{23} = -17.0754$
$d_{23} = 1.6886$
$r_{24} = \infty$
$d_{24} = 1.6886$
$r_{25} = 17.0754$
$d_{25} = 39.1310$    $n_{13} = 1.62004$    $\nu_{13} = 36.26$
$r_{26} = \infty$
$d_{26} = 0.2955$
$r_{27} = 20.9646$
$d_{27} = 1.0000$    $n_{14} = 1.80610$    $\nu_{14} = 40.95$
$r_{28} = 5.7017$
$d_{28} = 3.0000$    $n_{15} = 1.65160$    $\nu_{15} = 58.52$
$r_{29} = -10.5362$
$d_{29} = 1.5653$
$r_{30} = \infty$
$d_{30} = 39.1310$    $n_{16} = 1.62004$    $\nu_{16} = 36.26$
$r_{31} = -17.0754$
$d_{31} = 1.6886$
$r_{32} = \infty$
$D_1 = 87.5$ mm, $D_2 = 87.5$ mm, $D_1/D_2 = 1$ Embodiment 24 object distance = −30 mm, F No. = 11.62,
image height = 2.9, field angle = 60°
effective diameter of lens element = ⌀7.4 mm $r_1 = \infty$
$d_1 = 0.800$    $n_1 = 1.80610$    $\nu_1 = 40.95$
$r_2 = 5.1100$
$d_2 = 75.7700$
$r_3 = 45.3700$
$d_3 = 1.5000$    $n_2 = 1.51633$    $\nu_2 = 64.15$
$r_4 = \infty$
$d_4 = 1.5000$    $n_3 = 1.51633$    $\nu_3 = 64.15$
$r_5 = -45.3700$
$d_5 = 86.4200$
$r_6 = 44.1060$
$d_6 = 3.0000$    $n_4 = 1.51633$    $\nu_4 = 64.15$
$r_7 = -44.1060$
$d_7 = 6.0000$
$r_8 = \infty$
$d_8 = 85.6300$
$r_9 = 30.7220$ -continued object distance = −30 mm, F No. = 11.62,
image height = 2.9, field angle = 60°
effective diameter of lens element = ⌀7.4 mm

|  | $d_9 = 3.0000$ | $n_5 = 1.51633$ | $v_5 = 64.15$ |
|---|---|---|---|
| $r_{10} =$ | −14.7370 | | |
|  | $d_{10} = 1.0000$ | $n_6 = 1.78472$ | $v_6 = 25.71$ |
| $r_{11} =$ | −31.7910 | | |
|  | $d_{11} = 85.3600$ | | |
| $r_{12} =$ | ∞ | | |

$D_1 = 174.99$ mm, $D_2 = 174.99$ mm, $D_1/D_2 = 1$

Out of the optical system described above, an optical system which performs three cycles of image relaying is illustrated in FIG. 44 and an optical system which performs a single cycle of image relaying is shown in FIG. 45. These optical systems are configured so as to satisfy the condition (9).

The present invention provide an optical system for non-flexible endoscopes which is bright or has a numerical aperture enlarged by determining a location of a primary image to be formed by an objective lens system so as to shorten a length required for relaying the primary image by one cycle.

I claim:

1. A non-flexible endoscope comprising:
a slender insert section which is to be inserted from a leading end thereof into cavities of an object to be observed for observing interiors thereof,
wherein an observation optical system consisting only of an objective lens system is disposed in said insert section,
wherein said objective lens system forms a primary image of the object to be observed at a location in the vicinity of an end located on a side opposite to said leading end,
wherein said objective lens system comprises a first negative lens component which is disposed in the vicinity of the leading end of said insert section and second positive lens component which is disposed in the vicinity of a middle location in said insert section, and
wherein said second lens component satisfies the following condition (1):

$$0.7 < |B_2| < 1.5 \tag{1}$$

wherein the reference symbol $B_2$ represents a magnification of said second lens component.

2. A non-flexible endoscope comprising:
a slender insert section which is to be inserted from a leading end thereof into cavities of an object to be observed for observing interiors thereof,
wherein an observation optical system consisting only of an objective lens system is disposed in said insert section,
wherein said objective lens system forms a primary image of the object to be observed at a location in the vicinity of an end located on a side opposite to said leading end, and
wherein said endoscope satisfies the following condition (2):

$$0.7 < D_1/D_e < 1.5 \tag{2}$$

wherein the reference symbol $D_1$ represents a distance as measured from a first surface of said objective lens system to said primary image and the reference symbol $D_e$ designates an effective length of said insert section.

3. A non-flexible endoscope, comprising:
a slender insert section which is to be inserted from a leading end thereof into cavities of an object to be observed for observing interiors thereof,
wherein an observation optical system consisting only of an objective lens system is disposed in said insert section,
wherein said objective lens system forms a primary image of the object to be observed at a location in the vicinity of an end located on a side opposite to said leading end,
wherein said objective lens system comprises a first negative lens component which is disposed in the vicinity of the leading end of said insert section and second positive lens component which is disposed in the vicinity of a middle location in said insert section, and
wherein said objective lens system is composed of a first negative lens component which is a single plano-concave lens element disposed in the vicinity of a leading end of said insert section and a second lens component which is a piano-convex lens element disposed in the vicinity of a middle of said insert section, and satisfies the following condition (3):

$$n_1 > n_2, \; v_1 < v_2 \tag{3}$$

wherein the reference symbols $n_1$ and $n_2$ represents refractive indices of said first lens components and said second lens component respectively, and the reference symbols $v_1$ and $v_2$ designate Abbe's numbers of said first lens component and said second lens component respectively.

4. A non-flexible endoscope according to claim 1, 2 or 3, further comprising an eyepiece section, which is to be attached to an end of said insert section located on a side opposite to said leading end,
wherein an eyepiece lens system is disposed in said eyepiece section,
wherein said eyepiece lens system converts rays coming from said primary image into a nearly parallel light bundle, and
wherein said insert section and said eyepiece section are attachable to and detachable from each other.

5. A non-flexible endoscope according to claim 1, 2 or 3, further comprising an imaging device to be attached to an end of said insert section which is located on a side opposite to said leading end,
wherein said imaging device comprises an imaging lens system for reimaging said primary image and an image pickup device which is disposed at a location of an image formed by said imaging lens system, and
wherein said insert section and said imaging device are attachable to and detachable from each other.

6. A non-flexible endoscope according to claim 3 wherein said first lens component has an image side concave surface which is configured as a aspherical surface having such a shape as to lower curvature as portions of the aspherical surface are farther from an optical axis thereof.

7. A non-flexible endoscope according to claim 3 wherein said first lens component is composed only of a single plano-concave lens element, wherein said second lens component is composed of a biconvex cemented lens component which consists of a positive lens element and a negative lens element, and wherein said objective lens system satisfies the following condition (4):

$$n_p < n_N, \quad v_p > v_N \qquad (4)$$

wherein the reference symbols $n_p$ and $v_p$ represents a refractive index and an Abbe's number respectively of the positive lens element of said cemented lens component, and the reference symbols $n_N$ and $v_N$ designate a refractive index and an Abbe's number respectively of the negative lens elements of said cemented lens component.

* * * * *